U S007869958B2

(12) United States Patent
Royappa et al.

(10) Patent No.: US 7,869,958 B2
(45) Date of Patent: Jan. 11, 2011

(54) STRUCTURE-BASED MODULATORS OF B1 G-PROTEIN COUPLED RECEPTORS

(75) Inventors: Grace Christy Rani Royappa, La Jolla, CA (US); Marilyn H. Perrin, La Jolla, CA (US); Jean E. Rivier, La Jolla, CA (US); Wylie W. Vale, Jr., La Jolla, CA (US); Roland Riek, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 1248 days.

(21) Appl. No.: 11/199,821

(22) Filed: Aug. 9, 2005

(65) Prior Publication Data

US 2006/0069516 A1 Mar. 30, 2006

Related U.S. Application Data

(60) Provisional application No. 60/599,936, filed on Aug. 9, 2004.

(51) Int. Cl.
G06G 7/58 (2006.01)
(52) U.S. Cl. .......................................... 702/19; 703/11
(58) Field of Classification Search ...................... None
See application file for complete search history.

(56) References Cited

U.S. PATENT DOCUMENTS

| | | | |
|---|---|---|---|
| 4,282,287 A | 8/1981 | Giese | |
| 4,542,102 A | 9/1985 | Dattagupta et al. | |
| 4,612,132 A | 9/1986 | Wollenberg et al. | |
| 4,812,128 A | 3/1989 | Mikelsaar | |
| 4,906,122 A | 3/1990 | Barrett et al. | |
| 5,030,103 A | 7/1991 | Buist et al. | |
| 5,252,743 A | 10/1993 | Barrett et al. | |
| 5,583,973 A | 12/1996 | DeLisi et al. | |
| 5,612,894 A | 3/1997 | Wertz | |
| 5,643,873 A | 7/1997 | Barrett et al. | |
| 5,654,276 A | 8/1997 | Barrett et al. | |
| 6,080,576 A | 6/2000 | Zambrowicz et al. | |
| 6,093,573 A | 7/2000 | Beamer et al. | |
| 6,348,466 B1 | 2/2002 | Haddach et al. | |
| 6,500,839 B2 | 12/2002 | Haddach et al. | |
| 6,514,982 B1 | 2/2003 | Haddach et al. | |
| 6,531,475 B1 | 3/2003 | Haddach et al. | |
| 6,541,469 B2 | 4/2003 | Haddach | |
| 6,583,143 B2 | 6/2003 | Haddach | |
| 6,664,261 B2 | 12/2003 | Chen et al. | |
| 6,747,034 B2 | 6/2004 | Haddach et al. | |

FOREIGN PATENT DOCUMENTS

| WO | 84/03564 | 9/1984 |
|---|---|---|
| WO | 90/07582 | 7/1990 |
| WO | 91/00868 | 1/1991 |
| WO | 91/07087 | 5/1991 |

OTHER PUBLICATIONS

Goodsell et al., Journal of Molecular Recognition, 1996, vol. 9, pp. 1-5.*
Böhm et al., Journal of Computer-Aided Molecular Design, 1996, vol. 10, pp. 265-272.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Ginalski et al., Comparative Modeling for Protein Structure Prediction. Current Opinion in Structural Biololgy, 2006. vol. 16, pp. 172-177.*
Franzoni et al., "Structure of two fragments of the third cytoplasmic loop of the rat angiotensin II AT1A receptor: Implications with respect to receptor activation and G-protein selection and coupling," *J. of Biological Chem.*, 274:227-235, 1999.
Pellegrini et al., "Structural characterization of peptide hormone/receptor interactions by nmr spectroscopy," *Bioplymers*, 51:208-209, 212, 217, 1999.
Terstappen et al, "In Silico Research in Drug Discovery," *Trends in Pharmacological Sciences*, 22:23-26, 2001.
Yeagle et al., "Studies on the structure of the G-protein-coupled receptor rhodopsin including the putative G-protein binding site in unactivated and activated forms," *Biochemistry*, 40:11932-11937, 2001.
Bugg et al., "Drugs by design," *Scientific American*, 92-98, 1993.
Dautzenberg et al., "Binding differences of human and amphibian corticotropin-releasing factor type 1 (CRF(1)) receptors: identification of amino acids mediating high-affinity astressin binding and functional antagonism," *Regul. Pept.*, 118: 165-173, 2004.
Dautzenberg et al., "Five amino acids of the *Xenopus laevis* CRF (corticotropin-releasing factor) type 2 receptor mediate differential binding of CRF ligands in comparison with its human counterpart," *Mol. Pharmacol.*, 61: 1132-1139, 2002.
Furth et al., "Temporal control of gene expression in transgenic mice by a tetracycline-responsive promoter," *Proc. Natl. Acad. Sci. USA*, 91: 9302-9306, 1994.
George et al., "Mutation data matrix and its uses," *Methods Enzymol*, 183: 333-351, 1990.

(Continued)

*Primary Examiner*—Suzanne M. Noakes
(74) *Attorney, Agent, or Firm*—Fulbright & Jaworski L.L.P.

(57) ABSTRACT

The present invention relates to a method for identifying modulators of B1 G-protein coupled receptors. The present invention also relates to a method for identifying an antagonist or agonist of the corticotropin-releasing factor receptor 2 (CRFR2). The present invention also relates to a method for improving antagonists or agonists of CRFR2. The present invention also relates to the three-dimensional structure of CRFR2 as representative of the B1 GPCR subfamily and its use as a basis for rational drug design of antagonist or agonists of B1 GPCRs.

7 Claims, 4 Drawing Sheets

OTHER PUBLICATIONS

Gossen et al., "Tight control of gene expression in mammalian cells by tetracycline-responsive promoters," *Proc. Natl. Acad. Sci. USA*, 89: 5547-5551, 1992.

Gossen et al., "Transcriptional activation by tetracyclines in mammalian cells," *Science*, 268: 1766-1769, 1995.

Grace et al., "NMR structure and peptide hormone binding site of the first extracellular domain of a type B1 G protein-coupled receptor," *Proc. Natl. Acad. Sci. USA*, 101(35): 12836-12841, 2004.

Hackeng et al., "Protein synthesis by native chemical ligation: expanded scope by using straightforward methodology," *Proc. Natl. Acad. Sci. USA*, 96: 10068-10073, 1999.

Johnson et al., "A structural basis for sequence comparisons. An evaluation of scoring methodologies," *J. Mol. Biol.*, 233(4): 716-738, 1993.

Kawashima and Kanehisa, "AAindex: amino acid index database," *Nucleic Acids Res.*, 28(1): 374, 2000.

No et al., "Ecdysone-inducible gene expression in mammalian cells and transgenic mice," *Proc. Natl. Acad. Sci. USA*, 93: 3346-3351, 1996.

Perrin et al., "A soluble form of the first extracellular domain of mouse type 2beta corticotropin-releasing factor receptor reveals differential ligand specificity," *J. Biol. Chem.*, 278: 15595-600, 2003.

Riek et al., "Evolutionary conservation of both the hydrophilic and hydrophobic nature of transmembrane residues," *J. Theor. Biol.*, 172: 245-258, 1995.

Szabo et al., "Surface plasmon resonance and its use in biomolecular interaction analysis (BIA)," *Curr. Opin. Struct. Biol*, 5: 699-705, 1995.

West et al., "Targeting HIV-1 protease: a test of drug-design methodologies," *Trends Pharmacol. Sci.*, 16(2): 67-75, 1995.

Wille et al., "Identification of amino acids in the N-terminal domain of corticotropin-releasing factor receptor 1 that are important determinants of high-affinity ligand binding," *J. Neurochem.*, 72: 388-395, 1999.

* cited by examiner

```
                              SEQUENCE LISTING

<160> NUMBER OF SEQ ID NOS: 39

<210> SEQ ID NO 1
<211> LENGTH: 2617
<212> TYPE: DNA
<213> ORGANISM: Mus musculus

<400> SEQUENCE: 1
gggcattacc ttggtgggta ggtcgggcag ggtaggacag gcctaagaga gaggccggac      60
agacctcctt tggaagcagc cacttctggt ccccatccct ggagcgatcg agcggcagga    120
tctgctgtcc catggggacc ccaggctctc ttcccagtgc acagcttctc ctctgcctgt    180
tttccctgct tccagtgctc caggtggccc aaccaggcca ggcaccccag gaccagcccc    240
tgtggacact tttggagcag tactgccaca ggaccacaat tgggaatttt tcaggtccct    300
acacctactg caacacgacc ttggaccaga tcgggacctg ctggccacag agcgcacccg    360
gagccctagt agagagaccg tgccccgagt acttcaatgg catcaagtac aacacgaccc    420
ggaatgccta cagagagtgc ctggagaacg ggacctgggc ctcaagggtc aactactcac    480
actgcgaacc cattttggat gacaagagaa agtatgacct gcattaccga atcgccctca    540
ttgtcaacta cctgggtcac tgtgtttccg tggtggccct ggtggccgct ttcctgcttt    600
tcctagtgct gcggagtatc cgctgcctga ggaatgtgat ccactggaac ctcatcacca    660
ccttcattct gagaaacatc gcgtggttcc tgctgcaact catcgaccac gaagtgcacg    720
agggcaatga ggtctggtgc cgctgcatca ccaccatctt caactatttt gtggtcacca    780
acttcttctg gatgtttgtg gagggctgct acctgcacac ggccattgtc atgacgtact    840
ccacagagca cctgcgcaag tggctttcc tcttcattgg atggtgcatt ccctgcccta    900
tcatcatcgc ctgggcagtt ggcaaactct actatgagaa tgagcagtgc tggtttggca    960
aggaagctgg tgatttggtg gactacatct accagggccc cgtcatgctt gtgctgttga   1020 tcaatttgt atttctgttt aacatcgtca ggatcctgat gacgaagtta cgagcatcca   1080
ccacgtccga gacaatccaa tacaggaagg cagtgaaggc cacgctggtc ctcctccccc   1140
tgttgggcat cacctacatg ctcttctttg tcaatcctgg cgaggacgac ctgtcccaga   1200
```

-continued

```
ttgtgttcat ctacttcaac tctttcctgc agtccttcca gggtttcttt gtgtccgttt    1260
tctactgctt cttcaatgga gaggtgcgcg cggccctgag aaacgggtgg caccgctggc    1320
aggaccacca cgcccctccgg gtgcctgtgg cccgggccat gtccatccct acgtcgccca    1380
ccaggatcag cttccacagc atcaagcaga cagctgctgt gtgaccctct gtcaccgtct    1440
gcccggcagt ccaccactga ggcagcttct ccatccttta cagccttccc ctgggtcctc    1500
cttgctaccc tgacccacag ggtacaaggt acaggagaag ggaggagaac gaacactccc    1560
gcctggaagg aaaggaaagc tatgacatgg ggggctctg aaggaccagg cccagtgca     1620 gccagccaca catctccaag cacgaaggag caggaggaca tcacaggacc ctcagaaggg    1680
atgcatctca caccatcaag cctctgtgca cccagcctct tttgtggggt cctcactgca    1740
gcaccattta catctgaaga aactgaggct cagagcaggc agggacctgg ccaagtcaca    1800
tagctacttg ccccacccac agcacccaca gttggctctg ctccttgctt tccatctcca    1860
cacgtgaggg cgccctctaa aggtgaggga acaagaatg accttatctg gcttcatccc     1920
agaagctgtc gagcagagat gaccagccct ttaccaaggt agccttcttc ttccccagtc    1980
tgtttcccat gtgtctccag gagaatgctg gctttcagtc ggccatccct cctgggagtc    2040
cccaattcag tctgggctca gtctggggac ctagaccacg ggaagtgagt tagatggaaa    2100
gtcacactct ccacagtgcc agacagaagg gagaacagaa gcgcctgggg aagaagggtg    2160
aggatccccc aaatcagagt atgcctggga gtgattgaaa caagggcccc aggatctcag    2220
tgacatcagc caggcatctg tggagttggc acaattcaa gcaacgagat gttggagaga    2280
tattgtgagc cagtaataaa ggcagaatgt ctgcaggaca tatccatgcc cctcttctta    2340
ctggctaggc ccaagcaggc cttcctgtgg agtctttagg ttcaaagggc ccgaatcatt    2400
cctgtcaccc caaagggtgg catctgcacc accccagcg tagaccccac ctgtgccagg     2460
gactaatatt ctggaattgg gagggagagg aggcaaggcc cttcaggctc cgaaagcaag    2520
aagacacagt ttgatttcag gcttctcttc cattcctctg tccctggagc agaagagggg    2580
tgttggggca agccaacaga cttgaaaagg ccccgg                              2617
```

<210> SEQ ID NO 2
<211> LENGTH: 430
<212> TYPE: PRT
<213> ORGANISM: Mus musculus

<400> SEQUENCE: 2

Met Gly Thr Pro Gly Ser Leu Pro Ser Ala Gln Leu Leu Leu Cys Leu
1               5                   10                  15

Phe Ser Leu Leu Pro Val Leu Gln Val Ala Gln Pro Gly Gln Ala Pro
                20                  25                  30

Gln Asp Gln Pro Leu Trp Thr Leu Leu Glu Gln Tyr Cys His Arg Thr
            35                  40                  45

Thr Ile Gly Asn Phe Ser Gly Pro Tyr Thr Tyr Cys Asn Thr Thr Leu
        50                  55                  60

Asp Gln Ile Gly Thr Cys Trp Pro Gln Ser Ala Pro Gly Ala Leu Val
65                  70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
            100                 105                 110

Val Asn Tyr Ser His Cys Glu Pro Ile Leu Asp Asp Lys Arg Lys Tyr

-continued

```
                115                 120                 125
Asp Leu His Tyr Arg Ile Ala Leu Ile Val Asn Tyr Leu Gly His Cys
            130                 135                 140
Val Ser Val Val Ala Leu Val Ala Ala Phe Leu Leu Phe Leu Val Leu
145                 150                 155                 160
Arg Ser Ile Arg Cys Leu Arg Asn Val Ile His Trp Asn Leu Ile Thr
            165                 170                 175
Thr Phe Ile Leu Arg Asn Ile Ala Trp Phe Leu Leu Gln Leu Ile Asp
            180                 185                 190
His Glu Val His Glu Gly Asn Glu Val Trp Cys Arg Cys Ile Thr Thr
            195                 200                 205
Ile Phe Asn Tyr Phe Val Val Thr Asn Phe Phe Trp Met Phe Val Glu
            210                 215                 220
Gly Cys Tyr Leu His Thr Ala Ile Val Met Thr Tyr Ser Thr Glu His
225                 230                 235                 240
Leu Arg Lys Trp Leu Phe Leu Phe Ile Gly Trp Cys Ile Pro Cys Pro
            245                 250                 255
Ile Ile Ile Ala Trp Ala Val Gly Lys Leu Tyr Tyr Glu Asn Glu Gln
            260                 265                 270
Cys Trp Phe Gly Lys Glu Ala Gly Asp Leu Val Asp Tyr Ile Tyr Gln
            275                 280                 285
Gly Pro Val Met Leu Val Leu Leu Ile Asn Phe Val Phe Leu Phe Asn
            290                 295                 300
Ile Val Arg Ile Leu Met Thr Lys Leu Arg Ala Ser Thr Thr Ser Glu
305                 310                 315                 320
Thr Ile Gln Tyr Arg Lys Ala Val Lys Ala Thr Leu Val Leu Leu Pro
            325                 330                 335
Leu Leu Gly Ile Thr Tyr Met Leu Phe Phe Val Asn Pro Gly Glu Asp
            340                 345                 350
Asp Leu Ser Gln Ile Val Phe Ile Tyr Phe Asn Ser Phe Leu Gln Ser
            355                 360                 365
Phe Gln Gly Phe Phe Val Ser Val Phe Tyr Cys Phe Phe Asn Gly Glu
            370                 375                 380
Val Arg Ala Ala Leu Arg Asn Gly Trp His Arg Trp Gln Asp His His
385                 390                 395                 400
Ala Leu Arg Val Pro Val Ala Arg Ala Met Ser Ile Pro Thr Ser Pro
            405                 410                 415
Thr Arg Ile Ser Phe His Ser Ile Lys Gln Thr Ala Ala Val
            420                 425                 430

<210> SEQ ID NO 3
<211> LENGTH: 2107
<212> TYPE: DNA
<213> ORGANISM: Homo sapiens

<400> SEQUENCE: 3
atggacgcgg cactgctcca cagcctgctg gaggccaact gcagcctggc gctggctgaa      60
gagctgctct tggacggctg ggggccaccc ctggaccccg agggtcccta ctcctactgc     120
aacacgacct tggaccagat cggaacgtgc tggccccgca cgctgccgg agccctcgtg     180 gagaggccgt gccccgagta cttcaacggc gtcaagtaca cacgacccg gaatgcctat     240 cgagaatgct tggagaatgg acgtgggcc tcaaagatca actactcaca gtgtgagccc     300
attttggatg acaagcagag gaagtatgac ctgcactacc gcatcgccct tgtcgtcaac     360
```

```
tacctgggcc actgcgtatc tgtggcagcc ctggtggccg ccttcctgct tttcctggcc    420
ctgcggagca ttcgctgtct gcggaatgtg attcactgga acctcatcac caccttatc    480
ctgcgaaatg tcatgtggtt cctgctgcag ctcgttgacc atgaagtgca cgagagcaat    540
gaggtctggt gccgctgcat caccaccatc ttcaactact cgtggtgac caacttcttc     600
tggatgtttg tggaaggctg ctacctgcac acggccattg tcatgaccta ctccactgag    660
cgcctgcgca agtgcctctt cctcttcatc ggatggtgca tccccttccc catcatcgtc    720
gcctgggcca tcgcaagct ctactatgag aatgaacagt gctggtttgg caaggagcct    780
ggcgacctgg tggactacat ctaccaaggc cccatcattc tcgtgctcct gatcaatttc    840
gtatttctgt tcaacatcgt caggatccta atgacaaagt tacgcgcgtc caccacatcc    900
gagacaatcc agtacaggaa ggcagtgaag gccaccctgg tgctcctgcc cctcctgggc    960
atcacctaca tgctcttctt cgtcaatccc ggggaggacg acctgtcaca gatcatgttc   1020
atctatttca actccttcct gcagtcgttc cagggttttct tcgtgtctgt cttctactgc   1080
ttcttcaatg agaggtgcg ctcagccgtg aggaagaggt ggcaccgctg gcaggaccat    1140
cactcccttc gagtccccat ggcccgggcc atgtccatcc ctacatcacc cacacggatc   1200
agcttccaca gcatcaagca gacggccgct gtgtgacccc tcggtcgccc acctgcacag   1260
ctcccctgtc ctcctccacc ttcttcctct gggttctctg tgctgggcag gctctcgtgg   1320
ggcaggagat gggaggggag agaccagctc tccagcctgg caggaaagag ggggtgcggc   1380
agccaagggg gactgcaagg gacagggatg agtgggggcc accaggctca gcgcaagagg   1440
aagcagaggg aattcacagg accccctgag aagagccagt cagatgtctg caggcatttg   1500
cccatcccag cctctctggc cagggcctta ctgggcccag agcagagaag gacctgtcca   1560
acacacacag ctatttatag tagcagacac agggctcccc tgccctactc atggagccag   1620
cagccaggca atggtgtggc cctgcactgg cccttggact ccacactcag tggtgccctg   1680
cagttgggtg ggttacgcca gcaaaggatc agtttggctg ccttatccca gggctgtcac   1740
ctagagaggc tcacttgtac cccacccgt tcctgtgtcc cctccccagc catcctcccg   1800
ccttggggc tccatgaagg atgcaggctt ccaggcctgg cttcctctct tgggagaccc    1860
cttctctgcc tagtccacag attaggcaat caaggaagac gccatcaggg aagccacatc   1920
cttagtcaac cagttgcatc gtgcggggca aaatgaggag cagaggcatg gaggagggag   1980
gcgtgggatg ggaatagcag aaccaccatg tcttcagtga ttgaaactca tacccattg    2040
cccttttgccc tccagtctcc ccttcagaaa catctctgct ctctgtgaaa taaaccatgc   2100
ctcttgg                                                             2107
```

<210> SEQ ID NO 4
<211> LENGTH: 411
<212> TYPE: PRT
<213> ORGANISM: Homo sapiens

<400> SEQUENCE: 4

Met Asp Ala Ala Leu Leu His Ser Leu Leu Glu Ala Asn Cys Ser Leu
 1               5                   10                  15

Ala Leu Ala Glu Glu Leu Leu Leu Asp Gly Trp Gly Pro Pro Leu Asp
                20                  25                  30

Pro Glu Gly Pro Tyr Ser Tyr Cys Asn Thr Thr Leu Asp Gln Ile Gly
            35                  40                  45

Thr Cys Trp Pro Arg Ser Ala Ala Gly Ala Leu Val Glu Arg Pro Cys
        50                  55                  60

```
Pro Glu Tyr Phe Asn Gly Val Lys Tyr Asn Thr Thr Arg Asn Ala Tyr
 65                  70                  75                  80

Arg Glu Cys Leu Glu Asn Gly Thr Trp Ala Ser Lys Ile Asn Tyr Ser
                 85                  90                  95

Gln Cys Glu Pro Ile Leu Asp Asp Lys Gln Arg Lys Tyr Asp Leu His
            100                 105                 110

Tyr Arg Ile Ala Leu Val Val Asn Tyr Leu Gly His Cys Val Ser Val
        115                 120                 125

Ala Ala Leu Val Ala Ala Phe Leu Leu Phe Leu Ala Leu Arg Ser Ile
    130                 135                 140

Arg Cys Leu Arg Asn Val Ile His Trp Asn Leu Ile Thr Thr Phe Ile
145                 150                 155                 160

Leu Arg Asn Val Met Trp Phe Leu Leu Gln Leu Val Asp His Glu Val
                165                 170                 175

His Glu Ser Asn Glu Val Trp Cys Arg Cys Ile Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu Arg Leu Arg Lys
    210                 215                 220

Cys Leu Phe Leu Phe Ile Gly Trp Cys Ile Pro Phe Pro Ile Ile Val
225                 230                 235                 240

Ala Trp Ala Ile Gly Lys Leu Tyr Tyr Glu Asn Glu Gln Cys Trp Phe
                245                 250                 255

Gly Lys Glu Pro Gly Asp Leu Val Asp Tyr Ile Tyr Gln Gly Pro Ile
            260                 265                 270

Ile Leu Val Leu Leu Ile Asn Phe Val Phe Leu Phe Asn Ile Val Arg
        275                 280                 285

Ile Leu Met Thr Lys Leu Arg Ala Ser Thr Thr Ser Glu Thr Ile Gln
    290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Met Phe Ile Tyr Phe Asn Ser Phe Leu Gln Ser Phe Gln Gly
            340                 345                 350

Phe Phe Val Ser Val Phe Tyr Cys Phe Phe Asn Gly Glu Val Arg Ser
        355                 360                 365

Ala Val Arg Lys Arg Trp His Arg Trp Gln Asp His His Ser Leu Arg
    370                 375                 380

Val Pro Met Ala Arg Ala Met Ser Ile Pro Thr Ser Pro Thr Arg Ile
385                 390                 395                 400

Ser Phe His Ser Ile Lys Gln Thr Ala Ala Val
                405                 410

<210> SEQ ID NO 5
<211> LENGTH: 41
<212> TYPE: PRT
<213> ORGANISM: Homo sapiens

<400> SEQUENCE: 5

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
```

```
                    20                  25                  30
Ser Asn Arg Lys Leu Met Glu Ile Ile
        35                  40

<210> SEQ ID NO 6
<211> LENGTH: 415
<212> TYPE: PRT
<213> ORGANISM: Homo sapiens

<400> SEQUENCE: 6

Met Gly Gly His Pro Gln Leu Arg Leu Val Lys Ala Leu Leu Leu Leu
 1               5                  10                  15

Gly Leu Asn Pro Val Ser Ala Ser Leu Gln Asp Gln His Cys Glu Ser
            20                  25                  30

Leu Ser Leu Ala Ser Asn Ile Ser Gly Leu Gln Cys Asn Ala Ser Val
        35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Met
                165                 170                 175

Ser Pro Glu Val His Gln Ser Asn Val Gly Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Ile Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350
```

-continued

```
Ser Phe Gln Gly Phe Phe Val Ser Val Phe Tyr Cys Phe Leu Asn Ser
        355                 360                 365

Glu Val Arg Ser Ala Ile Arg Lys Arg Trp His Arg Trp Gln Asp Lys
    370                 375                 380

His Ser Ile Arg Ala Arg Val Ala Arg Met Ser Ile Pro Thr Ser
385                 390                 395                 400

Pro Thr Arg Val Ser Phe His Ser Ile Lys Gln Ser Thr Ala Val
            405                 410                 415

<210> SEQ ID NO 7
<211> LENGTH: 415
<212> TYPE: PRT
<213> ORGANISM: Mus musculus

<400> SEQUENCE: 7

Met Gly Gln Arg Pro Gln Leu Arg Leu Val Lys Ala Leu Leu Leu
 1               5                  10                  15

Gly Leu Asn Pro Val Ser Thr Ser Leu Gln Asp Gln Cys Glu Ser
            20                  25                  30

Leu Ser Leu Ala Ser Asn Val Ser Gly Leu Gln Cys Asn Ala Ser Val
        35                  40                  45

Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Ile Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Val
                165                 170                 175

Ser Pro Glu Val His Gln Ser Asn Val Ala Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
    210                 215                 220

Arg Leu Arg Lys Trp Met Phe Val Cys Ile Gly Trp Gly Val Pro Phe
225                 230                 235                 240

Pro Ile Ile Val Ala Trp Ala Ile Gly Lys Leu Tyr Tyr Asp Asn Glu
                245                 250                 255

Lys Cys Trp Phe Gly Lys Arg Pro Gly Val Tyr Thr Asp Tyr Ile Tyr
            260                 265                 270

Gln Gly Pro Met Ile Leu Val Leu Leu Ile Asn Phe Ile Phe Leu Phe
        275                 280                 285

Asn Ile Val Arg Ile Leu Met Thr Lys Leu Arg Ala Ser Thr Thr Ser
    290                 295                 300

Glu Thr Ile Gln Tyr Arg Lys Ala Val Lys Ala Thr Leu Val Leu Leu
305                 310                 315                 320
```

```
Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
            340                 345                 350

Ser Phe Gln Gly Phe Phe Val Ser Val Phe Tyr Cys Phe Leu Asn Ser
        355                 360                 365

Glu Val Arg Ser Ala Ile Arg Lys Arg Trp Arg Trp Gln Asp Lys
    370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415

<210> SEQ ID NO 8
<211> LENGTH: 477
<212> TYPE: PRT
<213> ORGANISM: Homo sapiens

<400> SEQUENCE: 8

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
```

```
                275                 280                 285
Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Phe Ala Phe Val
        355                 360                 365

Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 9
<211> LENGTH: 463
<212> TYPE: PRT
<213> ORGANISM: Homo sapiens

<400> SEQUENCE: 9

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175
```

```
Asn Tyr Ile His Leu Asn Leu Phe Ala Ser Phe Ile Leu Arg Ala Leu
                180                 185                 190

Ser Val Phe Ile Lys Asp Ala Ala Leu Lys Trp Met Tyr Ser Thr Ala
            195                 200                 205

Ala Gln Gln His Gln Trp Asp Gly Leu Leu Ser Tyr Gln Asp Ser Leu
        210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Phe Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Gly Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
    370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
    450                 455                 460

<210> SEQ ID NO 10
<211> LENGTH: 593
<212> TYPE: PRT
<213> ORGANISM: Homo sapiens

<400> SEQUENCE: 10

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
                20                  25                  30

Thr Lys Glu Glu Gln Ile Phe Leu Leu His Arg Ala Gln Ala Gln Cys
            35                  40                  45

Glu Lys Arg Leu Lys Glu Val Leu Gln Arg Pro Ala Ser Ile Met Glu
        50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Glu Asp Lys Glu
                85                  90                  95
```

```
Ala Pro Thr Gly Ser Arg Tyr Arg Gly Arg Pro Cys Leu Pro Glu Trp
            100                 105                 110
Asp His Ile Leu Cys Trp Pro Leu Gly Ala Pro Gly Glu Val Val Ala
        115                 120                 125
Val Pro Cys Pro Asp Tyr Ile Tyr Asp Phe Asn His Lys Gly His Ala
    130                 135                 140
Tyr Arg Arg Cys Asp Arg Asn Gly Ser Trp Glu Leu Val Pro Gly His
145                 150                 155                 160
Asn Arg Thr Trp Ala Asn Tyr Ser Glu Cys Val Lys Phe Leu Thr Asn
                165                 170                 175
Glu Thr Arg Glu Arg Glu Val Phe Asp Arg Leu Gly Met Ile Tyr Thr
            180                 185                 190
Val Gly Tyr Ser Val Ser Leu Ala Ser Leu Thr Val Ala Val Leu Ile
        195                 200                 205
Leu Ala Tyr Phe Arg Arg Leu His Cys Thr Arg Asn Tyr Ile His Met
    210                 215                 220
His Leu Phe Leu Ser Phe Met Leu Arg Ala Val Ser Ile Phe Val Lys
225                 230                 235                 240
Asp Ala Val Leu Tyr Ser Gly Ala Thr Leu Asp Glu Ala Glu Arg Leu
                245                 250                 255
Thr Glu Glu Leu Arg Ala Ile Ala Gln Ala Pro Pro Pro Pro Ala
            260                 265                 270
Thr Ala Ala Gly Tyr Ala Gly Cys Arg Val Ala Val Thr Phe Phe
        275                 280                 285
Leu Tyr Phe Leu Ala Thr Asn Tyr Tyr Trp Ile Leu Val Glu Gly Leu
    290                 295                 300
Tyr Leu His Ser Leu Ile Phe Met Ala Phe Phe Ser Glu Lys Lys Tyr
305                 310                 315                 320
Leu Trp Gly Phe Thr Val Phe Gly Trp Gly Leu Pro Ala Val Phe Val
                325                 330                 335
Ala Val Trp Val Ser Val Arg Ala Thr Leu Ala Asn Thr Gly Cys Trp
            340                 345                 350
Asp Leu Ser Ser Gly Asn Lys Lys Trp Ile Ile Gln Val Pro Ile Leu
        355                 360                 365
Ala Ser Ile Val Leu Asn Phe Ile Leu Phe Ile Asn Ile Val Arg Val
    370                 375                 380
Leu Ala Thr Lys Leu Arg Glu Thr Asn Ala Gly Arg Cys Asp Thr Arg
385                 390                 395                 400
Gln Gln Tyr Arg Lys Leu Leu Lys Ser Thr Leu Val Leu Met Pro Leu
                405                 410                 415
Phe Gly Val His Tyr Ile Val Phe Met Ala Thr Pro Tyr Thr Glu Val
            420                 425                 430
Ser Gly Thr Leu Trp Gln Val Gln Met His Tyr Glu Met Leu Phe Asn
        435                 440                 445
Ser Phe Gln Gly Phe Phe Val Ala Ile Ile Tyr Cys Phe Cys Asn Gly
    450                 455                 460
Glu Val Gln Ala Glu Ile Lys Lys Ser Trp Ser Arg Trp Thr Leu Ala
465                 470                 475                 480
Leu Asp Phe Lys Arg Lys Ala Arg Ser Gly Ser Ser Ser Tyr Ser Tyr
                485                 490                 495
Gly Pro Met Val Ser His Thr Ser Val Thr Asn Val Gly Pro Arg Val
            500                 505                 510
```

```
Gly Leu Gly Leu Pro Leu Ser Pro Arg Leu Leu Pro Thr Ala Thr Thr
            515                 520                 525

Asn Gly His Pro Gln Leu Pro Gly His Ala Lys Pro Gly Thr Pro Ala
            530                 535                 540

Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
            580                 585                 590

Met

<210> SEQ ID NO 11
<211> LENGTH: 440
<212> TYPE: PRT
<213> ORGANISM: Homo sapiens

<400> SEQUENCE: 11

Met Arg Pro His Leu Ser Pro Pro Leu Gln Gln Leu Leu Leu Pro Val
 1               5                  10                  15

Leu Leu Ala Cys Ala Ala His Ser Thr Gly Ala Leu Pro Arg Leu Cys
             20                  25                  30

Asp Val Leu Gln Val Leu Trp Glu Glu Asp Gln Cys Leu Gln Glu
         35                  40                  45

Leu Ser Arg Glu Gln Thr Gly Asp Leu Gly Thr Glu Gln Pro Val Pro
     50                  55                  60

Gly Cys Glu Gly Met Trp Asp Asn Ile Ser Cys Trp Pro Ser Ser Val
 65                  70                  75                  80

Pro Gly Arg Met Val Glu Val Glu Cys Pro Arg Phe Leu Arg Met Leu
                 85                  90                  95

Thr Ser Arg Asn Gly Ser Leu Phe Arg Asn Cys Thr Gln Asp Gly Trp
            100                 105                 110

Ser Glu Thr Phe Pro Arg Pro Asn Leu Ala Cys Gly Val Asn Val Asn
        115                 120                 125

Asp Ser Ser Asn Glu Lys Arg His Ser Tyr Leu Leu Lys Leu Lys Val
    130                 135                 140

Met Tyr Thr Val Gly Tyr Ser Ser Ser Leu Val Met Leu Leu Val Ala
145                 150                 155                 160

Leu Gly Ile Leu Cys Ala Phe Arg Arg Leu His Cys Thr Arg Asn Tyr
                165                 170                 175

Ile His Met His Leu Phe Val Ser Phe Ile Leu Arg Ala Leu Ser Asn
            180                 185                 190

Phe Ile Lys Asp Ala Val Leu Phe Ser Ser Asp Asp Val Thr Tyr Cys
        195                 200                 205

Asp Pro His Arg Ala Gly Cys Lys Leu Val Met Val Leu Phe Gln Tyr
    210                 215                 220

Cys Ile Met Ala Asn Tyr Ser Trp Leu Leu Val Glu Gly Leu Tyr Leu
225                 230                 235                 240

His Thr Leu Leu Ala Ile Ser Phe Phe Ser Glu Arg Lys Tyr Leu Gln
                245                 250                 255

Gly Phe Val Ala Phe Gly Trp Gly Ser Pro Ala Ile Phe Val Ala Leu
            260                 265                 270

Trp Ala Ile Ala Arg His Phe Leu Glu Asp Val Gly Cys Trp Asp Ile
        275                 280                 285
```

```
Asn Ala Asn Ala Ser Ile Trp Trp Ile Ile Arg Gly Pro Val Ile Leu
    290                 295                 300

Ser Ile Leu Ile Asn Phe Ile Leu Phe Ile Asn Ile Leu Arg Ile Leu
305                 310                 315                 320

Met Arg Lys Leu Arg Thr Gln Glu Thr Arg Gly Asn Glu Val Ser His
            325                 330                 335

Tyr Lys Arg Leu Ala Arg Ser Thr Leu Leu Leu Ile Pro Leu Phe Gly
            340                 345                 350

Ile His Tyr Ile Val Phe Ala Phe Ser Pro Glu Asp Ala Met Glu Ile
            355                 360                 365

Gln Leu Phe Phe Glu Leu Ala Leu Gly Ser Phe Gln Gly Leu Val Val
    370                 375                 380

Ala Val Leu Tyr Cys Phe Leu Asn Gly Glu Val Gln Leu Glu Val Gln
385                 390                 395                 400

Lys Lys Trp Gln Gln Trp His Leu Arg Glu Phe Pro Leu His Pro Val
            405                 410                 415

Ala Ser Phe Ser Asn Ser Thr Lys Ala Ser His Leu Glu Gln Ser Gln
            420                 425                 430

Gly Thr Cys Arg Thr Ser Ile Ile
            435                 440

<210> SEQ ID NO 12
<211> LENGTH: 474
<212> TYPE: PRT
<213> ORGANISM: Homo sapiens

<400> SEQUENCE: 12

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                165                 170                 175

Gly Cys Gln Arg Val Thr Leu His Lys Asn Met Phe Leu Thr Tyr Ile
            180                 185                 190

Leu Asn Ser Met Ile Ile Ile Ile His Leu Val Glu Val Val Pro Asn
        195                 200                 205

Gly Glu Leu Val Arg Arg Asp Pro Val Ser Cys Lys Ile Leu His Phe
    210                 215                 220
```

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
            245                 250                 255

Gln Arg Leu Arg Trp Tyr Tyr Leu Leu Gly Trp Gly Phe Pro Leu Val
        260                 265                 270

Pro Thr Thr Ile His Ala Ile Thr Arg Ala Val Tyr Phe Asn Asp Asn
            275                 280                 285

Cys Trp Leu Ser Val Glu Thr His Leu Leu Tyr Ile Ile His Gly Pro
290                 295                 300

Val Met Ala Ala Leu Val Val Asn Phe Phe Leu Leu Asn Ile Val
305                 310                 315                 320

Arg Val Leu Val Thr Lys Met Arg Glu Thr His Glu Ala Glu Ser His
            325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
            355                 360                 365

Gly Lys Ile Tyr Asp Tyr Val Met His Ser Leu Ile His Phe Gln Gly
        370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
                405                 410                 415

Trp Gly Arg Arg Pro Ser Asn Arg Ser Ala Arg Ala Ala Ala Ala Ala
            420                 425                 430

Ala Glu Ala Gly Asp Ile Pro Ile Tyr Ile Cys His Gln Glu Leu Arg
            435                 440                 445

Asn Glu Pro Ala Asn Asn Gln Gly Glu Glu Ser Ala Glu Ile Ile Pro
        450                 455                 460

Leu Asn Ile Ile Glu Gln Glu Ser Ser Ala
465                 470

<210> SEQ ID NO 13
<211> LENGTH: 457
<212> TYPE: PRT
<213> ORGANISM: Homo sapiens

<400> SEQUENCE: 13

Met Arg Pro Pro Ser Pro Leu Pro Ala Arg Trp Leu Cys Val Leu Ala
1               5                   10                  15

Gly Ala Leu Ala Trp Ala Leu Gly Pro Ala Gly Gly Gln Ala Ala Arg
            20                  25                  30

Leu Gln Glu Glu Cys Asp Tyr Val Gln Met Ile Glu Val Gln His Lys
        35                  40                  45

Gln Cys Leu Glu Glu Ala Gln Leu Glu Asn Glu Thr Ile Gly Cys Ser
    50                  55                  60

Lys Met Trp Asp Asn Leu Thr Cys Trp Pro Ala Thr Pro Arg Gly Gln
65                  70                  75                  80

Val Val Val Leu Ala Cys Pro Leu Ile Phe Lys Leu Phe Ser Ser Ile
                85                  90                  95

Gln Gly Arg Asn Val Ser Arg Ser Cys Thr Asp Glu Gly Trp Thr His
            100                 105                 110

Leu Glu Pro Gly Pro Tyr Pro Ile Ala Cys Gly Leu Asp Asp Lys Ala

```
              115                 120                 125
Ala Ser Leu Asp Glu Gln Gln Thr Met Phe Tyr Gly Ser Val Lys Thr
    130                 135                 140

Gly Tyr Thr Ile Gly Tyr Gly Leu Ser Leu Ala Thr Leu Leu Val Ala
145                 150                 155                 160

Thr Ala Ile Leu Ser Leu Phe Arg Lys Leu His Cys Thr Arg Asn Tyr
                165                 170                 175

Ile His Met His Leu Phe Ile Ser Phe Ile Leu Arg Ala Ala Ala Val
            180                 185                 190

Phe Ile Lys Asp Leu Ala Leu Phe Asp Ser Gly Glu Ser Asp Gln Cys
        195                 200                 205

Ser Glu Gly Ser Val Gly Cys Lys Ala Ala Met Val Phe Phe Gln Tyr
    210                 215                 220

Cys Val Met Ala Asn Phe Phe Trp Leu Leu Val Glu Gly Leu Tyr Leu
225                 230                 235                 240

Tyr Thr Leu Leu Ala Val Ser Phe Phe Ser Glu Arg Lys Tyr Phe Trp
                245                 250                 255

Gly Tyr Ile Leu Ile Gly Trp Gly Val Pro Ser Thr Phe Thr Met Val
            260                 265                 270

Trp Thr Ile Ala Arg Ile His Phe Glu Asp Tyr Gly Cys Trp Asp Thr
        275                 280                 285

Ile Asn Ser Ser Leu Trp Trp Ile Ile Lys Gly Pro Ile Leu Thr Ser
    290                 295                 300

Ile Leu Val Asn Phe Ile Leu Phe Ile Cys Ile Ile Arg Ile Leu Leu
305                 310                 315                 320

Gln Lys Leu Arg Pro Pro Asp Ile Arg Lys Ser Asp Ser Ser Pro Tyr
                325                 330                 335

Ser Arg Leu Ala Arg Ser Thr Leu Leu Leu Ile Pro Leu Phe Gly Val
            340                 345                 350

His Tyr Ile Met Phe Ala Phe Phe Pro Asp Asn Phe Lys Pro Glu Val
        355                 360                 365

Lys Met Val Phe Glu Leu Val Val Gly Ser Phe Gln Gly Phe Val Val
    370                 375                 380

Ala Ile Leu Tyr Cys Phe Leu Asn Gly Glu Val Gln Ala Glu Leu Arg
385                 390                 395                 400

Arg Lys Trp Arg Arg Trp His Leu Gln Gly Val Leu Gly Trp Asn Pro
                405                 410                 415

Lys Tyr Arg His Pro Ser Gly Gly Ser Asn Gly Ala Thr Cys Ser Thr
            420                 425                 430

Gln Val Ser Met Leu Thr Arg Val Ser Pro Gly Ala Arg Arg Ser Ser
        435                 440                 445

Ser Phe Gln Ala Glu Val Ser Leu Val
    450                 455

<210> SEQ ID NO 14
<211> LENGTH: 353
<212> TYPE: PRT
<213> ORGANISM: Homo sapiens

<400> SEQUENCE: 14

Gly Glu Trp Val Thr Leu Pro Cys Pro Asp Phe Phe Ser His Phe Ser
  1               5                  10                  15

Ser Glu Ser Gly Ala Val Lys Arg Asp Cys Thr Ile Thr Gly Trp Ser
             20                  25                  30
```

```
Glu Pro Phe Pro Pro Tyr Pro Val Ala Cys Pro Val Pro Leu Glu Leu
            35                  40                  45

Leu Ala Glu Glu Ser Tyr Phe Ser Thr Val Lys Ile Ile Tyr Thr
 50                  55                  60

Val Gly His Ser Ile Ser Ile Val Ala Leu Phe Val Ala Ile Thr Ile
 65                  70                  75                  80

Leu Val Ala Leu Arg Arg Leu His Cys Pro Arg Asn Tyr Val His Thr
                85                  90                  95

Gln Leu Phe Thr Thr Phe Ile Leu Lys Ala Gly Arg Val Phe Leu Lys
                100                 105                 110

Asp Ala Ala Leu Phe His Ser Asp Thr Asp His Cys Ser Phe Ser
            115                 120                 125

Thr Val Leu Cys Lys Val Ser Val Ala Ala Ser His Phe Ala Thr Met
            130                 135                 140

Thr Asn Phe Ser Trp Leu Leu Ala Glu Ala Val Tyr Leu Asn Cys Leu
145                 150                 155                 160

Leu Ala Ser Thr Ser Pro Ser Ser Arg Arg Ala Phe Trp Trp Leu Val
                165                 170                 175

Leu Ala Gly Trp Gly Leu Pro Val Leu Phe Thr Gly Thr Trp Val Ser
                180                 185                 190

Cys Lys Leu Ala Phe Glu Asp Ile Ala Cys Trp Asp Leu Asp Asp Thr
                195                 200                 205

Ser Pro Tyr Trp Trp Ile Ile Lys Gly Pro Ile Val Leu Ser Val Gly
                210                 215                 220

Val Asn Phe Gly Leu Phe Leu Asn Ile Ile Arg Ile Leu Val Arg Lys
225                 230                 235                 240

Leu Glu Pro Ala Gln Gly Ser Leu His Thr Gln Ser Gln Tyr Trp Arg
                245                 250                 255

Leu Ser Lys Ser Thr Leu Phe Leu Ile Pro Leu Phe Gly Ile His Tyr
                260                 265                 270

Ile Ile Phe Asn Phe Leu Pro Asp Asn Ala Gly Leu Gly Ile Arg Leu
                275                 280                 285

Pro Leu Glu Leu Gly Leu Gly Ser Phe Gln Gly Phe Ile Val Ala Ile
                290                 295                 300

Leu Tyr Cys Phe Leu Asn Gln Glu Val Arg Thr Glu Ile Ser Arg Lys
305                 310                 315                 320

Trp His Gly His His Asp Pro Glu Leu Leu Pro Ala Trp Arg Thr Arg Ala
                325                 330                 335

Lys Trp Thr Thr Pro Ser Arg Ser Ala Ala Lys Val Leu Thr Ser Met
                340                 345                 350

Cys

<210> SEQ ID NO 15
<211> LENGTH: 466
<212> TYPE: PRT
<213> ORGANISM: Homo sapiens

<400> SEQUENCE: 15

Met Thr Thr Ser Pro Ile Leu Gln Leu Leu Arg Leu Ser Leu Cys
 1               5                  10                  15

Gly Leu Leu Leu Gln Arg Ala Glu Thr Gly Ser Lys Gly Gln Thr Ala
                20                  25                  30

Gly Glu Leu Tyr Gln Arg Trp Glu Arg Tyr Arg Arg Glu Cys Gln Glu
            35                  40                  45
```

-continued

```
Thr Leu Ala Ala Ala Glu Pro Pro Ser Gly Leu Ala Cys Asn Gly Ser
     50                  55                  60
Phe Asp Met Tyr Val Cys Trp Asp Tyr Ala Ala Pro Asn Ala Thr Ala
 65                  70                  75                  80
Arg Ala Ser Cys Pro Trp Tyr Leu Pro Trp His His His Val Ala Ala
                 85                  90                  95
Gly Phe Val Leu Arg Gln Cys Gly Ser Asp Gly Gln Trp Gly Leu Trp
                100                 105                 110
Arg Asp His Thr Gln Cys Glu Asn Pro Glu Lys Asn Glu Ala Phe Leu
                115                 120                 125
Asp Gln Arg Leu Ile Leu Glu Arg Leu Gln Val Met Tyr Thr Val Gly
130                 135                 140
Tyr Ser Leu Ser Leu Ala Thr Leu Leu Leu Ala Leu Leu Ile Leu Ser
145                 150                 155                 160
Leu Phe Arg Arg Leu His Cys Thr Arg Asn Tyr Ile His Ile Asn Leu
                165                 170                 175
Phe Thr Ser Phe Met Leu Arg Ala Ala Ala Ile Leu Ser Arg Asp Arg
                180                 185                 190
Leu Leu Pro Arg Pro Gly Pro Tyr Leu Gly Asp Gln Ala Leu Ala Leu
                195                 200                 205
Trp Asn Gln Ala Leu Ala Ala Cys Arg Thr Ala Gln Ile Val Thr Gln
210                 215                 220
Tyr Cys Val Gly Ala Asn Tyr Thr Trp Leu Leu Val Glu Gly Val Tyr
225                 230                 235                 240
Leu His Ser Leu Leu Val Leu Val Gly Gly Ser Glu Glu Gly His Phe
                245                 250                 255
Arg Tyr Tyr Leu Leu Leu Gly Trp Gly Ala Pro Ala Leu Phe Val Ile
                260                 265                 270
Pro Trp Val Ile Val Arg Tyr Leu Tyr Glu Asn Thr Gln Cys Trp Glu
                275                 280                 285
Arg Asn Glu Val Lys Ala Ile Trp Trp Ile Ile Arg Thr Pro Ile Leu
290                 295                 300
Met Thr Ile Leu Ile Asn Phe Leu Ile Phe Ile Arg Ile Leu Gly Ile
305                 310                 315                 320
Leu Leu Ser Lys Leu Arg Thr Arg Gln Met Arg Cys Arg Asp Tyr Arg
                325                 330                 335
Leu Arg Leu Ala Arg Ser Thr Leu Thr Leu Val Pro Leu Leu Gly Val
                340                 345                 350
His Glu Val Val Phe Ala Pro Val Thr Glu Glu Gln Ala Arg Gly Ala
                355                 360                 365
Leu Arg Phe Ala Lys Leu Gly Phe Glu Ile Phe Leu Ser Ser Phe Gln
370                 375                 380
Gly Phe Leu Val Ser Val Leu Tyr Cys Phe Ile Asn Lys Glu Val Gln
385                 390                 395                 400
Ser Glu Ile Arg Arg Gly Trp His His Cys Arg Leu Arg Arg Ser Leu
                405                 410                 415
Gly Glu Glu Gln Arg Gln Leu Pro Glu Arg Ala Phe Arg Ala Leu Pro
                420                 425                 430
Ser Gly Ser Gly Pro Gly Glu Val Pro Thr Ser Arg Gly Leu Ser Ser
                435                 440                 445
Gly Thr Leu Pro Gly Pro Gly Asn Glu Ala Ser Arg Glu Leu Glu Ser
450                 455                 460
Tyr Cys
```

```
<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 16

Gly Ser Gly Met Lys Glu Thr Ala Ala Ala Lys Phe Glu Arg Gln His
 1               5                  10                  15

Met Asp Ser Pro Asp Leu Gly Thr
            20

<210> SEQ ID NO 17
<211> LENGTH: 81
<212> TYPE: PRT
<213> ORGANISM: Mus musculus

<400> SEQUENCE: 17

Thr Leu Leu Glu Gln Tyr Cys His Arg Thr Thr Ile Gly Asn Phe Ser
 1               5                  10                  15

Gly Pro Tyr Thr Tyr Cys Asn Thr Thr Leu Asp Gln Ile Gly Thr Cys
                20                  25                  30

Trp Pro Gln Ser Ala Pro Gly Ala Leu Val Glu Arg Pro Cys Pro Glu
            35                  40                  45

Tyr Phe Asn Gly Ile Lys Tyr Asn Thr Thr Arg Asn Ala Tyr Arg Glu
    50                  55                  60

Cys Leu Glu Asn Gly Thr Trp Ala Ser Arg Val Asn Tyr Ser His Cys
65                  70                  75                  80

Glu

<210> SEQ ID NO 18
<211> LENGTH: 79
<212> TYPE: PRT
<213> ORGANISM: Homo sapiens

<400> SEQUENCE: 18

Ser Leu Gln Asp Gln His Cys Glu Ser Leu Ser Leu Ala Ser Asn Ile
 1               5                  10                  15

Ser Gly Leu Gln Cys Asn Ala Ser Asp Leu Ile Gly Thr Cys Trp Pro
                20                  25                  30

Arg Ser Pro Ala Gly Gln Leu Val Val Arg Pro Cys Pro Ala Phe Phe
            35                  40                  45

Tyr Gly Val Arg Tyr Asn Thr Thr Asn Asn Gly Tyr Arg Glu Cys Leu
    50                  55                  60

Ala Asn Gly Ser Trp Ala Ala Arg Val Asn Tyr Ser Glu Cys Gln
65                  70                  75

<210> SEQ ID NO 19
<211> LENGTH: 80
<212> TYPE: PRT
<213> ORGANISM: Mus musculus

<400> SEQUENCE: 19

Ser Leu Gln Asp Gln Gln Cys Glu Ser Leu Ser Leu Ala Ser Asn Val
 1               5                  10                  15

Ser Gly Leu Gln Cys Asn Ala Ser Val Asp Leu Ile Gly Thr Cys Trp
```

```
                    20                  25                  30

Pro Arg Ser Pro Ala Gly Gln Leu Val Val Arg Pro Cys Pro Ala Phe
        35                  40                  45

Phe Tyr Gly Val Arg Tyr Asn Thr Thr Asn Gly Tyr Arg Glu Cys
    50                  55                  60

Leu Ala Asn Gly Ser Trp Ala Ala Arg Val Asn Tyr Ser Glu Cys Gln
65                  70                  75                  80

<210> SEQ ID NO 20
<211> LENGTH: 80
<212> TYPE: PRT
<213> ORGANISM: Artificial Sequence
<220> FEATURE:
<223> OTHER INFORMATION: Synthetic peptide

<400> SEQUENCE: 20

Ser Leu Gln Asp Gln His Cys Glu Ser Leu Ser Pro Thr Ser Asn Val
1               5                   10                  15

Ser Gly Leu Gln Cys Asn Ala Ser Val Asp Leu Ile Gly Thr Cys Trp
            20                  25                  30

Pro Arg Ser Pro Ala Gly Gln Leu Val Val Arg Pro Cys Pro Ala Phe
        35                  40                  45

Phe Tyr Gly Val Arg Tyr Asn Thr Thr Asn Gly Tyr Arg Glu Cys
    50                  55                  60

Leu Ala Asn Gly Ser Trp Ala Ala Arg Val Asn Tyr Ser Glu Cys Gln
65                  70                  75                  80

<210> SEQ ID NO 21
<211> LENGTH: 80
<212> TYPE: PRT
<213> ORGANISM: Rattus norvegicus

<400> SEQUENCE: 21

Ser Leu Gln Asp Gln Arg Cys Glu Asn Leu Ser Leu Thr Ser Asn Val
1               5                   10                  15

Ser Gly Leu Gln Cys Asn Ala Ser Val Asp Leu Ile Gly Thr Cys Trp
            20                  25                  30

Pro Arg Ser Pro Ala Gly Gln Leu Val Val Arg Pro Cys Pro Ala Phe
        35                  40                  45

Phe Tyr Gly Val Arg Tyr Asn Thr Thr Asn Gly Tyr Arg Glu Cys
    50                  55                  60

Leu Ala Asn Gly Ser Trp Ala Ala Arg Val Asn Tyr Ser Glu Cys Gln
65                  70                  75                  80

<210> SEQ ID NO 22
<211> LENGTH: 80
<212> TYPE: PRT
<213> ORGANISM: Ovis aries

<400> SEQUENCE: 22

Ser Leu Gln Asp Gln His Cys Glu Ser Leu Ser Leu Ala Ser Asn Val
1               5                   10                  15

Ser Gly Leu Gln Cys Asn Ala Ser Val Asp Leu Asn Gly Thr Cys Trp
            20                  25                  30

Pro Gln Ser Pro Ala Gly Gln Leu Val Val Arg Pro Cys Leu Val Phe
        35                  40                  45

Phe Tyr Gly Val Arg Tyr Asn Tyr Tyr Ser Asn Gly Tyr Arg Val Cys
    50                  55                  60
```

```
Leu Ala Asn Gly Thr Trp Ala Ala Arg Val Asn His Ser Glu Cys Gln
 65                  70                  75                  80
```

<210> SEQ ID NO 23
<211> LENGTH: 80
<212> TYPE: PRT
<213> ORGANISM: Gallus gallus

<400> SEQUENCE: 23

```
Ser Ile Gln Glu Gln Tyr Cys Glu Ser Leu Leu Pro Thr Thr Asn His
  1               5                  10                  15

Thr Gly Pro Gln Cys Asn Ala Ser Val Asp Leu Ile Gly Thr Cys Trp
             20                  25                  30

Pro Arg Ser Ala Val Gly Gln Leu Val Ala Arg Pro Cys Pro Glu Tyr
         35                  40                  45

Phe Tyr Gly Val Arg Tyr Asn Thr Thr Asn Gly Tyr Arg Glu Cys
     50                  55                  60

Leu Ala Asn Gly Ser Trp Ala Ala Arg Val Asn Tyr Ser Gln Cys Gln
 65                  70                  75                  80
```

<210> SEQ ID NO 24
<211> LENGTH: 85
<212> TYPE: PRT
<213> ORGANISM: Artificial Sequence
<220> FEATURE:
<223> OTHER INFORMATION: Synthetic peptide

<400> SEQUENCE: 24

```
Ala Thr Ala Glu Leu Thr Cys Asp Thr Leu Leu Asn Ala Thr Gly Thr
  1               5                  10                  15

Ser Ser Ser Asn Ala Thr Gly Leu Phe Cys Asn Ile Ser Ile Asp Gly
             20                  25                  30

Ile Phe Thr Cys Trp Pro Arg Ser Asn Ala Phe Glu Ile Val Ser Arg
         35                  40                  45

Pro Cys Pro Glu Thr Phe Leu Gly Val Arg Tyr Asn Thr Thr Asn Asn
     50                  55                  60

Val Tyr Arg Glu Cys Leu Ala Asn Gly Thr Trp Ala Lys Lys Gly Asn
 65                  70                  75                  80

Tyr Ser Gln Cys Gln
             85
```

<210> SEQ ID NO 25
<211> LENGTH: 85
<212> TYPE: PRT
<213> ORGANISM: Oncorhynchus keta

<400> SEQUENCE: 25

```
Thr Thr Ala Asp Leu Thr Cys Asp Thr Leu Leu Asn Leu Thr Leu Thr
  1               5                  10                  15

Pro Ser Asn Val Thr Ala Gly Leu Phe Cys Asn Met Ser Ile Asp Pro
             20                  25                  30

Ile Gly Thr Cys Trp Pro Lys Ser Thr Ala Gly Glu Trp Val Leu Arg
         35                  40                  45

Pro Cys Pro Glu Met Phe Tyr Gly Val Lys Tyr Asn Thr Thr Asn Asn
     50                  55                  60

Val Tyr Arg Glu Cys Leu Ser Asn Gly Ser Trp Ala Val Lys Gly Asn
 65                  70                  75                  80

Tyr Thr Gln Cys Gln
             85
```

```
<210> SEQ ID NO 26
<211> LENGTH: 85
<212> TYPE: PRT
<213> ORGANISM: Fugu rubripes

<400> SEQUENCE: 26

Ser Leu Ala Asn Leu Thr Cys Glu Ala Leu Leu Met Ser Leu Met Asn
 1               5                  10                  15

Ala Thr Ser Thr Cys Ser Gly Leu Tyr Cys Glu Thr Ser Ile Asp Gly
            20                  25                  30

Ile Gly Thr Cys Trp Pro Arg Ser Ala Ala Gly His Met Val Ser Arg
        35                  40                  45

Pro Cys Pro Glu Met Phe Tyr Gly Val Arg Tyr Asn Thr Thr Asn Asn
    50                  55                  60

Val Tyr Arg Lys Cys Leu Ala Asn Gly Thr Trp Ala Leu Lys Gly Asn
65                  70                  75                  80

Tyr Ser Met Cys Lys
                85

<210> SEQ ID NO 27
<211> LENGTH: 79
<212> TYPE: PRT
<213> ORGANISM: Xenopus laevis

<400> SEQUENCE: 27

Ser Leu Gln Asp Gln Cys Glu Thr Leu Gln His Asn Ser Asn Phe Thr
 1               5                  10                  15

Gly Leu Ala Cys Asn Ala Ser Ile Asp Met Ile Gly Thr Cys Trp Pro
            20                  25                  30

Ser Thr Ala Ala Gly Gln Met Val Ala Arg Pro Cys Pro Glu Tyr Phe
        35                  40                  45

His Gly Val Gln Tyr Asn Thr Thr Gly Asn Val Tyr Arg Glu Cys His
    50                  55                  60

Leu Asn Gly Ser Trp Ala Gly Arg Gly Asp Tyr Ala Gln Cys Gln
65                  70                  75

<210> SEQ ID NO 28
<211> LENGTH: 85
<212> TYPE: PRT
<213> ORGANISM: Artificial Sequence
<220> FEATURE:
<223> OTHER INFORMATION: Synthetic peptide

<400> SEQUENCE: 28

Ser Leu Leu Glu Ala Asn Cys Ser Leu Glu Leu Ala Glu Glu Leu Leu
 1               5                  10                  15

Leu Asp Gly Glu Gly Pro Tyr Ser Tyr Cys Asn Thr Thr Leu Asp Gln
            20                  25                  30

Ile Gly Thr Cys Trp Pro Arg Ser Ala Gly Ala Leu Val Glu Arg
        35                  40                  45

Pro Cys Pro Glu Tyr Phe Asn Gly Val Lys Tyr Asn Ala Thr Arg Asn
    50                  55                  60

Ala Tyr Arg Glu Cys Leu Glu Asn Gly Thr Trp Ala Ser Arg Ile Asn
65                  70                  75                  80

Tyr Ser Gln Cys Glu
                85
```

<210> SEQ ID NO 29
<211> LENGTH: 85
<212> TYPE: PRT
<213> ORGANISM: Homo sapiens

<400> SEQUENCE: 29

Ser Leu Leu Glu Ala Asn Cys Ser Leu Ala Leu Ala Glu Glu Leu Leu
 1               5                  10                  15

Leu Asp Gly Glu Gly Pro Tyr Ser Tyr Cys Asn Thr Thr Leu Asp Gln
                20                  25                  30

Ile Gly Thr Cys Trp Pro Arg Ser Ala Ala Gly Ala Leu Val Glu Arg
            35                  40                  45

Pro Cys Pro Glu Tyr Phe Asn Gly Val Lys Tyr Asn Thr Thr Arg Asn
        50                  55                  60

Ala Tyr Arg Glu Cys Leu Glu Asn Gly Thr Trp Ala Ser Lys Ile Asn
65                  70                  75                  80

Tyr Ser Gln Cys Glu
                85

<210> SEQ ID NO 30
<211> LENGTH: 85
<212> TYPE: PRT
<213> ORGANISM: Rattus norvegicus

<400> SEQUENCE: 30

Ser Leu Leu Glu Ala Asn Cys Ser Leu Ala Leu Ala Glu Glu Leu Leu
 1               5                  10                  15

Leu Asp Gly Glu Gly Pro Tyr Ser Tyr Cys Asn Thr Thr Leu Asp Gln
                20                  25                  30

Ile Gly Thr Cys Trp Pro Gln Ser Ala Pro Gly Ala Leu Val Glu Arg
            35                  40                  45

Pro Cys Pro Glu Tyr Phe Asn Gly Ile Lys Tyr Asn Thr Thr Arg Asn
        50                  55                  60

Ala Tyr Arg Glu Cys Leu Glu Asn Gly Thr Trp Ala Ser Arg Ile Asn
65                  70                  75                  80

Tyr Ser His Cys Glu
                85

<210> SEQ ID NO 31
<211> LENGTH: 85
<212> TYPE: PRT
<213> ORGANISM: Oncorhynchus keta

<400> SEQUENCE: 31

Glu Phe Gly Asp Pro Asn Cys Ser Val Met Asp Ser Phe Gln Asp Ser
 1               5                  10                  15

Phe Tyr Glu Asn Ala Ser Gly Leu Tyr Cys Asn Ala Thr Thr Asp Glu
                20                  25                  30

Ile Gly Thr Cys Trp Pro Lys Ser Asn Thr Gly Arg Met Val Glu Arg
            35                  40                  45

Pro Cys Pro Glu Tyr Ile Asn Gly Val Lys Tyr Asn Thr Thr Arg Ser
        50                  55                  60

Ala Tyr Arg Glu Cys Ile Asp Asn Gly Thr Trp Ala Leu Lys Ser Asn
65                  70                  75                  80

Tyr Ser Ser Cys Glu
                85

<210> SEQ ID NO 32

```
<211> LENGTH: 85
<212> TYPE: PRT
<213> ORGANISM: Xenopus laevis

<400> SEQUENCE: 32

Asp Glu Phe Asp Ala Asn Cys Ser Leu Leu Asp Ala Phe Gln Asp Ser
 1               5                  10                  15

Phe Leu His Ser Glu Ser Gly Pro Tyr Cys Ser Ala Thr Ile Asp Gln
            20                  25                  30

Ile Gly Thr Cys Trp Pro Arg Ser Leu Ala Gly Glu Leu Val Glu Arg
        35                  40                  45

Pro Cys Pro Asp Ser Phe Asn Gly Ile Arg Tyr Asn Thr Thr Arg Asn
    50                  55                  60

Val Tyr Arg Glu Cys Phe Glu Asn Gly Thr Trp Ala Ser Trp Met Asn
 65                  70                  75                  80

Tyr Ser Gln Cys Val
                85

<210> SEQ ID NO 33
<211> LENGTH: 86
<212> TYPE: PRT
<213> ORGANISM: Artificial Sequence
<220> FEATURE:
<223> OTHER INFORMATION: Synthetic peptide

<400> SEQUENCE: 33

Leu Ser Val Glu Val Asn Cys Ser Leu Ala Asp Ala Phe Gly Asp Pro
 1               5                  10                  15

Ala Tyr Gly Asn Ala Ser Ala Leu Tyr Cys Asn Ala Thr Ala Asp Glu
            20                  25                  30

Ile Gly Thr Cys Trp Pro Arg Ser Gly Ala Gly Arg Val Val Ala Arg
        35                  40                  45

Pro Cys Pro Asp Phe Ile Asn Gly Val Lys Tyr Asn Ser Thr Arg Ala
    50                  55                  60

Ser Ala Tyr Arg Glu Cys Leu Glu Asn Gly Thr Trp Ala Phe Lys Ile
 65                  70                  75                  80

Asn Tyr Ser Ser Cys Glu
                85

<210> SEQ ID NO 34
<211> LENGTH: 81
<212> TYPE: PRT
<213> ORGANISM: Mus musculus

<400> SEQUENCE: 34

Thr Leu Leu Glu Gln Tyr Cys His Arg Thr Thr Ile Gly Asn Phe Ser
 1               5                  10                  15

Gly Pro Tyr Thr Tyr Cys Asn Thr Thr Leu Asp Gln Ile Gly Thr Cys
            20                  25                  30

Trp Pro Gln Ser Ala Pro Gly Ala Leu Val Glu Arg Pro Cys Pro Glu
        35                  40                  45

Tyr Phe Asn Gly Ile Lys Tyr Asn Thr Thr Arg Asn Ala Tyr Arg Glu
    50                  55                  60

Cys Leu Glu Asn Gly Thr Trp Ala Ser Arg Val Asn Tyr Ser His Cys
 65                  70                  75                  80

Glu

<210> SEQ ID NO 35
```

<211> LENGTH: 83
<212> TYPE: PRT
<213> ORGANISM: Homo sapiens

<400> SEQUENCE: 35

Gln Met Ile Glu Val Gln His Lys Gln Cys Leu Glu Glu Ala Gln Leu
1               5                   10                  15

Glu Asn Glu Thr Ile Gly Cys Ser Lys Met Trp Asp Asn Leu Thr Cys
            20                  25                  30

Trp Pro Ala Thr Pro Arg Gly Gln Val Val Leu Ala Cys Pro Leu
        35                  40                  45

Ile Phe Lys Leu Phe Ser Ser Ile Gln Gly Arg Asn Val Ser Arg Ser
50                  55                  60

Cys Thr Asp Glu Gly Trp Thr His Leu Glu Pro Gly Pro Tyr Pro Ile
65                  70                  75                  80

Ala Cys Gly

<210> SEQ ID NO 36
<211> LENGTH: 82
<212> TYPE: PRT
<213> ORGANISM: Homo sapiens

<400> SEQUENCE: 36

Thr Gln Leu Arg Glu Asp Glu Ser Ala Cys Leu Gln Ala Ala Glu Glu
1               5                   10                  15

Met Pro Asn Thr Thr Leu Gly Cys Pro Ala Thr Trp Asp Gly Leu Leu
            20                  25                  30

Cys Trp Pro Thr Ala Gly Ser Gly Glu Trp Val Thr Leu Pro Cys Pro
        35                  40                  45

Asp Phe Phe Ser His Phe Ser Ser Glu Ser Gly Ala Val Lys Arg Asp
50                  55                  60

Cys Thr Ile Thr Gly Trp Ser Glu Pro Phe Pro Pro Tyr Pro Val Ala
65                  70                  75                  80

Cys Pro

<210> SEQ ID NO 37
<211> LENGTH: 88
<212> TYPE: PRT
<213> ORGANISM: Homo sapiens

<400> SEQUENCE: 37

Arg Glu Tyr Arg Arg Gln Cys Gln Arg Ser Leu Thr Glu Asp Pro Pro
1               5                   10                  15

Pro Ala Thr Asp Leu Phe Cys Asn Arg Thr Phe Asp Glu Tyr Ala Cys
            20                  25                  30

Trp Pro Asp Gly Glu Pro Gly Ser Phe Val Asn Val Ser Cys Pro Trp
        35                  40                  45

Tyr Leu Pro Trp Ala Ser Ser Val Pro Gln Gly His Val Tyr Arg Phe
50                  55                  60

Cys Thr Ala Glu Gly Leu Trp Leu Gln Lys Asp Asn Ser Ser Leu Pro
65                  70                  75                  80

Trp Arg Asp Leu Ser Glu Cys Glu
                85

<210> SEQ ID NO 38
<211> LENGTH: 87
<212> TYPE: PRT
<213> ORGANISM: Homo sapiens -continued

<400> SEQUENCE: 38

```
Leu Val Leu Lys Ala Lys Val Gln Cys Glu Leu Asn Ile Thr Ala Gln
  1               5                  10                  15

Leu Gln Glu Gly Glu Gly Asn Cys Phe Pro Glu Trp Asp Gly Leu Ile
             20                  25                  30

Cys Trp Pro Arg Gly Thr Val Gly Lys Ile Ser Ala Val Pro Cys Pro
         35                  40                  45

Pro Tyr Ile Tyr Asp Phe Asn His Lys Gly Val Ala Phe Arg His Cys
     50                  55                  60

Asn Pro Asn Gly Thr Trp Asp Phe Met His Ser Leu Asn Lys Thr Trp
 65                  70                  75                  80

Ala Asn Tyr Ser Asp Cys Leu
                 85
```

<210> SEQ ID NO 39
<211> LENGTH: 119
<212> TYPE: PRT
<213> ORGANISM: Artificial Sequence
<220> FEATURE:
<223> OTHER INFORMATION: Synthetic peptide

<400> SEQUENCE: 39

```
Gly Ser Gly Met Lys Glu Thr Ala Ala Ala Lys Phe Glu Arg Gln His
  1               5                  10                  15

Met Asp Ser Pro Asp Leu Gly Thr Thr Leu Leu Glu Gln Tyr Cys His
             20                  25                  30

Arg Thr Thr Ile Gly Asn Phe Ser Gly Pro Tyr Thr Tyr Cys Asn Thr
         35                  40                  45

Thr Leu Asp Gln Ile Gly Thr Cys Trp Pro Gln Ser Ala Pro Gly Ala
     50                  55                  60

Leu Val Glu Arg Pro Cys Pro Glu Tyr Phe Asn Gly Ile Lys Tyr Asn
 65                  70                  75                  80

Thr Thr Arg Asn Ala Tyr Arg Glu Cys Leu Glu Asn Gly Thr Trp Ala
             85                  90                  95

Ser Arg Val Asn Tyr Ser His Cys Glu Pro Ile Leu Asp Asp Lys Gln
            100                 105                 110

Arg Lys Tyr Asp Leu His Tyr
            115
```

STRUCTURE-BASED MODULATORS OF B1 G-PROTEIN COUPLED RECEPTORS

This application claims priority to U.S. Provisional Patent Application Ser. No. 60/599,936 filed Aug. 9, 2004, which is incorporated herein by reference in its entirety.

The government owns rights in the present invention pursuant to NIH grant numbers DK26741 and DK059953.

TECHNICAL FIELD

The field of the invention relates to molecular biology and biophysics, particularly protein structure determination and uses thereof. Certain aspects of the invention relate to rational drug design based on structural determinations of extracellular domains of B1 G-protein coupled receptors (GPCRs), particularly ligand binding domains.

BACKGROUND OF THE INVENTION

Many medically significant biological processes are mediated by proteins participating in signal transduction pathways involving G-proteins and second messengers such as cAMP. The membrane protein gene superfamily of G-protein coupled receptors (GPCRs) includes a wide range of biologically active receptors, such as hormone, viral, growth factor, and neuro-receptors. GPCRs have been characterized as having seven putative transmembrane (TM) domains (designated TM1, TM2, TM3, TM4, TM5, TM6, and TM7), which are believed to represent transmembrane α-helices connected by extracellular or cytoplasmic loops. Most G-protein coupled receptors have single conserved cysteine residues in each of the first two extracellular loops that form disulfide bonds believed to stabilize the functional protein structure. G-protein coupled receptors may be coupled intracellularly with heterotrimeric G-proteins and various intracellular enzymes, ion channels, and transporters. Different G-protein α-subunits preferentially stimulate particular effectors to modulate various biological functions in a cell.

One important subfamily of the GPCRs is the corticotropin-releasing factor receptors (CRFR), also known as corticotropin-releasing hormone receptors (CRHR). Corticotropin-releasing factor (CRF) (corticotropin-releasing hormone) is a 41-residue hypothalamic peptide (SEQ ID NO:5) which stimulates the secretion and biosynthesis of pituitary ACTH. Secretion of ACTH leads to increased adrenal glucocorticoid production. CRF was isolated and characterized based on its role in the hypothalamic-pituitary-adrenal axis (HPA). More recently, however, it has been found to be distributed broadly within the central nervous system (CNS), as well as in extra-neural tissues such as the adrenal glands and testes, where it may also act as a paracrine regulator or neurotransmitter.

A considerable body of evidence suggests that peptides of the CRF family, e.g., CRF(1), (frog) sauvagine, (fish) urotensin, and the mammalian urocortins 1, 2 and 3 (Ucn 1,2 and 3), play biologically diverse roles by activating CRF receptors. The CRF receptors, encoded by two distinct receptor genes, exist in multiple splice variant forms and display both species and tissue differential expression. Studies with transgenic mice expressing functionally disabled receptors, have underscored the importance of CRFR1 in regulating the hypothalamic-pituitary-adrenal axis in its response to stress. CRFR2 plays an important role in modulating the central nervous system response to stress as well as a unique role in cardiac function and pancreatic hormone release.

The CRF receptors belong to the B1 subfamily of G-protein coupled receptors (GPCRs). The GPCRs present a large variety of different conformations in their extracellular domains in order to cover their different functions. Indeed, a major ligand-binding site on both CRFR1 and CRFR2 is the N-terminal extracellular domain ($ECD_1$). The inhibitory binding constants for a bacterially expressed soluble protein fragment, $ECD_1$-CRFR2β, (comprising amino acids 39-133 of mCRFR2β) are: 11.8 (7.4-18.9) nM, 53.7 (18.7-154) nM and 21.1 (15.3-29.0) nM for Ucn 1, Ucn 2, and astressin, respectively. There remains a need for additional compositions and methods for identifying and assessing agonist and antagonist of B1 GPCRs, particular corticotropin releasing factor receptors.

SUMMARY OF THE INVENTION

Certain aspects of the invention provide methods for identifying modulators (antagonist or agonist) of B1 GPCRs, particulartly CRFRs including, but not limted to CRFR1 and CRFR2. Modulators of GPCRs may be used as therapeutic agents for the treatment of a wide range of disorders or illnesses including endocrine, psychiatric, and neurologic disorders or illnesses. One aspect of the invention provides a three-dimensional model (representation) of the extracellular domain ($ECD_1$) of CRFR2 that can be used as a basis for rational drug design. The method, in preferred aspects, involves analyzing the structure of the extracellular domain of CRFR2 or other B1 GPCRs, designing a candidate modulating agent to fit into or bind the ligand-interacting or protein-protein interaction sites of the extracellular domain and testing or assessing the candidate modulating agent for activity. Other B1 GPCR family members may be modeled using the atomic coordinates of the ECD1 of CRFR2 appropriately modified in relation to the amino acid sequence of the other B1 GPCR.

In certain embodiments of the invention, it is contemplated that the methods described herein are applicable to CRFR2, including α,β,γ splice variants, as well as CRFR1 (SEQ ID NO:6, SEQ ID NO:7). In other embodiments of the invention, the methods are applicable to modeling ECD1 of other members of the B1 subfamily of GPCRs. The B1 subfamily of GPCRs includes, but is not limited to receptors for glucagon (SEQ ID NO:8); glucagon like peptide (SEQ ID NO:9); parathyroid hormone (SEQ ID NO:10); secretin (SEQ ID NO:11); calcitonin (SEQ ID NO:12); vasoactive intestinal peptide (SEQ ID NO:13); growth hormone releasing factor (SEQ ID NO:14); pituitary adenylate cyclase-activating polypeptide (SEQ ID NO:15); and glucose-dependent insulinotropic polypeptide. It is further contemplated that both transmembrane and soluble forms of the receptors are appropriate for use in the method of the present invention. Certain aspects of the invnetion contemplate the use of soluble GPCR or their fragments or domains.

In still further aspects, the structure of the extracellular domain of CRFR2 comprises a three-dimensional nuclear magnetic resonance (NMR) structure as set forth in PDB ID NO:1U34, which is incorporated herein by reference in its entirety. Also, a set of atomic coordinates representative of a conformer of CRFR2 is provided in Table 3. A text version of the PDB file is provided as Table 4 that is 599 pages long and is submitted with the application on compact disk, which is incorporated herein by reference. The result of the NMR analysis of the extracellular domain of CRFR2 is a set of estimates of distances between specific pairs of atoms, called "constraints." The result is an ensemble of models, rather than a single structure. Often the positions of atoms in the different models are averaged, and the average model is then adjusted to obey normal bond distances and angles ("restrained minimization").

"CRFR2 receptors" as utilized herein refers to receptor proteins that specifically bind corticotropin-releasing factor and other proteins such as urotensin I and urocortin I. U.S. Pat. No. 5,786,203, incorporated herein by reference in its entirety, describes sequences and nucleic acid constructs that may be used in the present invention. In certain embodiments of the invention, it is contemplated that the mouse CRFR2 (GenBank Accesion No: NM 009953 SEQ ID NO:1 and NP 034083 SEQ ID NO:2) receptor is used for molecular modeling to design antagonists or agonists. In certain embodiments, the extracellular domain comprises amino acids 39-133 of SEQ ID NO:2. In other embodiments of the invention, it is contemplated that the human CRFR2 (GenBank Accesion No: NM 001883 (SEQ ID NO:3) and NP 001874 (SEQ ID NO:4)) is used for molecular modeling to design antagonists or selective agonists. In further embodiments, the extracellular domain comprises amino acids 8-102 of SEQ ID NO:4. One with skill in the art realizes that the extracellular domain of both human and mouse CRFR2 may be either the entire N-terminal extracellular domain, or functional (ligand-binding) fragments thereof.

In certain embodiments, it is contemplated that candidate agents are designed to interact with amino acids 67, 68, 69, 90, 91, 92, 93, 102, 103, 112, 113, 114, 115, 116 or combinations thereof, of SEQ ID NO:2 or analogous amino acids of other B1 GPCRs. In specific embodiments, candidate agents are designed to interact with amino acids 67, 92, and 112 of SEQ ID NO:2 or analogous amino acids of other B1 GPCRs. In one embodiment if the present invention, a modulator (antagonist or agonist) binds in proximity to one or more amino acids in the extracellular domain of CRFR2 or in analogous regions of other receptors. In a preferred embodiment of the invention, a modulator (antagonist or agonist) binds in proximity to a short consensus repeat domain of the extracellular domain of a GPCR.

The present invention also provides methods for improving known modulators of GPCRs by studying or modeling their structure as bound to the extracellular domain of the receptor, and improving their design within the parameters indicated by the structure analysis. By analyzing the structure, it is contemplated that the antagonist or agonist can be modified in order to bind a GPCR with higher affinity. Methods for screening candidate agents include contacting or modeling the agent with the extracellular domain of a GPCR, including but not limited to CRFR2; and analyzing the ability of the candidate agent to bind to the extracellular domain. For example, the binding affinity of candidate agents for the extracellular domain of CRFR2 will be determined. As used herein, "binding affinity" refers to the strength of an interaction between two entities, such as a protein-protein or protein-drug interaction. Binding affinity is referred to as the $K_a$, or association constant, which describes the likelihood of the two separate entities to be in the bound state. The binding affinity measures the ability of the interaction to minimize the free energy of the system, which comprises the interacting species, as well as the solvent. For example, the unbound and bound portions may be separated from one another through adsorption, precipitation, gel filtration, dialysis, or centrifugation. The measurement of the concentrations of bound and unbound portions is accomplished, for example, by measuring radioactivity or fluorescence.

Specific embodiments of the invention include performing computer analysis, i.e., using computer readable medium providing instructions for modeling an agent having the ability to bind the extracellular domain of a GPCR. In one embodiment, the computer readable medium may include computer-instructions for analyizng the coordinate representation of an extracellular domain of, for example, B1 GPCR. The analysis of the extracellular domain enables one with skill in the art to design candidate agents for modulating the activity of the receptor or other protein-protein interactions. An "agent" or "candidate agent" as identified by the methods of the present invention may include, but is not limited to a protein, polypeptide, peptide, peptidomimetic, nucleic acid (including DNA or RNA), small molecule, or compound. In a specific embodiment of the invention, the agent is a peptide or a peptidomimetic. In another specific embodiment, the agent is a drug or a nonpeptide drug. Identification and development of antagonists, agonists, selective antagonists, and selective agonists of CRFR2 are contemplated by the present invention.

"Peptide," "polypeptide," and "protein" may be used interchangeably, and refer to a polymer in which the monomers are amino acids (both traditional and modified) and are joined by amide bonds. However, "peptides" are generally 150 amino acids or less in length, or, in certain embodiments of the invention, are less than 100 amino acids, or less than 75, 70, 65, 60, 50, 45, 40, 35, 30, 25, 20, 15, 10 amino acids in length or any length therebetween. The term "domain" as used herein refers to a subsection of a polypeptide that possesses a unique structural or functional characteristic; typically, this characteristic is similar across a diverse set of polypeptides. The subsection typically comprises contiguous amino acids, although it may also comprise amino acids which act in concert or which are in close spatial proximity, as contrasted with linear proximity, due to protein folding. As used herein, the "extracellular domain" refers to the extracellular domain 1 ($ECD_1$) of B1 G-coupled proteins receptors, or any functional, ligand-interacting portion or fragment thereof, including substituted or mutated forms of the extracellular domain 1, including fusion proteins. In a preferred embodiment the $ECD_1$ of CRFR2 is used.

In specific embodiments, a known modulator is astressin, astressin B, astressin$_2$-B, or urocortin III. Astressin compounds are CRF analogs with high binding affinity for CRF receptors. Known CRF receptor modulators that may be improved by the methods of the present invention include, but is not limited to compounds as described in U.S. Pat. Nos. 6,747,034; 6,664,261; 6,583,143; 6,541,469; 6,531,475; 6,514,982; 6,500,839; and 6,348,466, each of which is incorporated herein by reference in their entirety.

It is also contemplated that the ECD of GPCR interacts with a second peptide receptor or polypeptide. The interaction could initiate downstream signaling events from one or both receptors. In a particular aspect the second peptide receptor is an EGF-like receptor. Thus, a candidate agent may be designed to modulate other interaction sites on the ECD.

It is specifically contemplated that any embodiment discussed with respect to a particular method or composition may be implemented with respect to other methods and compositions of the invention.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used in the conjunctive unless explicitly indicated to refer to alternatives only or the alternative are mutually exclusive, although the disclosure supports a definition that refers to only alternatives and "and/or."

The foregoing has outlined rather broadly the features and technical advantages of the present invention in order that the detailed description of the invention that follows may be better understood. It should be appreciated that the conception and specific embodiment disclosed may be readily utilized as a basis for modifying or designing other structures for carrying out the same or similar purposes of the present invention. It should also be realized that such equivalent constructions do not depart from the invention as set forth in the appended claims. It is to be expressly understood that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1A is a ribbon diagram of the lowest energy conformer highlighting the β-sheets and the disulfide bonds. FIG. 1B is a superposition of 20 conformers representing the 3D NMR structure. Only amino acid residues 44-119 are shown. The bundle is obtained by superimposing the backbone $C^\alpha$carbons of residues 58-83 and 99-113. The program MOLMOL was used to generate the figures and in the following figures the conformer with the lowest CYANA target function is used to represent the 3D structure of $ECD_1$-CRFR2β.

FIG. 2A is a stereo view and FIG. 2B is the surface of the 3D structure showing side chains of the conserved amino acids within the B1 family of GPCRs. The salt bridge between Asp65 and Arg101 is labeled by the dashed line. FIG. 2C is a sequence alignment of the $ECD_1$ of the CRF-R family.

FIG. 3A is a 2D [$^{15}$N, $^1$H]-HMQC spectra of $ECD_1$-CRFR2β in the absence and presence of astressin. FIG. 3B is a plot of the normalized chemical shift changes $[\Delta(\delta(^1H))^2+\Delta(^{15}N))^2/5]^{1/2}$ observed in the complex versus the amino acid sequence. FIG. 3C is a surface representation of $ECD_1$-CRFR2β showing the amino acids involved in binding with astressin. FIG. 3D is a competitive displacement by astressin of [$^{125}$I-DTyr$^0$]-astressin bound to membranes from COSM6 cells transiently expressing myc-mCRFR2β (●); myc-mCRFR2β (K92Q) (□); myc-mCRFR2β (R112E) (Δ); myc-mCRFR2β (I67E)(◇); myc-mCRFR2β (R112W) (∇).

FIG. 4A is the surface presentation of $ECD_1$-CRFR2β and astressin B with the electrostatic potential of both the molecules. The proposed binding interface between $ECD_1$-CRFR2β and the ligand is indicated in an opened view. Proposed electrostatic interactions include Glu39-Arg112 ($ECD_1$) and Arg35-Glu96 ($ECD_1$), as well as hydrophobic interactions (Leu37, Ile41 of the ligand with Y115 and P120 of $ECD_1$). FIG. 4A is a schematic of the hormone binding in the full-length receptor. The peptide hormone structure contains a kink at approximtely residue 24. The N-terminal segment is important for receptor activation and signaling. The positively charged surface of the $ECD_1$ is facing the transmembrane segment. The transmembrane segment of the receptor is modeled using the rhodopsin structure (PDB code 1HZX). Orientation (B) is rotated relative to the standard orientation of (A) by 90 and 180 degrees along the vertical axes and horizontal axes, respectively.

Figure 1A:
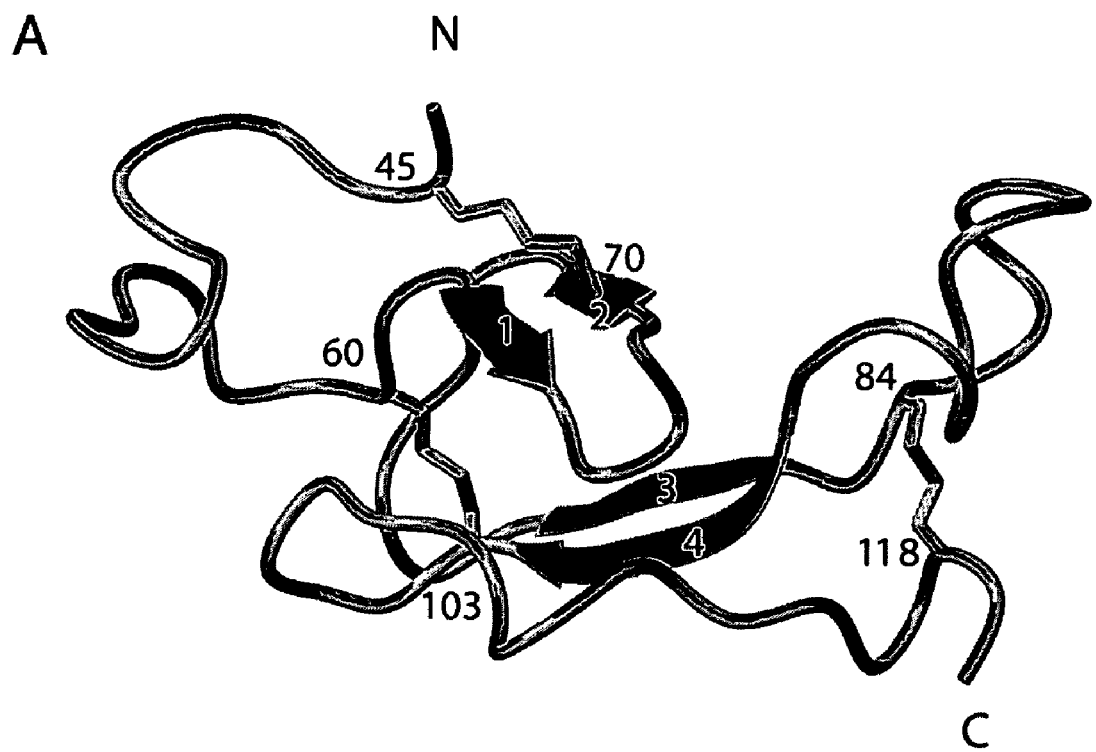
FIGS. 1A-1B show the 3D structure of $ECD_1$-CRFR2β.

Color versions of similar drawings can be found in Grace et al., 2004, which is incorporated herein by reference in its entirety.

DETAILED DESCRIPTION OF THE INVENTION

CRFR2 is a member of the B1 subfamily of G-protein coupled receptors (GPCRs), a class of receptors characterized by seven transmembrane helices. The structure of the N-terminal extracellular portion of CRFR2 may serve as a surrogate for the CRFR2 protein. It is contemplated that the extracellular domain of CRFR2 can be expressed apart from the transmembrane domains in order to more easily elucidate the structure of the ligand-interacting domain of the receptor and its association with other polypeptides, peptides, small molecules, and modifications thereof. The extracellular domain may be obtained by recombinant expression of the portion of the CRFR2 gene that encodes the extracellular domain of the polypeptide, or through de nova synthesis.

Certain aspects of the present invention provide methods of identifying modulators (antagonist or agonist) of B1 GPCRs. The modulators can be used as therapeutic agent for the treatment of a wide range of disorders or illnesses including endocrine, psychiatric, and neurologic disorders or illnesses. The present invention provides a three-dimensional model or representation of the extracellular domain 1 ($ECD_1$) of an exmplary B1 GPCR, i.e., CRFR2, that is used as a basis for rational drug design. Preferred aspects of the invention involve methods analyzing the structure of the extracellular domain of CRFR2, designing, or modifying an modulating agent to interact with an ECD1 with favorable molecular interactions, testing or assessing the activity of such an agent, and modeling and designing modulating agents for other B1-GPCRs using the CRFR2 structure or modifications thereof.

In certain embodiments of the invention, it is contemplated that the methods described herein are applicable to CRFR2, including α,β,γ splice variants, as well as CRFR1 (SEQ ID NO:6, SEQ ID NO:7). In other embodiments of the invention, the methods described herein are applied to the B1 family of GPCRs including, but not limited to receptors for glucagon (SEQ ID NO:8), glucagon like peptide (SEQ ID NO:9), parathyroid hormone (SEQ ID NO:10), secretin (SEQ ID NO:11), calcitonin (SEQ ID NO:12), vasoactive intestinal peptide (SEQ ID NO:13), growth hormone releasing factor (SEQ ID NO:14), pituitary adenylate cyclase-activating polypeptide (SEQ ID NO:15), and glucose-dependent insulinotropic polypeptide. Further, both transmembrane and soluble forms of the above receptors are viable targets for use in the methods of the present invention. For example, the soluble forms of CRFR1 and CRFR2α may be used as representative ECDs or GPCRs.

In a specific embodiment, the structure of the extracellular domain of CRFR2 comprises a three-dimensional nuclear magnetic resonance (NMR) structure. Solution nuclear magnetic resonance uses an aqueous solution of a purified extracellular domain of CRFR2 polypeptide; while the molecules tumble and vibrate with thermal motion. NMR detects chemical shifts of the atomic nuclei in the polypeptide with nonzero spin. The shifts depend on the electronic environments of the nuclei, namely, the identities and distances of nearby atoms. $^1$H is the only naturally occurring atom in proteins observed by NMR. The extracellular domain of CRFR2 is labeled with $^{13}$C and $^{15}$N. NMR analysis of the extracellular domain of CRFR2 provides estimates of distance between specific pairs of atoms, called "constraints". Constraints obtained are for both bonded and non-bonded atom pairs (through-bond or through-space distances). With a sufficient number of such constraints, the number of configurations consistent with the data becomes finite. The result is an ensemble of models, rather than a single structure. Often the positions are the average position of atoms in the different models, and the average model is adjusted to obey normal bond distances and angles ("restrained minimization"). Structures for the extracellular domain of CRFR2 fitting the NMR data with good stereochemistry are on deposit with the Protein Data Bank in PDB ID 1U34, which is incorporated herein by reference in its entirety. An example of the structure of CRFR2 is the structure defined by the parameters set forth in Table 2, or, alternatively, as set forth in FIG. 1. Furthermore, atomic coordinates of a representative conformer of the structure are in Table 3 below.

In still further embodiments, a processor may be used to model an extracellular domain of a B1 GPCR and determine agents that may fit and bind to at least one contact point on the GPCR. The processor may be any computer-readable media known in the art. For example, it may be embodied internally or externally on a hard drive, ASIC, CD drive, DVD drive, tape drive, floppy drive, network drive, flash, or the like. Processor can indicate any computing device capable of executing instructions including, without limitation, obtaining the coordinates of the GPCR, determining a binding site on the GPCR, designing an agent that may bind with the binding site of the GPCR, and/or assessing the antagonist or agonist activity of the agent. In one embodiment, the processor is a personal computer (e.g., a desktop or laptop computer operated by a user). In another embodiment, processor may be a personal digital assistant (PDA) or other handheld computing device.

In some embodiments, the processor may be a networked device and may constitute a terminal device running software from a remote server, wired or wirelessly. Input from a user or other system components may be gathered through one or more known techniques such as a keyboard and/or mouse. Alternatively, the processor may be configured to import data from a server via a wired or wireless network. Output, if necessary, may be achieved through one or more known techniques such as an output file, printer, facsimile, e-mail, webposting, or the like. Storage may be achieved internally and/or externally and may include, for example, a hard drive, CD drive, DVD drive, tape drive, floppy drive, network drive, flash, or the like. The processor may use any type of monitor or screen known in the art, for displaying information, such as but not limited to, possible agents binding to a contact site of the GPCR. For example, a cathode ray tube (CRT) or liquid crystal display (LCD) can be used. One or more display panels may also constitute a display. In other embodiments, a traditional display may not be required, and the processor may operate through appropriate voice and/or key commands.

Analysis of the extracellular domain of CRFR2 enables one to design candidate agents or improve known agents for modulating a receptor. An "agent" or "candidate agent" as identified by the methods of the present invention includes, but is not limited to a protein, polypeptide, peptide, peptidomimetic, nucleic acid (including DNA or RNA), molecule, compound or drug. In a specific embodiment of the invention, the agent is a peptide, peptoid, or a peptide mimic. In another embodiment, the agent is a drug or a nonpeptide drug. Antagonists, agonists, selective antagonists, and selective agonists of CRFR2 are agents envisioned by the present invention.

"CRFR2 receptors" as utilized herein refers to receptor polypeptides or proteins when in native form bind their designated ligands, including, but not limited to corticotropin-releasing factor, urotensin I, and urocortin I. U.S. Pat. No. 5,786,203, herein incorporated by reference in its entirety, describes exemplary sequences and nucleic acid constructs for use in the present invention. In certain embodiments of the invention, it is contemplated that the mouse CRFR2 (GenBank Accesion No: NM 009953 SEQ ID NO:1 and NP 034083 SEQ ID NO:2) receptor is used for molecular modeling to design antagonists, agonists, selective antagonist, or selective agonist. In certain embodiments the ECD1 comprises amino acids 39-133 of SEQ ID NO:2. In other embodiments of the invention, it is contemplated that the human CRFR2 (GenBank Accesion No: NM 001883 SEQ ID NO:3 and NP 001874 SEQ ID NO:4) is used for design of antagonists, agonists, selective antagonist, or selective agonist. In certain embodiments the ECD1 comprises amino acids 8-102 of SEQ ID NO:4. The extracellular domains of both human and mouse CRFR2 may be either the entire N-terminal extracellular domain, functional ligand-binding fragments, or fragments that interact with other cellular components, such as other proteins.

In still a further embodiment, the extracellular domain of CRFR2 comprises amino acids 39-133 of SEQ ID NO:2. In another embodiment, the extracellular domain of CRFR2 comprises amino acids 8-102 of SEQ ID NO:4. In certain embodiments, it is contemplated that candidate agents are designed to interact with amino acids 67-69, 90-93, 102-103 and/or 112-116, of SEQ ID NO:2 or analogous amino acids in other B1 GPCR ECDs. In specific embodiments, candidate agents are designed to interact with amino acids 67, 92, and 112 of SEQ ID NO:2 or analogous amino acids in other B1 GPCR ECDs. In one embodiment if the present invention, the antagonist or agonist binds in the proximity of one or more amino acids in the ECD of CRFR2. In another embodiment of the invention, the antagonist or agonist binds in the proximity of a short consensus repeat domain of the ECD of CRFR2.

The present invention also provides for methods to improve known modulators of GPCRs, e.g., CRFR2, by analyzing or studying their structure when bound to the extracellular domain of the receptor, and improving their design within the parameters indicated by the structure analysis. It is contemplated that by analyzing the structure the antagonist or agonist can be modified to bind the receptor with higher affinity.

Aspects of the invention include methods for screening candidate agents comprising contacting the agent with the extracellular domain of a B1 GPCR, preferably of a CRFR2, and analyzing the ability of the agent to bind to the extracellular domain. For example, it is contemplated that the binding affinity of candidate agents for an extracellular domain will be determined. As used herein, "binding affinity" refers to the strength of an interaction between two entities, such as a protein-protein or protein-drug interaction. Binding affinity may be referred to the $K_a$, or association constant, which describes the likelihood of the two separate entities to be in the bound state. The binding affinity typically measures the ability of the interaction to minimize the free energy of the system that comprises the interacting species and the solvent. A variety of methods are used to determine the association constant. Typically, two separate entities are mixed, the unbound portion is separated from the bound portion, and concentrations of unbound and bound are measured. One with skill in the art realizes that there are various methods for measuring association constants. For example, the unbound and bound portions may be separated from one another through adsorption, precipitation, gel filtration, dialysis, or centrifugation. The measurement of the concentrations of bound and unbound portions may be accomplished, for example, by measuring radioactivity or fluorescence.

The terms "peptide," "polypeptide," and "protein" may all be used interchangeably, and refer to a polymer in which the monomers are amino acids (both traditional and modified) and are joined together through amide bonds. However, "peptides" are generally 150 amino acids or less in length, or, in certain embodiments of the invention, are less than 100 amino acids, or less than 75, 70, 65, 60, 50, 45, 40, 35, 30, 25, 20, 15, 10 amino acids in length or any length therebetween. The term "domain" as used herein refers to a subsection of a polypeptide that possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. As used herein, the "extracellular domain" refers to the extracellular domain 1 ($ECD_1$) of B1 G-coupled proteins receptors, or any functional, ligand-interacting portion or fragment thereof, including substituted or mutated forms of the extracellular domain 1. For example, the $ECD_1$ of CRFR2 is used in certain methods of the present invention.

In a still further embodiments, the known modulator is astressin, astressin B, astressin$_2$-B, urocortin III, or modification thereof. Astressin compounds are CRF analogs with high binding affinity for CRF receptors. CRF receptor modulators include, but are not limited to compounds as described in U.S. Pat. Nos. 6,747,034; 6,664,261; 6,583,143; 6,541,469; 6,531,475; 6,514,982; 6,500,839; and 6,348,466.

It is also contemplated that the ECD1 domain of GPCR interacts with one or more other receptors, polypeptides, or signal transduction cascades. Thus, the interaction could initiate downstream signaling events from one or more receptors. It is contemplated that the peptide receptor is an EGF-like receptor.

I. CRFR2 Antagonists and Agonists

CRFR2 antagonists and agonists identified by the methods of the present invention may be useful in treating physiological conditions or disorders arising from the hypersecretion or hyposecretion of CRF or other natural B1 GPCR ligands. Because CRF is believed to be a pivotal neurotransmitter that activates and coordinates the endocrine, behavioral, and autonomic responses to stress, the CRFR2 antagonists and agonists identified by the methods of the present invention can be used to treat neuropsychiatric disorders. Neuropsychiatric disorders treatable by the CRFR2 antagonists and agonists may include, but are not limited to affective disorders such as depression; anxiety-related disorders such as generalized anxiety disorder, panic disorder, obsessive-compulsive disorder, abnormal aggression; cardiovascular abnormalities such as unstable angina and reactive hypertension; and feeding disorders such as anorexia nervosa, bulimia, and irritable bowel syndrome. CRFR2 antagonists and agonists may also be useful in treating stress-induced immune suppression associated with various diseases states, as well as stroke. Other uses of the CRFR2 antagonists and agonists identified by the method of the present invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal syndromes and conditions (including alcoholism).

II. Protein-Structure Based Design of Antagonists or Selective Agonists of CRFR2

Molecular modeling may use computers to model the molecular structure. Non-limiting examples of such methods include molecular graphics (i.e., 3-D representations) to computational chemistry (i.e., calculations of the physical and chemical properties). Using molecular modeling, rational drug design programs can look at a range of molecular structures that may fit into an active site of an enzyme or interact with polypeptide. By using computer programs, for example, a determination can be made as to which compounds actually fit into or bind a given site or potential active. U.S. patents that provide additional information on molecular modeling include U.S. Pat. Nos. 6,093,573; 6,080,576; 5,612,894; 5,583,973; 5,030,103; 4,906,122; and 4,812,128, each of which is incorporated herein by reference in its entirety. As used in the methods described herein, the term "computer fitting analysis" or "modeling" refers to a schematic or other work that is prepared using a computer algorithms or computer programs that can process and provide information about protein structure and conformation. A number of such programs and algorithms are readily available and known to those of skill in the art. They can configure a protein sequence into a 3-dimensional molecule and additionally configure it with a ligand or other substrate, such as a particular nucleic acid molecule.

In the context of the invention, the program or algorithm will configure and improve (in some cases, optimize) an interface, including its amino acid side chains, between the ligand-binding domains of CRFR2 and a ligand, such as a candidate antagonist or agonist. The program or algorithm will also configure and improve or optimize the interface, including its amino acid side chains, between ECD1 of CRFR2 and a ligand. This program or algorithm will allow the detection, identification, and improvement/optimization of contact points between individual protein domains or between protein domains and ligands. A "contact point" refers to the point at which individual protein domains, or protein domain and ligand molecules interact. Such contact points are formed as a result of specific binding between two protein domains or between protein domains and a nucleic acid molecule. Other amino acids within the interface may also be modified to enhance or improve the interaction between protein domains or between protein domains and ligands. Modifications to the interface may result in improved interaction between individual protein domains or between protein domain(s) and ligands present in the complex or may result in improved stability of the protein. In this context, amino acid side chains represent "potential contact points" in the interface that may be modified in various combinations. "Interface" refers to the amino acids between two interacting protein domains or between protein domains and ligands that form contact points, as well as those amino acids that are adjacent to contact points and along the surface between individual protein domains, or between protein domains and ligands.

An algorithm or program will typically allow the identification of potential contact points, residues that are not properly interacting with the target sequence, residues between two interacting protein domains or between protein domains and ligands inhibiting or reducing. Thus, methods of the invention further include the step of identifying potential contact points between individual protein domains or between protein domains and ligands, and/or identifying amino acids along the interface or in the proximity of the interface that can be modified to improve the interface (that is to modify the interaction as desired by the protein engineer). Computational modeling that occurs in different embodiments of methods of the invention involves modeling of the various entities to show their interactions with one another, such interactions include, but are not limited to interactions between or among ligands, peptides, polypeptides, and single or multiple protein domains.

Given a B1 GPCR extracellular domain structure, a potential modulator of a B1 GPCR can be identified and analyzed using computer modeling techniques. There are a number of computer programs that can be used to identify potential small molecule and peptide compounds that bind with favorable binding energies. Non limiting examples include: GRID (available form Oxford University, UK), MCSS (available from Accelrys, San Diego, Calif.), AUTODOCK (available from The Scripps Research Institute, La Jolla, Calif.), FLEX X (available from Tripos, St. Louis. Mo.), DOCK (available from University of California, San Francisco), CAVEAT (available from University of California, Berkeley), HOOK (available from Accelrys, San Diego, Calif.), and 3D database systems such as MACCS-3D (available from MDL Information Systems, San Leandro, Calif.), UNITY (available from Tripos, St. Louis. MO), and CATALYST (available from Accelrys, San Diego, Calif.) Potential inhibitors may also be computationally designed by using such software packages as LUDI (available from Accelrys, San Diego, Calif.), LEGEND (available from Accelrys, San Diego, Calif.), and LEAPFROG (Tripos Associates, St. Louis, Mo.). The computer and modeling techniques may be performed on any suitable hardware or computer system, such as, but not limited to, a desktop computer, a personal digital assistant (PDA), a notebook processor, a tablet PC, and the like. This procedure can include computer fitting of potential modulators of B1 GPCRs to ascertain how well the shape and chemical structure of the potential modulator will bind (Bugg et al., 1993; West et al., 1995). Computer readable mediums may also execute instructions to estimate the attraction, repulsion, and steric hindrance of the ECDs with a modulator/inhibitor (e.g., CRFR2 and a potential inhibitor). Generally, the tighter the fit the lower the steric hindrances, the greater the attractive forces, and the more potent a modulator. Furthermore, the more specificity in the design of a potential drug the more likely that the drug will not interact as well with other proteins. This will minimize potential side effects due to unwanted interactions with other proteins.

Initially, compounds known to bind CRFR2, for example, astressin, can be systematically modified by computer modeling programs until one or more promising potential analogs are identified. In addition, systematic modification of selected analogs can then performed by computer modeling programs until one or more potential analogs are identified. It is also contemplated that truncating or varying the length CRFR2 agonists, or functional analogs thereof, will create molecules with CRFR2 antagonistic properties. Truncating a portion of the agonist molecule that inserts itself into the plasma membrane will impair the ability of the molecule to activate downstream signaling events. Amino acids 1-8 are crucial for agonist activity of the CRF peptide (Rivier et al., 1984).

A potential modulator can be selected from a library of chemicals that are commercially available from most large chemical companies including Merck, GlaxoWelcome, Bristol Meyers Squib, Monsanto/Searle, Eli Lilly, Novartis and Pharmacia UpJohn; or alternatively the potential modulator may be synthesized de novo. As mentioned above, the de novo synthesis of one or even a relatively small group of specific compounds is reasonable in the art of drug design. The potential modulator can be placed into a standard binding assay with a B1 GPCR, or an active fragment thereof, for example, the extracellular domain.

III. Screening Assays

B1 GPCR binding agents or compounds may be tested in biochemical assays to further identify their effectiveness in binding to and modulating B1 GPCR activity. Assays may be conducted in cell free systems, in isolated cells, or in organisms, including animals.

A. In Vitro Assays

One assay is the binding assay. Binding of a molecule to a target may be inhibitory, due to steric, allosteric or charge-charge interactions. Binding assays can be performed in solution or on a solid phase support. Binding assays may be used as a first round screen to rapidly eliminate certain compounds before moving into more sophisticated screening assays. The target may be either free in solution, fixed to a support, or expressed in or on the surface of a cell. Examples of supports include, but are not limited to nitrocellulose, column, gel, or surface of a plasmon resonance (SPR) device (Szabo et al., 1995). Either the target or the compound can be labeled, thereby permitting determination of binding.

In another embodiment, the assay may measure the enhanced binding of a target to a natural or artificial substrate or binding partner. Usually, the target will be the labeled species, decreasing the chance that the labeling will interfere with the binding moiety's function. One may measure the amount of free label versus bound label to determine binding or inhibition of binding. In other embodiments, binding is determined by gel electrophoresis, gel filtration chromatography, fluorescence quenching, flow cytometry, ELISA, solid phase immunoassay, confocal microscopy, or surface plasmon resonance (SPR). Downstream signal transduction is indicative of binding to a receptor, for example transactivation of ErbB2.

A technique for high throughput screening of compounds is described in PCT Application WO 84/03564. In high throughput screening, large numbers of candidate inhibitory test compounds, which may be small molecules, natural substrates and ligands, or may be fragments or structural or functional mimetics thereof, are synthesized on a solid substrate, such as plastic pins or some other surface. Alternatively, purified target molecules can be coated directly onto plates or supports for use in drug screening techniques. Also, fusion proteins containing a reactive region (preferably a terminal region) may be used to link an active region of an enzyme to a solid phase, or support. The test compounds are reacted with the target molecule, and bound test compound is detected by various methods (see, e.g., Coligan et al., 1991).

B. In Vivo Assays

In vivo assays involve the use of various animal models, including transgenic animals that have been engineered to have specific defects, or carry markers that can be used to measure the ability of a candidate substance to reach and affect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses, and monkeys (including, but not limited to chimps, gibbons and baboons). Assays for modulators may be conducted using an animal model derived from any of these species and others.

In such assays, one or more candidate substances are administered to an animal and the ability of the candidate substance(s) to alter the physiology of the animal or the model condition to be treated, as compared to a similar animal not treated with the candidate substance(s), are assessed. The characteristics may be any of those discussed above with regard to the function of a particular compound (e.g., enzyme, receptor, and hormone levels or activity) or cell (e.g., growth, tumorigenicity, survival), or a broader indication such as behavior, anemia, immune response, etc.

Treatment of these animals with candidate substances will involve the administration of the compound in an appropriate form. Administration can be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

C. Arrays

Hi-throughput assays, for example, arrays comprising a plurality of ligands arranged on a solid support, represent an important diagnostic tool provided by the invention. The use of arrays involves the placement and binding of nucleic acids, or another type of ligand having affinity for a molecule in a test sample, to known locations, termed sectors, on a solid support.

Devices employing such arrays might be employed as combinatorial chemical or drug screening devices, antibody arrays, peptide arrays, cell arrays, enzymatic activity arrays, or DNA or other polynucleotide arrays that will be selective for binding to related proteins or other biomolecules. In addition, encapsulated cells or biomolecules coated onto the walls of microcapillary tubes will function as flow through devices having single or multiple channels, which might be employed as screening devices or as biosensors on systems, such as in liquid chromatography or in "lab-on-a-chip" devices. Signal readout from such devices might be via binding of 5 fluorescent proteins or of antigens, to be measured by subsequent antibody-based detection methods (possibly employing additional arrays), or via reaction with endogenous biopathways which will result in the formation of a detectable species, e.g. enzymatic conversion of a substrate to a fluorescent dye molecule, or change in the electrical properties, e.g. conductivity, of the cell and/or surrounding matrix resulting from exposure to the specific agent.

In certain aspects to the invention, binding of a labeled ECD may be used to identify, confirm, or detect a binding affinity of a ligand for the ECD or the ECD for the ligand.

Arrays can be brought into contact with a test sample to determine the presence or absence of a given molecule in the sample. By including any additional other target nucleic acids or other types of ligands. Potentially thousands of target molecules in a test sample can be screened. Many different methods for preparation of arrays comprising target substances arranged on solid supports are known to those of skill in the art and could be used in accordance with the invention.

Specific methods for preparation of such arrays are disclosed in, for example, Affinity Techniques, Enzyme Purification: Jakoby and Wilchek, (1974). Examples of other techniques which have been described for the attachment of test materials to arrays include the use of successive application of multiple layers of biotin, avidin, and extenders (U.S. Pat. No. 4,282,287); methods employing a photochemically active reagent and a coupling agent which attaches the photoreagent to the substrate (U.S. Pat. No. 4,542,102); use of polyacrylamide supports on which are immobilized oligonucleotides (PCT Patent Publication 90/07582); use of solid supports on which oligonucleotides are immobilized via a 5'-dithio linkage (PCT Patent Publication 91/00868); and through use of a photoactivateable derivative of biotin as the agent for immobilizing a biological polymer of interest onto a solid support (see U.S. Pat. No. 5,252,743; and PCT Patent Publication 91/07087). In the case of a solid support made of nitrocellulose or the like, standard techniques for UV-crosslinking may be of particular utility (Sambrook et al., 2001).

IV. Protein Synthesis

It is contemplated that the protein or peptide compositions described herein may be synthesized de novo. For example, it is contemplated that peptide-based antagonists or selective agonists of a B1 GPCR, e.g., CRFR2, may be synthesized using the techniques described herein. Such peptide-based modulators may be modified or improved analogs of CRF, urocortin, or astressin B, among others. It is contemplated that in certain embodiments of the invention, the native chemical ligation procedure is used. The general procedure follows the method of Hackeng et al. (1999). Peptide fragments are synthesized using the Boc protocol on MBHA or CM resins. Thioester-containing fragments are synthesized on TAMPAL resin (trityl-associated-mercaptopropionic-acid-leucine), which is a MBHA resin modified with a thioamide linker. Leucine is first coupled to MBHA resin followed by S-tritylmercaptopropionic acid (Peptides Int'l.) to give the modified TAMPAL-MBHA resin. The trityl group is removed by two 5 min treatments of TFA/scavenger cocktail (95 TFA: 2.5 EDT: 2.5H$_2$O). The remainder of the peptide is synthesized using the Boc method of solid phase peptide synthesis.

After resin cleavage and purification of the peptide fragments, 1.5 equiv. thioester-peptide and 1 equivalent of Cys-peptide are dissolved in the ligation buffer at a concentration of 1-3 mM. The ligation buffer consists of 6 M guanidine-HCl and 0.1 N sodium phosphate, adjusted to pH 8.5 with NaOH, which normalizes to ~pH 7 upon addition of the peptide-TFA salts. Thiophenol and benzylmercaptan (4% v/v each) are also added to the reaction mixture to promote the thioester exchange reaction. The ligation reaction is then heated at 38° C. and progress is monitored by HPLC. The ligation of [Cys$^{21}$]-oCRF(21-41) or [HCys$^{21}$]-oCRF(21-41) to [His$^{13}$(DNP)]-oCRF(1-20)-MPAL-NH2 reaches maximal completion at 24 or 48 h, respectively.

Another method that is contemplated for use in the present invention uses the Staudinger ligation between a C-terminal fragment containing a phosphinothioester and an N-terminal azido-peptide. The coupling and rearrangement occurs in high yield in aqueous THF at room temperature for 12 h and without epimerization. This method has been used in the synthesis of ribonuclease A, consisting of 124 amino acids. Since RNase A contains a cysteine at position 110, fragment (110-124) was coupled to fragment (1-109) via NCL. Fragment (110-214) was synthesized from two smaller fragments using the Staudinger ligation method. Alternatively, other investigators have incorporated a removable thiol-containing auxiliary that is attached to the N-terminal amine of the peptide to be ligated.

An aspect of NCL that limits its practicality is that it is labor intensive at each step. To increase efficiency, solid-phase ligation strategies have been explored. Camarero et al. (1998) have used a thio-linked PEGA support to produce the peptide thioester, which eliminates handling of the free thioester in solution. The resin is stable to HF, which cleaves off the protecting groups, but is displaced during the 2-3 h ligation reaction with the Cys-peptide fragment in the presence of aromatic thiol cofactors. Another approach developed by the Dawson group utilizes a safety catch acid-labile linker on DADPA gel (Pierce), upon which successive NCL reactions may build up the desired protein. The support is stable to all solid phase synthetic reaction conditions until it is concomitantly reduced with $SiCl_4$ and cleaved with TFA to produce the peptide-amide.

Faced with the dilemma of synthesizing proteins that contained neither Cys, Met or Val, that certain amino acids would best qualify as a conservative substitute that would not affect structure and biological. The primary method for predicting the utility of amino acid replacement has been the use of mutation matrices as first published by Dayhoff and Eck (1968) using protein evolutionary data. This method has been expanded over the years by many investigations to include physiochemical and structural properties and the hierarchical clustering of these data. This work has matured into the AAIndex (See Kawashima and Kanehisa, 2000), which forms the basis of the current analysis.

A hypothesis emerging from inspection of the mutation matrices contained within the AAIndex is that amino acid replacement can be highly context specific. Given the four major clusters originally identified by Nakai and co-workers (i.e., α-helix and turn propensities, β-strand propensity, hydrophobicity, and physiochemical properties) an examination of the role of Met, and more specifically of the likelihood of successful replacement, is possible. Regarding hydrophobicity, the work of George et al. (1990) on mutational frequency suggests that Met is promiscuous, replacing Ala, Asn, Cys, Qln, Gly, His, Ile, Leu, Phe, Pro, Ser, Thr, Tyr and Val. However, the work of Johnson and Overington toward identifying a structural basis for sequence comparison suggests that Met is much more severely restricted, replacing only Ile and Leu. The sequence alignment approach to quantifying conformational similarity of Kolaskar and Kulkami-Kale suggests that Met can replace Arg, Leu, Lys, Phe or Trp. A significant body of work conducted by Luthy and co-workers examined the role of secondary structural context in amino acid replacement. This work suggests that Met could replace Ile, Leu or Phe in an outside helix, but Met is a poor replacement for any amino acid in an "inside helix" context, as it is poor in the "inside other" and "inside beta" contexts. However, in an "outside other" context, Met replaces Ile, Leu, Phe and Val, and in an "outside beta" context, Met replaces Ile, Leu, Pro and Val. The structurally-derived correlation method of Niefind and Schomburg suggests that Met replaces Ala, Gln, Glu and Ile. Finally, the work of Riek et al., (1995) on the evolutionary conservation of hydrophilic and hydropohobic residues in transmembrane sequences suggests that Met can replace Glu, His, Lys, and Thr.

V. Peptide Characterization

HPLC, CZE, CD, $[\alpha]_D$, FPLC, NMR, LSIMS, and other available techniques such as counterion (ACOH and TFA) content using HPLC may be used to characterize peptides in the present invention. In one embodiment, peptides are characterized by well-documented build-up of the peptide sequence on the polymer to insure us that the proper sequence was assembled on the synthesizer. HPLC using the TEAP buffer at different pHs and 0.1% TFA in $CH_3CN$ and several columns ($C_{18}$, $C_4$ and diphenyl) are able to provide an appreciation of the amounts and relative properties of the contaminants. The TEAP buffer in the presence of acetonitrile for size exclusion chromatography is appropriate In one embodiment, capillary zone electrophoresis (CZE) is used for the quantitative analysis of the peptides and their impurities. CZE is carried out using a Beckman P/ACE System 2050 controlled by an IBM Personal System/2 Model 50Z and using a ChromJet integrator. Several buffers have been used and conditions optimized (addition of $CH_3CN$ or TFE in the buffers) for the elution of CRF analogs.

In another embodiment, optical rotation is used for the characterization of novel amino acids or scaffolds. Optical rotations of peptides are measured (sodium D line) in an adequate solvent (c=0.2-1.0) using a Perkin-Elmer 241 polarimeter and a 100-μL cell.

It is contemplated that fast performance liquid chromatography, FPLC, is used for the characterization and purification of the analogs, such as peptide ligands for CRFR2 or mutations of CRFR2. Recent results indicate that ion-exchange chromatography of small peptides and proteins using recently developed supports can be extremely resolutive and can be used for both analytical and preparative purposes.

It is contemplated that high field NMR spectrometry is used for the characterization of some selected constrained and B1 GPCR-selective analogs, specifically CRFR-selective analogs, the structures of which will be usefult for our understanding of the structural basis for receptor selectivity and mechanism of action.

Circular dichroism (CD) spectroscopy is contemplated in certain embodiments of the invention to correlate theoretical and observed CD spectra of selected CRF agonists and antagonists using the CaPPS package of Applequist and co-workers.

Mass spectrometry can be used for the identification and systematic characterization of peptides and amino acid derivatives synthesized in the laboratory.

VI. Protein Expression and Purification

Embodiments of the present invention may require the use of certain proteins, polypeptides, peptides, or enzymes, e.g., B1 GPCR or CRFR2. CRFR2 or the extracellular domain of CRFR2, e.g., may be obtained by any technique known to those of skill in the art, including the expression of proteins, polypeptides or peptides through standard molecular biological techniques (Sambrook, 2001), the isolation of proteinaceous compounds from natural sources, or the chemical synthesis of proteinaceous materials.

Various host-expression vector systems may be utilized to express the ECDs of the invention. Such host-expression systems represent vehicles to produced and subsequently purify the polypeptides of interest, but also represent cells that may, when transformed or transfected with the appropriate coding sequences, exhibit the protein of the invention in situ. These include but are not limited to microorganisms such as bacteria (e.g., *E. coli, B. subtilis*) transformed with recombinant bacteriophage DNA, plasmid DNA or cosmid DNA expression vectors containing protein coding sequences; yeast (e.g. *Saccharomyces, Pichia*) transformed with recombinant yeast expression vectors containing the protein coding sequences; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing protein coding sequences; or mammalian cell systems (e.g. COS, CHO, BHK, 293, 3T3) harboring recombinant expression constructs containing promoters derived from the genome of mammalian cells (e.g., metallothionine promoter) or from mammalian viruses (e.g., the adenovirus late promoter; the vaccinia virus 7.5 K promoter).

In bacterial systems, a number of expression vectors may be advantageously selected depending upon the use intended for the protein being expressed. For example, when a large quantity of such a protein is produced for use in the generation of antibodies or to screen peptide libraries and the like, vectors that direct the expression of high levels of fusion protein products that are readily purified may be desirable. Such vectors include, but are not limited, to the *E. coli* expression vector pUR278 (Ruther et al., 1983), in which the protein coding sequence may be ligated in frame with the lac Z coding region producing a fusion protein (Inouye and Inouye, 1985; Van Heeke et al., 1989). pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned CRFR2 protein can be released from the GST moiety.

In an insect system *Autographa californica* nuclear polyhedrosis virus (AcNPV) is used as a vector to express foreign genes and encoded proteins. The virus grows in *Spodoptera frugiperda* cells. The coding sequence may be cloned into non-essential regions (for example the polyhedrin gene) of the virus and placed under control of an AcNPV promoter (for example the polyhedrin promoter). Successful insertion of coding sequence will result in inactivation of the polyhedrin gene and production of non-occluded recombinant virus (i.e., virus lacking the proteinaceous coat coded for by the polyhedrin gene). These recombinant viruses are used to infect *Spodoptera frugiperda* cells in which the inserted gene is expressed (see Smith, et al., 1983; U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan et al., 1984). Specific initiation signals may also be required for efficient translation of inserted coding sequences. These signals include the ATG initiation codon and adjacent sequences. In cases where an entire coding sequence, including its own initiation codon and adjacent sequences, is inserted into the appropriate expression vector, no additional translational control signals may be needed. However, in cases where only a portion of the coding sequence is inserted, exogenous translational control signals including the ATG initiation codon may be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter, et al., 1987).

In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and W138.

For long-term, high-yield production of recombinant proteins, stable expression is preferred. For example, cell lines may be engineered to stably express a polypeptide. Rather than using expression vectors that contain viral origins of replication, host cells can be transformed with DNA controlled by appropriate expression control elements (e.g., promoter, enhancer, sequences, transcription terminators, polyadenylation sites, etc.). Following the introduction of the foreign DNA, engineered cells may be allowed to grow for 1-2 days in an enriched media, and then are switched to a selective media. A selectable marker in the recombinant plasmid confers resistance to the selection and allows cells that stably integrate the plasmid into their chromosomes to grow and form foci, which are cloned and expanded into cell lines. This method may advantageously be used to engineer cell lines that express a polypeptide. Such engineered cell lines may be particularly useful in screening and evaluation of compounds that affect the endogenous activity of a polypeptide.

In one embodiment, timing or quantity of expression of the recombinant protein can be controlled using an inducible expression construct. Inducible constructs and systems for inducible expression of recombinant proteins are known to those skilled in the art. Examples of such inducible promoters or other gene regulatory elements include, but are not limited to, tetracycline, metallothionine, ecdysone, and other steroid-responsive promoters, rapamycin responsive promoters, and the like (No et al., 1996; Furth et al., 1994). Additional control elements that can be used include promoters requiring specific transcription factors such as viral, particularly HIV, promoters. In one embodiment, a Tet inducible gene expression system is utilized. (Gossen et al., 1992; Gossen, et al., 1995). Using such a system, expression of the recombinant protein is placed under the control of the tetO operator sequence and transfected or transformed into a host cell. In the presence of TetR, which is co-transfected into the host cell, expression of the recombinant protein is repressed due to binding of the TetR protein to the tetO regulatory element. High-level, regulated gene expression can then be induced in response to varying concentrations of tetracycline (Tc) or Tc derivatives such as doxycycline (Dox), which compete with tetO elements for binding to TetR. Constructs and materials for tet inducible gene expression are available commercially from CLONTECH Laboratories, Inc., Palo Alto, Calif.

When used as a component in an assay system, a polypeptide may be labeled, either directly or indirectly, to facilitate detection of a complex formed between the polypeptide and a test substance. Any of a variety of suitable labeling systems may be used including, but not limited to radioisotopes; enzyme labeling systems that generate a detectable calorimetric signal or light when exposed to substrate; and fluorescent labels. Where recombinant DNA technology is used to produce a polypeptide for such assay systems, it may be advantageous to engineer fusion proteins that can facilitate labeling, immobilization, and/or detection.

Indirect labeling involves the use of a protein, such as a labeled antibody, which specifically binds to the protein. Such antibodies include but are not limited to polyclonal, monoclonal, chimeric, single chain, Fab fragments and fragments produced by a Fab expression library.

In certain embodiments a B1 GPCR, for example CRFR2, or the extracellular domain of a B1-GPCR may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays. There is no general requirement that the protein or peptide always be provided in their most purified state. Indeed, it is contemplated that less substantially purified products will have utility in certain embodiments. Examples of purification techniques include, but are not limited to, column chromatography, High Performance Liquid Chromatography (HPLC), medium pressure liquid chromatography, Gel chromatography, Affinity Chromatography, ion exchange chromatography, hydrophobic interaction chromatography, size-exclusion chromatography, preparative gel electrophoresis, or isoelectric focusing chromatography (Sambrook, 2001).

VII. Candidate Agents

The term "candidate agents" refers to any antagonist or agonist that may potentially modulate (negatively or positively) signal transduction of a B1 GPCR, in particular aspects a CRFR2. An agonist refers to a substance that increases the effective level of B1 GPCR activity through interaction with the extracellular domain. An antagoinst refers to a substance that decreases B1 GPCR activity through interaction with the extracellular domain.

Candidate substances can include fragments or parts of naturally-occurring compounds. Candidate substance also includes various synthetic and recombinant molecules or libraries of such compounds or molecules. In one embodiment, the candidate substances are small molecules. In yet other embodiments, candidate substances may be synthetic or natural peptides. Examples of small molecules that may be screened include, but are not limited to, small organic molecules, peptides or fragments thereof, peptide-like molecules, nucleic acids, polypeptides, peptidomimetics, carbohydrates, lipids, or other organic (carbon-containing) or inorganic molecules. Many pharmaceutical companies have extensive libraries of chemical or biological mixtures, often fungal, bacterial, or algal extracts, which can be screened with any of the assays of the invention to identify compounds that modulate a B1 GPCR.

Alternatively, it is proposed that compounds isolated from natural sources, such as animals, bacteria, fingi, plant sources, including leaves and bark, and marine samples may be assayed or modeled as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors, or any other compounds that may be designed through rational drug design starting from known inhibitors or stimulators. Other suitable candidate substances, compounds, or modulators of the present invention will function to regulate the activity of a B1 GPCR. Such candidate substances may include, but are not limited to, monoclonal and polyclonal antibodies, aptamers, and aptazymes.

A. Peptide Mimetics

As used herein, the terms "mimetic" or "peptide mimetic" may be used interchangeably, and refer to a compound that biologically mimics determinants on hormones, cytokines, enzyme substrates, viruses, ligands, or other bio-molecules. Mimetics may antagonize, stimulate, or otherwise modulate the physiological activity of the receptors for natural ligands. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of an antibody or an antigen. Thus, a peptide mimetic permits molecular interactions similar to the natural molecule. Molecules are designed to mimic amino acid residues in alpha-helix or beta-turn conformations on the surface of a protein. Such molecules disrupt certain protein-protein interactions involved in disease or abberrent physiology.

Peptide mimetics can be designed and produced by techniques known to those of skill in the art. (See e.g., U.S. Pat. Nos. 4,612,132; 5,643,873 and 5,654,276, the teachings of which are herein incorporated by reference). These mimetics can be based, for example, on a specific B1 GPCR ligand and maintain the relative positions in space of the corresponding ligand. These peptide mimetics possess biologically activity (e.g., GPCR inhibiting or stimulating activity) similar to the biological activity of the corresponding peptide compound, but possess a "biological advantage" over the corresponding natural ligand with respect to one or more of the following properties that include, but are not limited to affinity, activity (inhibitory or stimulatory), solubility, pharmacokinetics, stability, and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic. Modifications of peptides to produce peptide mimetics are described in U.S. Pat. Nos. 5,643,873 and 5,654,276, the teachings of which are incorporated herein by reference.

Where the peptide mimetics of present invention comprise amino acids, the test substance can also be cyclic protein, peptides, and cyclic peptide mimetics. Such cyclic test substances can be produced using known laboratory techniques (e.g., as described in U.S. Pat. No. 5,654,276, the teachings of which are herein incorporated in their entirety by reference).

The mimetics of the present invention can comprise either the 20 naturally occurring amino acids or other synthetic amino acids or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | Ahyl | Allo-Hydroxylysine |
|  |  | 3Hyp | 3-Hydroxyproline |
| Abu | 2-Aminobutyric acid | 4Hyp | 4-Hydroxyproline |
| 4Abu | 4-Aminobutyric acid, piperidinic acid | Ide | Isodesmosine |
|  |  | Aile | Allo-Isoleucine |
| Acp | 6-Aminocaproic acid | MeGly | N-Methylglycine, sarcosine |
| Ahe | 2-Aminoheptanoic acid |  |  |
| Aib | 2-Aminoisobutyric acid | MeIle | N-Methylisoleucine |
| Baib | 3-Aminoisobutyric acid | MeLys | 6-N-Methyllysine |
| Apm | 2-Aminopimelic acid | MeVal | N-Methylvaline |
| Dbu | 2,4-Diaminobutyric acid | Nva | Norvaline |
| Des | Desmosine | Nle | Norleucine |
| Dpm | 2,2'-Diaminopimelic acid | Orn | Ornithine |
| Dpr | 2,3-Diaminopropionic acid |  | N-methylleucine |
| EtGly | N-Ethylglycine | Agl | Acylated aminoglycine (eqv to betidaminoacids |
| Aph | 4-minophenylalanine | (acylated) |  |

Synthetic amino acids encompassed by the present invention include, for example, naphthylalanine, L-hydroxypropylglycine, L-3,4-dihydroxyphenylalanyl, alpha-amino acids such as L-alpha-hydroxylysyl and D-alpha-methylalanyl, L-alpha-methyl-alanyl, beta amino-acids such as beta-alanine, and isoquinolyl. In other aspects C-alpha-methyl amiono acids, in particular C-alpha-methyl-leucine may be included in an engineered mimetic or library of such compounds.

D-amino acids and other non-naturally occurring synthetic amino acids can be incorporated into the test substances of the present invention. Such non-naturally occurring synthetic amino acids include those where the naturally occurring side chains of the 20 genetically encoded amino acids (or any L or D amino acid) are replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

As used herein, "lower alkyl" refers to straight and branched chain alkyl groups having from 1 to 6 carbon atoms, such as methyl, ethyl propyl, butyl and so on. "Lower alkoxy" encompasses straight and branched chain alkoxy groups having from 1 to 6 carbon atoms, such as methoxy, ethoxy and so on.

Cyclic groups can be saturated or unsaturated, and if unsaturated, can be aromatic or non-aromatic. Heterocyclic groups typically contain one or more nitrogen, oxygen, and/or sulphur heteroatoms, including, but not limited to furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. The heterocyclic groups can be substituted or unsubstituted. Where a group is substituted, the substituent can be alkyl, alkoxy, halogen, oxygen, or substituted or unsubstituted phenyl. (See U.S. Pat. Nos. 5,654,276 and 5,643,873, the teachings of which are herein incorporated by reference).

The peptide analogs or mimetics of the invention include isosteres. The term "isostere" as used herein refers to a sequence of two or more residues that can be substituted for a second sequence because the steric conformation of the first sequence fits a binding site specific for the second sequence. The term specifically includes, but is not limted to peptide back-bone modifications (i.e., amide bond mimetics). Such modifications include modifications of the amide nitrogen, the alpha-carbon, amide carbonyl, complete replacement of the amide bond, extensions, deletions or backbone crosslinks. Several peptide backbone modifications are known, including φ[$CH_2$ S], φ[$CH_2$ NH], φ[C(S)$NH_2$], φ[NHCO], φ[C(O) $CH_2$], and φ[(E) or (Z) CH.dbd.CH]. In the nomenclature used above, φ indicates the absence of an amide bond. The structure that replaces the amide group is specified within the brackets. Other examples of isosteres include peptides substituted with one or more benzodiazepine molecules (see e.g., James et al. 1993).

Other possible modifications include an N-alkyl (or aryl) substitution (φ[CONR]), backbone crosslinking to construct lactams and other cyclic structures, or retro-inverso amino acid incorporation (φ[HCO]). "Inverso" means replacing L-amino acids of a sequence with D-amino acids, and "retro-inverso" or "enantio-retro" means reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide and is able to bind the selected domain. See Goodman et al., 1981). See also U.S. Pat. No. 4,522,752 for further description of "retro-inverso" peptides.

EXAMPLES

The following examples are included to demonstrate preferred embodiments of the invention. It should be appreciated by those of skill in the art that the techniques disclosed in the examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a similar result without departing from the spirit and scope of the invention.

Example 1

Material and Methods

Mutagenesis. The myc-mCRFR2β, in which a c-myc epitope is inserted between residues 29 and 30, as well as all the point mutants were created by overlap extension PCR using mCRFR2β as the template. The PCR products were subcloned into pcDNA3 and the sequences were confirmed by automated sequencing.

Protein expression. A cDNA encoding amino acids 39-133 of mouse CRFR2β was inserted into pET-32a(+) (Novagen) with KpnI and XhoI, and its integrity confirmed by automated sequencing. The sequence of the protein is: GSG MKETAAAKFERQHMDSPDLGT (mCRF-R2β (39-133) (SEQ ID NO:16), in which an S-tag sequence (used for purification) is underlined and the additional amino acids are part of the thrombin cleavage site and the KpnI cloning site. The N-terminal residues are highly flexible as determined by NMR. The protein was expressed in minimal media containing 4 g/l $^{13}$C-D-glucose and 1 g/l $^{15}$N-ammonium sulfate. Protein purification was carried out as described (See Perrin et al., 2003). Twenty liters of expression media yielded one sample of $^{13}$C, $^{15}$N-labeled ECD$_1$-CRF-R2β with a concentration of ~0.2 mM.

Radioreceptor assays. Mutant receptors or myc-mCRFR2β, were transiently transfected into COSM6 cells followed by binding to crude membrane preparations. Binding to myc-mCRFR2β was performed in triplicate, as described (See Perrin et al., 2003).

NMR Experiments. All the NMR spectra were recorded at 25° C. on Bruker 700 MHz spectrometer equipped with four radio-frequency channels and triple resonance cryo-probe with shielded z-gradient coil. The NMR samples contained 0.2 mM of $^{13}$C, $^{15}$N-labeled ECD$_1$-CRFR2β in 10 mM Bis-Tris(HCl), 95% H$_2$O/5% D$_2$O at pH 7.4. Sequential assignment and structure determination was performed with the standard protocol for $^{13}$C, $^{15}$N-labeled samples. $^1$H, $^{13}$C and $^{15}$N backbone resonances were assigned using the triple resonance experiments HNCA and CBCA(CO)NH and 3D $^{15}$N-resolved [$^1$H, $^1$H]-NOESY experiments. The side chain signals were assigned from HCCH-COSY and $^{13}$C-resolved [$^1$H, $^1$H]-NOESY experiments. Aromatic side chain assignments were obtained with 2D DQF-COSY, 2D [$^1$H, $^1$H]-NOESY in D$_2$O and 3D $^1$H-TOCSY-relayed ct-[$^{13}$C, $^1$H,]-HMQC experiments. Distance constraints for the calculation of the 3D structure were derived from 3D $^{13}$C-, $^{15}$N-resolved [$^1$H, $^1$H]-NOESY and 2D [$^1$H, $^1$H]-NOESY spectra recorded with a mixing time of 80 ms.

Example 2

Structure Determination

3881 NOEs are observed in the NOESY spectra leading to 1089 meaningful distance restraints and 362 angle restraints (Table 2). These structural restraints were used as an input for the structure calculation with the program CYANA, followed by restrained energy minimization using the program INSIGHT. A total of 100 conformers were initially generated by CYANA and the bundle of 20 conformers with the lowest target function is used to represent the three-dimensional NMR structure. The small residual constraint violations in the 20 refined conformers and the good coincidence of experimental NOEs and short interatomic distances show that the input data represent a self-consistent set, and that the restraints are well satisfied in the calculated conformers (Table 2). The deviations from ideal geometry are minimal, and similar energy values were obtained for all 20 conformers. The quality of the structures determined is reflected by the small backbone RMSD values relative to the mean coordinates of residues 58-83 and 99-113 of ~0.8 Å (see Table 2 and FIG. 1B). The bundle of 20 conformers representing the NMR structure is deposited in the PDB database with accession code 1U34, which is incorporated herein by reference in its entirety. The a set atomic coordinates for a representative conformer is provided in Table 3.

Chemical shift perturbation experiments. [$^{15}$N, $^1$H]-HMQC experiments of 0.05 mM ECD$_1$-CRFR2β in 10 mM BisTris(HCl), 95% H$_2$O/5% D$_2$O at pH 5 were measured in the absence and presence of an equimolar concentration of either astressin or CRF. Backbone assignment at pH 5 has been achieved following pH-dependent chemical shift changes of the cross-peaks in a series of [$^{15}$N, $^1$H]-HMQC experiments measured at pH 7, 6.5, 5.5 and 5. The assignment was then verified by the measurement of an HNCA experiment at pH 5.

TABLE 2

| Parameters characterizing the NMR structure of ECD$_1$-CRFR2β | |
|---|---|
| Number of distance constraints | 1089 |
| Number of dihedral angle constraints | 362 |
| Average upper limit distance constraint violations | 1.88 ± 0.94 Å |
| Average dihedral angle constraint violations | 11.8 ± 10.3 |
| Intra-protein energy after minimization[1] (kcal mol$^{-1}$) | −2092.3 ± 49.8 |
| Coordinate precision (Å) residues 58-83, 99-113 | |
| R.m.s.d[2] to the mean for N, C$^\square$ and C' | 0.81 ± 0.20 Å |
| R.m.s.d to the mean for all the heavy atoms | 1.30 ± 0.25 Å |
| Structural quality—Ramachandran plot[3] (%) | |
| Percentage in most favored region | 54.9 ± 2.57 |
| Percentage in the allowed region | 31.9 ± 2.29 |
| Percentage in the additionally allowed region | 7.4 ± 1.62 |
| Percentage in the disallowed region[4] | 4.8 ± 1.09 |

The parameters are given for an ensemble of twenty lowest-energy conformers (out of 100 structures calculated); None of these final structures exhibit NOE-derived violations greater than 0.2 Å or dihedral angle restraint violations greater than 5°.
[1]The cyana structures were parameterized with the cff91 force field. The minimizations were conducted in vacuum for 500 steps of conjugate gradient minimization using InsightII.
[2]R.m.s.d—Root mean square deviation;
[3]Structure quality was analyzed using PROCHECK;
[4]Most of the angles in the disallowed region are in the disordered region.

TABLE 3

The atomic coordinates for a representative conformer (without Hydrogens)(SEQ ID NO: 39).

| ATOM | 1 | N | GLY | A | 15 | 8.551 | −42.265 | 12.281 | 1.00 | 0.00 | N |
|---|---|---|---|---|---|---|---|---|---|---|---|
| ATOM | 2 | CA | GLY | A | 15 | 8.834 | −40.964 | 11.698 | 1.00 | 0.00 | C |
| ATOM | 3 | C | GLY | A | 15 | 8.059 | −39.859 | 12.420 | 1.00 | 0.00 | C |
| ATOM | 4 | O | GLY | A | 15 | 7.517 | −40.082 | 13.502 | 1.00 | 0.00 | O |
| ATOM | 5 | N | SER | A | 16 | 8.032 | −38.693 | 11.792 | 1.00 | 0.00 | N |
| ATOM | 6 | CA | SER | A | 16 | 7.333 | −37.554 | 12.362 | 1.00 | 0.00 | C |
| ATOM | 7 | C | SER | A | 16 | 6.933 | −36.578 | 11.253 | 1.00 | 0.00 | C |
| ATOM | 8 | O | SER | A | 16 | 7.357 | −36.726 | 10.108 | 1.00 | 0.00 | O |
| ATOM | 9 | CB | SER | A | 16 | 8.196 | −36.844 | 13.406 | 1.00 | 0.00 | C |
| ATOM | 10 | OG | SER | A | 16 | 7.448 | −36.492 | 14.567 | 1.00 | 0.00 | O |
| ATOM | 11 | N | GLY | A | 17 | 6.120 | −35.602 | 11.632 | 1.00 | 0.00 | N |
| ATOM | 12 | CA | GLY | A | 17 | 5.657 | −34.603 | 10.684 | 1.00 | 0.00 | C |
| ATOM | 13 | C | GLY | A | 17 | 5.802 | −33.193 | 11.260 | 1.00 | 0.00 | C |
| ATOM | 14 | O | GLY | A | 17 | 4.806 | −32.527 | 11.537 | 1.00 | 0.00 | O |
| ATOM | 15 | N | MET | A | 18 | 7.051 | −32.780 | 11.422 | 1.00 | 0.00 | N |
| ATOM | 16 | CA | MET | A | 18 | 7.338 | −31.461 | 11.959 | 1.00 | 0.00 | C |
| ATOM | 17 | C | MET | A | 18 | 8.820 | −31.115 | 11.800 | 1.00 | 0.00 | C |
| ATOM | 18 | O | MET | A | 18 | 9.681 | −31.765 | 12.391 | 1.00 | 0.00 | O |
| ATOM | 19 | CB | MET | A | 18 | 6.963 | −31.421 | 13.443 | 1.00 | 0.00 | C |

TABLE 3-continued

The atomic coordinates for a representative conformer (without Hydrogens)(SEQ ID NO: 39).

| ATOM | 20 | CG | MET | A | 18 | 6.524 | −30.015 | 13.859 | 1.00 | 0.00 | C |
|---|---|---|---|---|---|---|---|---|---|---|---|
| ATOM | 21 | SD | MET | A | 18 | 5.434 | −30.108 | 15.268 | 1.00 | 0.00 | S |
| ATOM | 22 | CE | MET | A | 18 | 5.104 | −28.373 | 15.520 | 1.00 | 0.00 | C |
| ATOM | 23 | N | LYS | A | 19 | 9.072 | −30.093 | 10.996 | 1.00 | 0.00 | N |
| ATOM | 24 | CA | LYS | A | 19 | 10.435 | −29.652 | 10.749 | 1.00 | 0.00 | C |
| ATOM | 25 | C | LYS | A | 19 | 10.416 | −28.460 | 9.789 | 1.00 | 0.00 | C |
| ATOM | 26 | O | LYS | A | 19 | 9.350 | −28.015 | 9.368 | 1.00 | 0.00 | O |
| ATOM | 27 | CB | LYS | A | 19 | 11.296 | −30.819 | 10.264 | 1.00 | 0.00 | C |
| ATOM | 28 | CG | LYS | A | 19 | 12.505 | −31.027 | 11.178 | 1.00 | 0.00 | C |
| ATOM | 29 | CD | LYS | A | 19 | 13.464 | −32.065 | 10.592 | 1.00 | 0.00 | C |
| ATOM | 30 | CE | LYS | A | 19 | 14.226 | −31.493 | 9.394 | 1.00 | 0.00 | C |
| ATOM | 31 | NZ | LYS | A | 19 | 15.141 | −30.413 | 9.830 | 1.00 | 0.00 | N |
| ATOM | 32 | N | GLU | A | 20 | 11.609 | −27.978 | 9.472 | 1.00 | 0.00 | N |
| ATOM | 33 | CA | GLU | A | 20 | 11.743 | −26.848 | 8.569 | 1.00 | 0.00 | C |
| ATOM | 34 | C | GLU | A | 20 | 11.132 | −25.593 | 9.197 | 1.00 | 0.00 | C |
| ATOM | 35 | O | GLU | A | 20 | 9.918 | −25.517 | 9.386 | 1.00 | 0.00 | O |
| ATOM | 36 | CB | GLU | A | 20 | 11.103 | −27.150 | 7.213 | 1.00 | 0.00 | C |
| ATOM | 37 | CG | GLU | A | 20 | 12.148 | −27.646 | 6.212 | 1.00 | 0.00 | C |
| ATOM | 38 | CD | GLU | A | 20 | 11.851 | −29.084 | 5.778 | 1.00 | 0.00 | C |
| ATOM | 39 | OE1 | GLU | A | 20 | 11.811 | −29.309 | 4.549 | 1.00 | 0.00 | O |
| ATOM | 40 | OE2 | GLU | A | 20 | 11.671 | −29.925 | 6.685 | 1.00 | 0.00 | O |
| ATOM | 41 | N | THR | A | 21 | 12.000 | −24.640 | 9.501 | 1.00 | 0.00 | N |
| ATOM | 42 | CA | THR | A | 21 | 11.561 | −23.392 | 10.102 | 1.00 | 0.00 | C |
| ATOM | 43 | C | THR | A | 21 | 12.744 | −22.436 | 10.270 | 1.00 | 0.00 | C |
| ATOM | 44 | O | THR | A | 21 | 13.864 | −22.869 | 10.535 | 1.00 | 0.00 | O |
| ATOM | 45 | CB | THR | A | 21 | 10.857 | −23.725 | 11.420 | 1.00 | 0.00 | C |
| ATOM | 46 | CG2 | THR | A | 21 | 11.716 | −24.592 | 12.341 | 1.00 | 0.00 | C |
| ATOM | 47 | OG1 | THR | A | 21 | 10.777 | −22.473 | 12.097 | 1.00 | 0.00 | O |
| ATOM | 48 | N | ALA | A | 22 | 12.454 | −21.153 | 10.109 | 1.00 | 0.00 | N |
| ATOM | 49 | CA | ALA | A | 22 | 13.479 | −20.132 | 10.239 | 1.00 | 0.00 | C |
| ATOM | 50 | C | ALA | A | 22 | 12.816 | −18.781 | 10.515 | 1.00 | 0.00 | C |
| ATOM | 51 | O | ALA | A | 22 | 11.611 | −18.627 | 10.323 | 1.00 | 0.00 | O |
| ATOM | 52 | CB | ALA | A | 22 | 14.343 | −20.112 | 8.977 | 1.00 | 0.00 | C |
| ATOM | 53 | N | ALA | A | 23 | 13.632 | −17.837 | 10.958 | 1.00 | 0.00 | N |
| ATOM | 54 | CA | ALA | A | 23 | 13.139 | −16.503 | 11.261 | 1.00 | 0.00 | C |
| ATOM | 55 | C | ALA | A | 23 | 14.310 | −15.616 | 11.687 | 1.00 | 0.00 | C |
| ATOM | 56 | O | ALA | A | 23 | 15.221 | −16.072 | 12.377 | 1.00 | 0.00 | O |
| ATOM | 57 | CB | ALA | A | 23 | 12.053 | −16.592 | 12.335 | 1.00 | 0.00 | C |
| ATOM | 58 | N | ALA | A | 24 | 14.250 | −14.364 | 11.257 | 1.00 | 0.00 | N |
| ATOM | 59 | CA | ALA | A | 24 | 15.294 | −13.408 | 11.584 | 1.00 | 0.00 | C |
| ATOM | 60 | C | ALA | A | 24 | 14.857 | −12.010 | 11.144 | 1.00 | 0.00 | C |
| ATOM | 61 | O | ALA | A | 24 | 14.647 | −11.767 | 9.956 | 1.00 | 0.00 | O |
| ATOM | 62 | CB | ALA | A | 24 | 16.607 | −13.843 | 10.930 | 1.00 | 0.00 | C |
| ATOM | 63 | N | LYS | A | 25 | 14.733 | −11.127 | 12.124 | 1.00 | 0.00 | N |
| ATOM | 64 | CA | LYS | A | 25 | 14.325 | −9.759 | 11.851 | 1.00 | 0.00 | C |
| ATOM | 65 | C | LYS | A | 25 | 15.365 | −8.797 | 12.427 | 1.00 | 0.00 | C |
| ATOM | 66 | O | LYS | A | 25 | 16.392 | −9.228 | 12.951 | 1.00 | 0.00 | O |
| ATOM | 67 | CB | LYS | A | 25 | 12.906 | −9.512 | 12.367 | 1.00 | 0.00 | C |
| ATOM | 68 | CG | LYS | A | 25 | 11.890 | −9.566 | 11.224 | 1.00 | 0.00 | C |
| ATOM | 69 | CD | LYS | A | 25 | 10.713 | −10.475 | 11.581 | 1.00 | 0.00 | C |
| ATOM | 70 | CE | LYS | A | 25 | 9.585 | −10.339 | 10.556 | 1.00 | 0.00 | C |
| ATOM | 71 | NZ | LYS | A | 25 | 8.430 | −11.181 | 10.940 | 1.00 | 0.00 | N |
| ATOM | 72 | N | PHE | A | 26 | 15.065 | −7.512 | 12.310 | 1.00 | 0.00 | N |
| ATOM | 73 | CA | PHE | A | 26 | 15.962 | −6.485 | 12.813 | 1.00 | 0.00 | C |
| ATOM | 74 | C | PHE | A | 26 | 15.191 | −5.419 | 13.595 | 1.00 | 0.00 | C |
| ATOM | 75 | O | PHE | A | 26 | 13.969 | −5.329 | 13.489 | 1.00 | 0.00 | O |
| ATOM | 76 | CB | PHE | A | 26 | 16.620 | −5.832 | 11.596 | 1.00 | 0.00 | C |
| ATOM | 77 | CG | PHE | A | 26 | 17.341 | −6.817 | 10.675 | 1.00 | 0.00 | C |
| ATOM | 78 | CD1 | PHE | A | 26 | 16.693 | −7.343 | 9.601 | 1.00 | 0.00 | C |
| ATOM | 79 | CD2 | PHE | A | 26 | 18.630 | −7.168 | 10.930 | 1.00 | 0.00 | C |
| ATOM | 80 | CE1 | PHE | A | 26 | 17.362 | −8.258 | 8.746 | 1.00 | 0.00 | C |
| ATOM | 81 | CE2 | PHE | A | 26 | 19.300 | −8.083 | 10.074 | 1.00 | 0.00 | C |
| ATOM | 82 | CZ | PHE | A | 26 | 18.652 | −8.608 | 9.000 | 1.00 | 0.00 | C |
| ATOM | 83 | N | GLU | A | 27 | 15.938 | −4.639 | 14.362 | 1.00 | 0.00 | N |
| ATOM | 84 | CA | GLU | A | 27 | 15.340 | −3.582 | 15.161 | 1.00 | 0.00 | C |
| ATOM | 85 | C | GLU | A | 27 | 14.447 | −2.697 | 14.288 | 1.00 | 0.00 | C |
| ATOM | 86 | O | GLU | A | 27 | 14.856 | −2.268 | 13.211 | 1.00 | 0.00 | O |
| ATOM | 87 | CB | GLU | A | 27 | 16.415 | −2.752 | 15.865 | 1.00 | 0.00 | C |
| ATOM | 88 | CG | GLU | A | 27 | 16.599 | −3.208 | 17.313 | 1.00 | 0.00 | C |
| ATOM | 89 | CD | GLU | A | 27 | 17.302 | −2.131 | 18.143 | 1.00 | 0.00 | C |
| ATOM | 90 | OE1 | GLU | A | 27 | 16.852 | −0.969 | 18.063 | 1.00 | 0.00 | O |
| ATOM | 91 | OE2 | GLU | A | 27 | 18.275 | −2.496 | 18.838 | 1.00 | 0.00 | O |
| ATOM | 92 | N | ARG | A | 28 | 13.246 | −2.449 | 14.788 | 1.00 | 0.00 | N |
| ATOM | 93 | CA | ARG | A | 28 | 12.292 | −1.622 | 14.067 | 1.00 | 0.00 | C |
| ATOM | 94 | C | ARG | A | 28 | 11.089 | −1.302 | 14.957 | 1.00 | 0.00 | C |
| ATOM | 95 | O | ARG | A | 28 | 10.303 | −2.190 | 15.286 | 1.00 | 0.00 | O |
| ATOM | 96 | CB | ARG | A | 28 | 11.807 | −2.322 | 12.798 | 1.00 | 0.00 | C |

TABLE 3-continued

The atomic coordinates for a representative conformer (without Hydrogens)(SEQ ID NO: 39).

| ATOM | 97 | CG | ARG | A | 28 | 12.279 | −1.578 | 11.547 | 1.00 | 0.00 | C |
|---|---|---|---|---|---|---|---|---|---|---|---|
| ATOM | 98 | CD | ARG | A | 28 | 13.298 | −2.411 | 10.766 | 1.00 | 0.00 | C |
| ATOM | 99 | NE | ARG | A | 28 | 12.615 | −3.176 | 9.700 | 1.00 | 0.00 | N |
| ATOM | 100 | CZ | ARG | A | 28 | 13.248 | −3.940 | 8.799 | 1.00 | 0.00 | C |
| ATOM | 101 | NH1 | ARG | A | 28 | 14.584 | −4.045 | 8.831 | 1.00 | 0.00 | N |
| ATOM | 102 | NH2 | ARG | A | 28 | 12.547 | −4.600 | 7.867 | 1.00 | 0.00 | N |
| ATOM | 103 | N | GLN | A | 29 | 10.983 | −0.033 | 15.320 | 1.00 | 0.00 | N |
| ATOM | 104 | CA | GLN | A | 29 | 9.889 | 0.415 | 16.166 | 1.00 | 0.00 | C |
| ATOM | 105 | C | GLN | A | 29 | 9.025 | 1.434 | 15.420 | 1.00 | 0.00 | C |
| ATOM | 106 | O | GLN | A | 29 | 7.835 | 1.205 | 15.203 | 1.00 | 0.00 | O |
| ATOM | 107 | CB | GLN | A | 29 | 10.413 | 0.998 | 17.479 | 1.00 | 0.00 | C |
| ATOM | 108 | CG | GLN | A | 29 | 9.639 | 0.439 | 18.674 | 1.00 | 0.00 | C |
| ATOM | 109 | CD | GLN | A | 29 | 10.260 | 0.901 | 19.994 | 1.00 | 0.00 | C |
| ATOM | 110 | NE2 | GLN | A | 29 | 9.979 | 2.161 | 20.313 | 1.00 | 0.00 | N |
| ATOM | 111 | OE1 | GLN | A | 29 | 10.950 | 0.163 | 20.678 | 1.00 | 0.00 | O |
| ATOM | 112 | N | HIS | A | 30 | 9.657 | 2.538 | 15.046 | 1.00 | 0.00 | N |
| ATOM | 113 | CA | HIS | A | 30 | 8.961 | 3.592 | 14.329 | 1.00 | 0.00 | C |
| ATOM | 114 | C | HIS | A | 30 | 9.951 | 4.695 | 13.950 | 1.00 | 0.00 | C |
| ATOM | 115 | O | HIS | A | 30 | 10.992 | 4.845 | 14.588 | 1.00 | 0.00 | O |
| ATOM | 116 | CB | HIS | A | 30 | 7.777 | 4.114 | 15.144 | 1.00 | 0.00 | C |
| ATOM | 117 | CG | HIS | A | 30 | 6.641 | 4.647 | 14.306 | 1.00 | 0.00 | C |
| ATOM | 118 | CD2 | HIS | A | 30 | 6.515 | 5.817 | 13.615 | 1.00 | 0.00 | C |
| ATOM | 119 | ND1 | HIS | A | 30 | 5.461 | 3.949 | 14.109 | 1.00 | 0.00 | N |
| ATOM | 120 | CE1 | HIS | A | 30 | 4.670 | 4.675 | 13.333 | 1.00 | 0.00 | C |
| ATOM | 121 | NE2 | HIS | A | 30 | 5.325 | 5.831 | 13.028 | 1.00 | 0.00 | N |
| ATOM | 122 | N | MET | A | 31 | 9.593 | 5.438 | 12.914 | 1.00 | 0.00 | N |
| ATOM | 123 | CA | MET | A | 31 | 10.437 | 6.523 | 12.442 | 1.00 | 0.00 | C |
| ATOM | 124 | C | MET | A | 31 | 10.041 | 7.849 | 13.095 | 1.00 | 0.00 | C |
| ATOM | 125 | O | MET | A | 31 | 10.107 | 8.901 | 12.462 | 1.00 | 0.00 | O |
| ATOM | 126 | CB | MET | A | 31 | 10.312 | 6.645 | 10.923 | 1.00 | 0.00 | C |
| ATOM | 127 | CG | MET | A | 31 | 8.979 | 7.287 | 10.532 | 1.00 | 0.00 | C |
| ATOM | 128 | SD | MET | A | 31 | 8.180 | 6.314 | 9.268 | 1.00 | 0.00 | S |
| ATOM | 129 | CE | MET | A | 31 | 6.655 | 7.226 | 9.093 | 1.00 | 0.00 | C |
| ATOM | 130 | N | ASP | A | 32 | 9.638 | 7.756 | 14.354 | 1.00 | 0.00 | N |
| ATOM | 131 | CA | ASP | A | 32 | 9.233 | 8.935 | 15.100 | 1.00 | 0.00 | C |
| ATOM | 132 | C | ASP | A | 32 | 8.026 | 9.577 | 14.411 | 1.00 | 0.00 | C |
| ATOM | 133 | O | ASP | A | 32 | 7.908 | 9.533 | 13.188 | 1.00 | 0.00 | O |
| ATOM | 134 | CB | ASP | A | 32 | 10.356 | 9.970 | 15.147 | 1.00 | 0.00 | C |
| ATOM | 135 | CG | ASP | A | 32 | 10.027 | 11.247 | 15.923 | 1.00 | 0.00 | C |
| ATOM | 136 | OD1 | ASP | A | 32 | 9.600 | 11.108 | 17.089 | 1.00 | 0.00 | O |
| ATOM | 137 | OD2 | ASP | A | 32 | 10.210 | 12.334 | 15.333 | 1.00 | 0.00 | O |
| ATOM | 138 | N | SER | A | 33 | 7.159 | 10.158 | 15.228 | 1.00 | 0.00 | N |
| ATOM | 139 | CA | SER | A | 33 | 5.966 | 10.808 | 14.714 | 1.00 | 0.00 | C |
| ATOM | 140 | C | SER | A | 33 | 5.002 | 11.116 | 15.861 | 1.00 | 0.00 | C |
| ATOM | 141 | O | SER | A | 33 | 5.007 | 10.431 | 16.881 | 1.00 | 0.00 | O |
| ATOM | 142 | CB | SER | A | 33 | 5.277 | 9.940 | 13.660 | 1.00 | 0.00 | C |
| ATOM | 143 | OG | SER | A | 33 | 5.713 | 10.254 | 12.341 | 1.00 | 0.00 | O |
| ATOM | 144 | N | PRO | A | 34 | 4.177 | 12.177 | 15.650 | 1.00 | 0.00 | N |
| ATOM | 145 | CA | PRO | A | 34 | 3.209 | 12.584 | 16.654 | 1.00 | 0.00 | C |
| ATOM | 146 | C | PRO | A | 34 | 2.020 | 11.622 | 16.692 | 1.00 | 0.00 | C |
| ATOM | 147 | O | PRO | A | 34 | 2.107 | 10.502 | 16.190 | 1.00 | 0.00 | O |
| ATOM | 148 | CB | PRO | A | 34 | 2.816 | 14.001 | 16.269 | 1.00 | 0.00 | C |
| ATOM | 149 | CG | PRO | A | 34 | 3.220 | 14.165 | 14.812 | 1.00 | 0.00 | C |
| ATOM | 150 | CD | PRO | A | 34 | 4.143 | 13.012 | 14.453 | 1.00 | 0.00 | C |
| ATOM | 151 | N | ASP | A | 35 | 0.937 | 12.095 | 17.291 | 1.00 | 0.00 | N |
| ATOM | 152 | CA | ASP | A | 35 | −0.268 | 11.290 | 17.400 | 1.00 | 0.00 | C |
| ATOM | 153 | C | ASP | A | 35 | −1.330 | 11.837 | 16.444 | 1.00 | 0.00 | C |
| ATOM | 154 | O | ASP | A | 35 | −1.391 | 13.041 | 16.202 | 1.00 | 0.00 | O |
| ATOM | 155 | CB | ASP | A | 35 | −0.838 | 11.343 | 18.819 | 1.00 | 0.00 | C |
| ATOM | 156 | CG | ASP | A | 35 | −2.185 | 10.640 | 19.002 | 1.00 | 0.00 | C |
| ATOM | 157 | OD1 | ASP | A | 35 | −2.203 | 9.632 | 19.741 | 1.00 | 0.00 | O |
| ATOM | 158 | OD2 | ASP | A | 35 | −3.165 | 11.127 | 18.398 | 1.00 | 0.00 | O |
| ATOM | 159 | N | LEU | A | 36 | −2.140 | 10.926 | 15.927 | 1.00 | 0.00 | N |
| ATOM | 160 | CA | LEU | A | 36 | −3.196 | 11.301 | 15.002 | 1.00 | 0.00 | C |
| ATOM | 161 | C | LEU | A | 36 | −2.615 | 11.414 | 13.590 | 1.00 | 0.00 | C |
| ATOM | 162 | O | LEU | A | 36 | −3.138 | 10.817 | 12.650 | 1.00 | 0.00 | O |
| ATOM | 163 | CB | LEU | A | 36 | −3.901 | 12.572 | 15.481 | 1.00 | 0.00 | C |
| ATOM | 164 | CG | LEU | A | 36 | −5.429 | 12.548 | 15.435 | 1.00 | 0.00 | C |
| ATOM | 165 | CD1 | LEU | A | 36 | −6.022 | 13.622 | 16.351 | 1.00 | 0.00 | C |
| ATOM | 166 | CD2 | LEU | A | 36 | −5.937 | 12.678 | 13.998 | 1.00 | 0.00 | C |
| ATOM | 167 | N | GLY | A | 37 | −1.543 | 12.186 | 13.486 | 1.00 | 0.00 | N |
| ATOM | 168 | CA | GLY | A | 37 | −0.886 | 12.384 | 12.206 | 1.00 | 0.00 | C |
| ATOM | 169 | C | GLY | A | 37 | −0.860 | 13.867 | 11.828 | 1.00 | 0.00 | C |
| ATOM | 170 | O | GLY | A | 37 | −1.889 | 14.540 | 11.866 | 1.00 | 0.00 | O |
| ATOM | 171 | N | THR | A | 38 | 0.328 | 14.333 | 11.472 | 1.00 | 0.00 | N |
| ATOM | 172 | CA | THR | A | 38 | 0.503 | 15.724 | 11.088 | 1.00 | 0.00 | C |
| ATOM | 173 | C | THR | A | 38 | 0.080 | 15.932 | 9.633 | 1.00 | 0.00 | C |

TABLE 3-continued

The atomic coordinates for a representative conformer (without Hydrogens)(SEQ ID NO: 39).

| ATOM | 174 | O | THR | A | 38 | 0.192 | 17.035 | 9.101 | 1.00 | 0.00 | O |
|------|-----|-----|-----|---|----|-------|--------|-------|------|------|---|
| ATOM | 175 | CB | THR | A | 38 | 1.958 | 16.110 | 11.359 | 1.00 | 0.00 | C |
| ATOM | 176 | CG2 | THR | A | 38 | 2.925 | 15.498 | 10.344 | 1.00 | 0.00 | C |
| ATOM | 177 | OG1 | THR | A | 38 | 2.003 | 17.507 | 11.083 | 1.00 | 0.00 | O |
| ATOM | 178 | N | THR | A | 39 | −0.399 | 14.853 | 9.029 | 1.00 | 0.00 | N |
| ATOM | 179 | CA | THR | A | 39 | −0.839 | 14.905 | 7.645 | 1.00 | 0.00 | C |
| ATOM | 180 | C | THR | A | 39 | −1.474 | 13.573 | 7.239 | 1.00 | 0.00 | C |
| ATOM | 181 | O | THR | A | 39 | −0.852 | 12.520 | 7.364 | 1.00 | 0.00 | O |
| ATOM | 182 | CB | THR | A | 39 | 0.362 | 15.293 | 6.780 | 1.00 | 0.00 | C |
| ATOM | 183 | CG2 | THR | A | 39 | 1.397 | 14.171 | 6.679 | 1.00 | 0.00 | C |
| ATOM | 184 | OG1 | THR | A | 39 | −0.175 | 15.391 | 5.464 | 1.00 | 0.00 | O |
| ATOM | 185 | N | LEU | A | 40 | −2.707 | 13.665 | 6.762 | 1.00 | 0.00 | N |
| ATOM | 186 | CA | LEU | A | 40 | −3.434 | 12.480 | 6.336 | 1.00 | 0.00 | C |
| ATOM | 187 | C | LEU | A | 40 | −2.798 | 11.927 | 5.059 | 1.00 | 0.00 | C |
| ATOM | 188 | O | LEU | A | 40 | −2.238 | 12.681 | 4.265 | 1.00 | 0.00 | O |
| ATOM | 189 | CB | LEU | A | 40 | −4.926 | 12.789 | 6.196 | 1.00 | 0.00 | C |
| ATOM | 190 | CG | LEU | A | 40 | −5.318 | 13.680 | 5.015 | 1.00 | 0.00 | C |
| ATOM | 191 | CD1 | LEU | A | 40 | −6.657 | 13.242 | 4.419 | 1.00 | 0.00 | C |
| ATOM | 192 | CD2 | LEU | A | 40 | −5.326 | 15.155 | 5.420 | 1.00 | 0.00 | C |
| ATOM | 193 | N | LEU | A | 41 | −2.905 | 10.616 | 4.903 | 1.00 | 0.00 | N |
| ATOM | 194 | CA | LEU | A | 41 | −2.347 | 9.954 | 3.737 | 1.00 | 0.00 | C |
| ATOM | 195 | C | LEU | A | 41 | −3.380 | 9.960 | 2.608 | 1.00 | 0.00 | C |
| ATOM | 196 | O | LEU | A | 41 | −3.144 | 9.395 | 1.542 | 1.00 | 0.00 | O |
| ATOM | 197 | CB | LEU | A | 41 | −1.845 | 8.555 | 4.103 | 1.00 | 0.00 | C |
| ATOM | 198 | CG | LEU | A | 41 | −1.060 | 8.446 | 5.412 | 1.00 | 0.00 | C |
| ATOM | 199 | CD1 | LEU | A | 41 | −1.145 | 7.030 | 5.985 | 1.00 | 0.00 | C |
| ATOM | 200 | CD2 | LEU | A | 41 | 0.388 | 8.901 | 5.222 | 1.00 | 0.00 | C |
| ATOM | 201 | N | GLU | A | 42 | −4.504 | 10.606 | 2.882 | 1.00 | 0.00 | N |
| ATOM | 202 | CA | GLU | A | 42 | −5.575 | 10.693 | 1.905 | 1.00 | 0.00 | C |
| ATOM | 203 | C | GLU | A | 42 | −5.884 | 12.158 | 1.585 | 1.00 | 0.00 | C |
| ATOM | 204 | O | GLU | A | 42 | −7.034 | 12.512 | 1.331 | 1.00 | 0.00 | O |
| ATOM | 205 | CB | GLU | A | 42 | −6.826 | 9.964 | 2.394 | 1.00 | 0.00 | C |
| ATOM | 206 | CG | GLU | A | 42 | −7.849 | 9.810 | 1.266 | 1.00 | 0.00 | C |
| ATOM | 207 | CD | GLU | A | 42 | −7.176 | 9.335 | −0.024 | 1.00 | 0.00 | C |
| ATOM | 208 | OE1 | GLU | A | 42 | −6.762 | 10.217 | −0.806 | 1.00 | 0.00 | O |
| ATOM | 209 | OE2 | GLU | A | 42 | −7.092 | 8.100 | −0.197 | 1.00 | 0.00 | O |
| ATOM | 210 | N | GLN | A | 43 | −4.837 | 12.969 | 1.607 | 1.00 | 0.00 | N |
| ATOM | 211 | CA | GLN | A | 43 | −4.981 | 14.386 | 1.324 | 1.00 | 0.00 | C |
| ATOM | 212 | C | GLN | A | 43 | −5.997 | 14.601 | 0.200 | 1.00 | 0.00 | C |
| ATOM | 213 | O | GLN | A | 43 | −6.846 | 15.486 | 0.287 | 1.00 | 0.00 | O |
| ATOM | 214 | CB | GLN | A | 43 | −3.632 | 15.016 | 0.971 | 1.00 | 0.00 | C |
| ATOM | 215 | CG | GLN | A | 43 | −2.746 | 14.026 | 0.213 | 1.00 | 0.00 | C |
| ATOM | 216 | CD | GLN | A | 43 | −1.607 | 13.518 | 1.099 | 1.00 | 0.00 | C |
| ATOM | 217 | NE2 | GLN | A | 43 | −1.575 | 12.195 | 1.233 | 1.00 | 0.00 | N |
| ATOM | 218 | OE1 | GLN | A | 43 | −0.810 | 14.276 | 1.625 | 1.00 | 0.00 | O |
| ATOM | 219 | N | TYR | A | 44 | −5.874 | 13.776 | −0.831 | 1.00 | 0.00 | N |
| ATOM | 220 | CA | TYR | A | 44 | −6.771 | 13.865 | −1.971 | 1.00 | 0.00 | C |
| ATOM | 221 | C | TYR | A | 44 | −6.482 | 12.756 | −2.983 | 1.00 | 0.00 | C |
| ATOM | 222 | O | TYR | A | 44 | −7.401 | 12.207 | −3.587 | 1.00 | 0.00 | O |
| ATOM | 223 | CB | TYR | A | 44 | −6.491 | 15.220 | −2.623 | 1.00 | 0.00 | C |
| ATOM | 224 | CG | TYR | A | 44 | −5.214 | 15.253 | −3.465 | 1.00 | 0.00 | C |
| ATOM | 225 | CD1 | TYR | A | 44 | −5.296 | 15.388 | −4.838 | 1.00 | 0.00 | C |
| ATOM | 226 | CD2 | TYR | A | 44 | −3.981 | 15.149 | −2.855 | 1.00 | 0.00 | C |
| ATOM | 227 | CE1 | TYR | A | 44 | −4.095 | 15.418 | −5.630 | 1.00 | 0.00 | C |
| ATOM | 228 | CE2 | TYR | A | 44 | −2.779 | 15.179 | −3.648 | 1.00 | 0.00 | C |
| ATOM | 229 | CZ | TYR | A | 44 | −2.896 | 15.313 | −4.997 | 1.00 | 0.00 | C |
| ATOM | 230 | OH | TYR | A | 44 | −1.761 | 15.342 | −5.746 | 1.00 | 0.00 | O |
| ATOM | 231 | N | CYS | A | 45 | −5.200 | 12.459 | −3.137 | 1.00 | 0.00 | N |
| ATOM | 232 | CA | CYS | A | 45 | −4.777 | 11.425 | −4.067 | 1.00 | 0.00 | C |
| ATOM | 233 | C | CYS | A | 45 | −5.206 | 11.841 | −5.476 | 1.00 | 0.00 | C |
| ATOM | 234 | O | CYS | A | 45 | −5.213 | 13.026 | −5.801 | 1.00 | 0.00 | O |
| ATOM | 235 | CB | CYS | A | 45 | −5.338 | 10.054 | −3.681 | 1.00 | 0.00 | C |
| ATOM | 236 | SG | CYS | A | 45 | −4.293 | 8.634 | −4.166 | 1.00 | 0.00 | S |
| ATOM | 237 | N | HIS | A | 46 | −5.554 | 10.842 | −6.273 | 1.00 | 0.00 | N |
| ATOM | 238 | CA | HIS | A | 46 | −5.983 | 11.088 | −7.639 | 1.00 | 0.00 | C |
| ATOM | 239 | C | HIS | A | 46 | −7.400 | 11.667 | −7.635 | 1.00 | 0.00 | C |
| ATOM | 240 | O | HIS | A | 46 | −7.897 | 12.093 | −6.594 | 1.00 | 0.00 | O |
| ATOM | 241 | CB | HIS | A | 46 | −5.863 | 9.818 | −8.484 | 1.00 | 0.00 | C |
| ATOM | 242 | CG | HIS | A | 46 | −4.996 | 9.976 | −9.710 | 1.00 | 0.00 | C |
| ATOM | 243 | CD2 | HIS | A | 46 | −5.189 | 9.568 | −10.997 | 1.00 | 0.00 | C |
| ATOM | 244 | ND1 | HIS | A | 46 | −3.770 | 10.617 | −9.683 | 1.00 | 0.00 | N |
| ATOM | 245 | CE1 | HIS | A | 46 | −3.257 | 10.591 | −10.905 | 1.00 | 0.00 | C |
| ATOM | 246 | NE2 | HIS | A | 46 | −4.139 | 9.941 | −11.718 | 1.00 | 0.00 | N |
| ATOM | 247 | N | ARG | A | 47 | −8.008 | 11.664 | −8.813 | 1.00 | 0.00 | N |
| ATOM | 248 | CA | ARG | A | 47 | −9.357 | 12.184 | −8.958 | 1.00 | 0.00 | C |
| ATOM | 249 | C | ARG | A | 47 | −10.315 | 11.444 | −8.022 | 1.00 | 0.00 | C |
| ATOM | 250 | O | ARG | A | 47 | −11.240 | 12.042 | −7.475 | 1.00 | 0.00 | O |

TABLE 3-continued

The atomic coordinates for a representative conformer (without Hydrogens)(SEQ ID NO: 39).

| ATOM | 251 | CB | ARG | A | 47 | −9.850 | 12.040 | −10.399 | 1.00 | 0.00 | C |
|---|---|---|---|---|---|---|---|---|---|---|---|
| ATOM | 252 | CG | ARG | A | 47 | −9.404 | 10.706 | −11.001 | 1.00 | 0.00 | C |
| ATOM | 253 | CD | ARG | A | 47 | −8.233 | 10.904 | −11.966 | 1.00 | 0.00 | C |
| ATOM | 254 | NE | ARG | A | 47 | −8.735 | 11.349 | −13.285 | 1.00 | 0.00 | N |
| ATOM | 255 | CZ | ARG | A | 47 | −7.946 | 11.652 | −14.325 | 1.00 | 0.00 | C |
| ATOM | 256 | NH1 | ARG | A | 47 | −6.615 | 11.561 | −14.206 | 1.00 | 0.00 | N |
| ATOM | 257 | NH2 | ARG | A | 47 | −8.489 | 12.047 | −15.485 | 1.00 | 0.00 | N |
| ATOM | 258 | N | THR | A | 48 | −10.060 | 10.153 | −7.868 | 1.00 | 0.00 | N |
| ATOM | 259 | CA | THR | A | 48 | −10.889 | 9.325 | −7.008 | 1.00 | 0.00 | C |
| ATOM | 260 | C | THR | A | 48 | −12.337 | 9.819 | −7.025 | 1.00 | 0.00 | C |
| ATOM | 261 | O | THR | A | 48 | −12.720 | 10.655 | −6.209 | 1.00 | 0.00 | O |
| ATOM | 262 | CB | THR | A | 48 | −10.264 | 9.320 | −5.612 | 1.00 | 0.00 | C |
| ATOM | 263 | CG2 | THR | A | 48 | −10.379 | 10.678 | −4.914 | 1.00 | 0.00 | C |
| ATOM | 264 | OG1 | THR | A | 48 | −11.116 | 8.467 | −4.853 | 1.00 | 0.00 | O |
| ATOM | 265 | N | THR | A | 49 | −13.102 | 9.281 | −7.962 | 1.00 | 0.00 | N |
| ATOM | 266 | CA | THR | A | 49 | −14.498 | 9.657 | −8.097 | 1.00 | 0.00 | C |
| ATOM | 267 | C | THR | A | 49 | −15.356 | 8.427 | −8.399 | 1.00 | 0.00 | C |
| ATOM | 268 | O | THR | A | 49 | −15.596 | 8.103 | −9.562 | 1.00 | 0.00 | O |
| ATOM | 269 | CB | THR | A | 49 | −14.596 | 10.744 | −9.169 | 1.00 | 0.00 | C |
| ATOM | 270 | CG2 | THR | A | 49 | −14.440 | 10.185 | −10.585 | 1.00 | 0.00 | C |
| ATOM | 271 | OG1 | THR | A | 49 | −15.954 | 11.169 | −9.110 | 1.00 | 0.00 | O |
| ATOM | 272 | N | ILE | A | 50 | −15.795 | 7.773 | −7.334 | 1.00 | 0.00 | N |
| ATOM | 273 | CA | ILE | A | 50 | −16.620 | 6.585 | −7.472 | 1.00 | 0.00 | C |
| ATOM | 274 | C | ILE | A | 50 | −17.143 | 6.171 | −6.095 | 1.00 | 0.00 | C |
| ATOM | 275 | O | ILE | A | 50 | −16.620 | 6.606 | −5.070 | 1.00 | 0.00 | O |
| ATOM | 276 | CB | ILE | A | 50 | −15.849 | 5.479 | −8.195 | 1.00 | 0.00 | C |
| ATOM | 277 | CG1 | ILE | A | 50 | −16.798 | 4.388 | −8.696 | 1.00 | 0.00 | C |
| ATOM | 278 | CG2 | ILE | A | 50 | −14.741 | 4.910 | −7.306 | 1.00 | 0.00 | C |
| ATOM | 279 | CD1 | ILE | A | 50 | −16.086 | 3.447 | −9.670 | 1.00 | 0.00 | C |
| ATOM | 280 | N | GLY | A | 51 | −18.170 | 5.334 | −6.115 | 1.00 | 0.00 | N |
| ATOM | 281 | CA | GLY | A | 51 | −18.770 | 4.857 | −4.881 | 1.00 | 0.00 | C |
| ATOM | 282 | C | GLY | A | 51 | −20.217 | 5.340 | −4.751 | 1.00 | 0.00 | C |
| ATOM | 283 | O | GLY | A | 51 | −20.565 | 6.013 | −3.783 | 1.00 | 0.00 | O |
| ATOM | 284 | N | ASN | A | 52 | −21.019 | 4.978 | −5.742 | 1.00 | 0.00 | N |
| ATOM | 285 | CA | ASN | A | 52 | −22.419 | 5.367 | −5.751 | 1.00 | 0.00 | C |
| ATOM | 286 | C | ASN | A | 52 | −22.523 | 6.878 | −5.962 | 1.00 | 0.00 | C |
| ATOM | 287 | O | ASN | A | 52 | −23.173 | 7.574 | −5.183 | 1.00 | 0.00 | O |
| ATOM | 288 | CB | ASN | A | 52 | −23.093 | 5.027 | −4.420 | 1.00 | 0.00 | C |
| ATOM | 289 | CG | ASN | A | 52 | −24.600 | 4.838 | −4.601 | 1.00 | 0.00 | C |
| ATOM | 290 | ND2 | ASN | A | 52 | −25.340 | 5.750 | −3.977 | 1.00 | 0.00 | N |
| ATOM | 291 | OD1 | ASN | A | 52 | −25.061 | 3.922 | −5.265 | 1.00 | 0.00 | O |
| ATOM | 292 | N | PHE | A | 53 | −21.872 | 7.343 | −7.018 | 1.00 | 0.00 | N |
| ATOM | 293 | CA | PHE | A | 53 | −21.882 | 8.760 | −7.341 | 1.00 | 0.00 | C |
| ATOM | 294 | C | PHE | A | 53 | −21.315 | 9.007 | −8.740 | 1.00 | 0.00 | C |
| ATOM | 295 | O | PHE | A | 53 | −21.839 | 9.832 | −9.489 | 1.00 | 0.00 | O |
| ATOM | 296 | CB | PHE | A | 53 | −20.992 | 9.459 | −6.312 | 1.00 | 0.00 | C |
| ATOM | 297 | CG | PHE | A | 53 | −21.229 | 10.967 | −6.209 | 1.00 | 0.00 | C |
| ATOM | 298 | CD1 | PHE | A | 53 | −20.764 | 11.797 | −7.181 | 1.00 | 0.00 | C |
| ATOM | 299 | CD2 | PHE | A | 53 | −21.903 | 11.479 | −5.144 | 1.00 | 0.00 | C |
| ATOM | 300 | CE1 | PHE | A | 53 | −20.983 | 13.196 | −7.085 | 1.00 | 0.00 | C |
| ATOM | 301 | CE2 | PHE | A | 53 | −22.122 | 12.879 | −5.048 | 1.00 | 0.00 | C |
| ATOM | 302 | CZ | PHE | A | 53 | −21.658 | 13.708 | −6.021 | 1.00 | 0.00 | C |
| ATOM | 303 | N | SER | A | 54 | −20.255 | 8.277 | −9.052 | 1.00 | 0.00 | N |
| ATOM | 304 | CA | SER | A | 54 | −19.611 | 8.408 | −10.348 | 1.00 | 0.00 | C |
| ATOM | 305 | C | SER | A | 54 | −18.854 | 7.123 | −10.688 | 1.00 | 0.00 | C |
| ATOM | 306 | O | SER | A | 54 | −17.629 | 7.074 | −10.585 | 1.00 | 0.00 | O |
| ATOM | 307 | CB | SER | A | 54 | −18.661 | 9.607 | −10.373 | 1.00 | 0.00 | C |
| ATOM | 308 | OG | SER | A | 54 | −19.173 | 10.677 | −11.164 | 1.00 | 0.00 | O |
| ATOM | 309 | N | GLY | A | 55 | −19.614 | 6.113 | −11.085 | 1.00 | 0.00 | N |
| ATOM | 310 | CA | GLY | A | 55 | −19.029 | 4.830 | −11.440 | 1.00 | 0.00 | C |
| ATOM | 311 | C | GLY | A | 55 | −19.156 | 4.568 | −12.942 | 1.00 | 0.00 | C |
| ATOM | 312 | O | GLY | A | 55 | −20.208 | 4.138 | −13.413 | 1.00 | 0.00 | O |
| ATOM | 313 | N | PRO | A | 56 | −18.041 | 4.843 | −13.671 | 1.00 | 0.00 | N |
| ATOM | 314 | CA | PRO | A | 56 | −18.019 | 4.641 | −15.109 | 1.00 | 0.00 | C |
| ATOM | 315 | C | PRO | A | 56 | −17.917 | 3.154 | −15.452 | 1.00 | 0.00 | C |
| ATOM | 316 | O | PRO | A | 56 | −18.851 | 2.574 | −16.002 | 1.00 | 0.00 | O |
| ATOM | 317 | CB | PRO | A | 56 | −16.828 | 5.447 | −15.601 | 1.00 | 0.00 | C |
| ATOM | 318 | CG | PRO | A | 56 | −15.957 | 5.691 | −14.379 | 1.00 | 0.00 | C |
| ATOM | 319 | CD | PRO | A | 56 | −16.778 | 5.354 | −13.146 | 1.00 | 0.00 | C |
| ATOM | 320 | N | TYR | A | 57 | −16.772 | 2.578 | −15.112 | 1.00 | 0.00 | N |
| ATOM | 321 | CA | TYR | A | 57 | −16.536 | 1.169 | −15.377 | 1.00 | 0.00 | C |
| ATOM | 322 | C | TYR | A | 57 | −16.228 | 0.413 | −14.084 | 1.00 | 0.00 | C |
| ATOM | 323 | O | TYR | A | 57 | −16.388 | 0.952 | −12.991 | 1.00 | 0.00 | O |
| ATOM | 324 | CB | TYR | A | 57 | −15.311 | 1.111 | −16.292 | 1.00 | 0.00 | C |
| ATOM | 325 | CG | TYR | A | 57 | −14.486 | 2.400 | −16.308 | 1.00 | 0.00 | C |
| ATOM | 326 | CD1 | TYR | A | 57 | −13.798 | 2.794 | −15.178 | 1.00 | 0.00 | C |
| ATOM | 327 | CD2 | TYR | A | 57 | −14.429 | 3.168 | −17.453 | 1.00 | 0.00 | C |

TABLE 3-continued

The atomic coordinates for a representative conformer (without Hydrogens)(SEQ ID NO: 39).

| ATOM | 328 | CE1 | TYR | A | 57 | −13.022 | 4.006 | −15.193 | 1.00 | 0.00 | C |
|---|---|---|---|---|---|---|---|---|---|---|---|
| ATOM | 329 | CE2 | TYR | A | 57 | −13.652 | 4.381 | −17.469 | 1.00 | 0.00 | C |
| ATOM | 330 | CZ | TYR | A | 57 | −12.987 | 4.739 | −16.337 | 1.00 | 0.00 | C |
| ATOM | 331 | OH | TYR | A | 57 | −12.253 | 5.886 | −16.353 | 1.00 | 0.00 | O |
| ATOM | 332 | N | THR | A | 58 | −15.791 | −0.828 | −14.251 | 1.00 | 0.00 | N |
| ATOM | 333 | CA | THR | A | 58 | −15.459 | −1.664 | −13.110 | 1.00 | 0.00 | C |
| ATOM | 334 | C | THR | A | 58 | −13.945 | −1.689 | −12.890 | 1.00 | 0.00 | C |
| ATOM | 335 | O | THR | A | 58 | −13.392 | −2.704 | −12.472 | 1.00 | 0.00 | O |
| ATOM | 336 | CB | THR | A | 58 | −16.061 | −3.050 | −13.350 | 1.00 | 0.00 | C |
| ATOM | 337 | CG2 | THR | A | 58 | −16.031 | −3.926 | −12.095 | 1.00 | 0.00 | C |
| ATOM | 338 | OG1 | THR | A | 58 | −17.446 | −2.795 | −13.563 | 1.00 | 0.00 | O |
| ATOM | 339 | N | TYR | A | 59 | −13.318 | −0.558 | −13.179 | 1.00 | 0.00 | N |
| ATOM | 340 | CA | TYR | A | 59 | −11.880 | −0.437 | −13.018 | 1.00 | 0.00 | C |
| ATOM | 341 | C | TYR | A | 59 | −11.511 | −0.207 | −11.551 | 1.00 | 0.00 | C |
| ATOM | 342 | O | TYR | A | 59 | −12.378 | 0.075 | −10.726 | 1.00 | 0.00 | O |
| ATOM | 343 | CB | TYR | A | 59 | −11.466 | 0.789 | −13.833 | 1.00 | 0.00 | C |
| ATOM | 344 | CG | TYR | A | 59 | −11.632 | 2.116 | −13.091 | 1.00 | 0.00 | C |
| ATOM | 345 | CD1 | TYR | A | 59 | −12.688 | 2.292 | −12.219 | 1.00 | 0.00 | C |
| ATOM | 346 | CD2 | TYR | A | 59 | −10.726 | 3.138 | −13.291 | 1.00 | 0.00 | C |
| ATOM | 347 | CE1 | TYR | A | 59 | −12.844 | 3.541 | −11.520 | 1.00 | 0.00 | C |
| ATOM | 348 | CE2 | TYR | A | 59 | −10.882 | 4.387 | −12.591 | 1.00 | 0.00 | C |
| ATOM | 349 | CZ | TYR | A | 59 | −11.934 | 4.526 | −11.740 | 1.00 | 0.00 | C |
| ATOM | 350 | OH | TYR | A | 59 | −12.082 | 5.706 | −11.080 | 1.00 | 0.00 | O |
| ATOM | 351 | N | CYS | A | 60 | −10.222 | −0.338 | −11.272 | 1.00 | 0.00 | N |
| ATOM | 352 | CA | CYS | A | 60 | −9.727 | −0.148 | −9.918 | 1.00 | 0.00 | C |
| ATOM | 353 | C | CYS | A | 60 | −9.928 | 1.320 | −9.535 | 1.00 | 0.00 | C |
| ATOM | 354 | O | CYS | A | 60 | −9.875 | 2.202 | −10.390 | 1.00 | 0.00 | O |
| ATOM | 355 | CB | CYS | A | 60 | −8.264 | −0.577 | −9.786 | 1.00 | 0.00 | C |
| ATOM | 356 | SG | CYS | A | 60 | −7.976 | −2.377 | −9.947 | 1.00 | 0.00 | S |
| ATOM | 357 | N | ASN | A | 61 | −10.154 | 1.535 | −8.247 | 1.00 | 0.00 | N |
| ATOM | 358 | CA | ASN | A | 61 | −10.362 | 2.881 | −7.740 | 1.00 | 0.00 | C |
| ATOM | 359 | C | ASN | A | 61 | −9.214 | 3.252 | −6.800 | 1.00 | 0.00 | C |
| ATOM | 360 | O | ASN | A | 61 | −8.479 | 2.379 | −6.338 | 1.00 | 0.00 | O |
| ATOM | 361 | CB | ASN | A | 61 | −11.669 | 2.975 | −6.949 | 1.00 | 0.00 | C |
| ATOM | 362 | CG | ASN | A | 61 | −11.940 | 4.415 | −6.507 | 1.00 | 0.00 | C |
| ATOM | 363 | ND2 | ASN | A | 61 | −11.927 | 5.297 | −7.502 | 1.00 | 0.00 | N |
| ATOM | 364 | OD1 | ASN | A | 61 | −12.149 | 4.705 | −5.341 | 1.00 | 0.00 | O |
| ATOM | 365 | N | THR | A | 62 | −9.093 | 4.546 | −6.545 | 1.00 | 0.00 | N |
| ATOM | 366 | CA | THR | A | 62 | −8.045 | 5.043 | −5.669 | 1.00 | 0.00 | C |
| ATOM | 367 | C | THR | A | 62 | −8.224 | 4.485 | −4.256 | 1.00 | 0.00 | C |
| ATOM | 368 | O | THR | A | 62 | −9.295 | 4.617 | −3.663 | 1.00 | 0.00 | O |
| ATOM | 369 | CB | THR | A | 62 | −8.065 | 6.571 | −5.727 | 1.00 | 0.00 | C |
| ATOM | 370 | CG2 | THR | A | 62 | −7.191 | 7.210 | −4.646 | 1.00 | 0.00 | C |
| ATOM | 371 | OG1 | THR | A | 62 | −7.394 | 6.881 | −6.945 | 1.00 | 0.00 | O |
| ATOM | 372 | N | THR | A | 63 | −7.161 | 3.874 | −3.756 | 1.00 | 0.00 | N |
| ATOM | 373 | CA | THR | A | 63 | −7.186 | 3.297 | −2.422 | 1.00 | 0.00 | C |
| ATOM | 374 | C | THR | A | 63 | −5.765 | 3.143 | −1.880 | 1.00 | 0.00 | C |
| ATOM | 375 | O | THR | A | 63 | −4.802 | 3.122 | −2.647 | 1.00 | 0.00 | O |
| ATOM | 376 | CB | THR | A | 63 | −7.955 | 1.976 | −2.494 | 1.00 | 0.00 | C |
| ATOM | 377 | CG2 | THR | A | 63 | −7.459 | 0.953 | −1.470 | 1.00 | 0.00 | C |
| ATOM | 378 | OG1 | THR | A | 63 | −9.264 | 2.312 | −2.043 | 1.00 | 0.00 | O |
| ATOM | 379 | N | LEU | A | 64 | −5.676 | 3.040 | −0.562 | 1.00 | 0.00 | N |
| ATOM | 380 | CA | LEU | A | 64 | −4.388 | 2.888 | 0.092 | 1.00 | 0.00 | C |
| ATOM | 381 | C | LEU | A | 64 | −4.468 | 1.750 | 1.112 | 1.00 | 0.00 | C |
| ATOM | 382 | O | LEU | A | 64 | −5.344 | 1.747 | 1.976 | 1.00 | 0.00 | O |
| ATOM | 383 | CB | LEU | A | 64 | −3.932 | 4.220 | 0.693 | 1.00 | 0.00 | C |
| ATOM | 384 | CG | LEU | A | 64 | −4.934 | 4.919 | 1.612 | 1.00 | 0.00 | C |
| ATOM | 385 | CD1 | LEU | A | 64 | −4.868 | 4.349 | 3.030 | 1.00 | 0.00 | C |
| ATOM | 386 | CD2 | LEU | A | 64 | −4.731 | 6.436 | 1.595 | 1.00 | 0.00 | C |
| ATOM | 387 | N | ASP | A | 65 | −3.543 | 0.811 | 0.976 | 1.00 | 0.00 | N |
| ATOM | 388 | CA | ASP | A | 65 | −3.498 | −0.330 | 1.874 | 1.00 | 0.00 | C |
| ATOM | 389 | C | ASP | A | 65 | −2.503 | −0.048 | 3.002 | 1.00 | 0.00 | C |
| ATOM | 390 | O | ASP | A | 65 | −2.156 | 1.105 | 3.254 | 1.00 | 0.00 | O |
| ATOM | 391 | CB | ASP | A | 65 | −3.037 | −1.590 | 1.141 | 1.00 | 0.00 | C |
| ATOM | 392 | CG | ASP | A | 65 | −3.898 | −2.832 | 1.384 | 1.00 | 0.00 | C |
| ATOM | 393 | OD1 | ASP | A | 65 | −4.182 | −3.103 | 2.570 | 1.00 | 0.00 | O |
| ATOM | 394 | OD2 | ASP | A | 65 | −4.254 | −3.481 | 0.376 | 1.00 | 0.00 | O |
| ATOM | 395 | N | GLN | A | 66 | −2.072 | −1.121 | 3.649 | 1.00 | 0.00 | N |
| ATOM | 396 | CA | GLN | A | 66 | −1.123 | −1.002 | 4.743 | 1.00 | 0.00 | C |
| ATOM | 397 | C | GLN | A | 66 | −0.081 | 0.073 | 4.430 | 1.00 | 0.00 | C |
| ATOM | 398 | O | GLN | A | 66 | 0.442 | 0.719 | 5.336 | 1.00 | 0.00 | O |
| ATOM | 399 | CB | GLN | A | 66 | −0.454 | −2.346 | 5.036 | 1.00 | 0.00 | C |
| ATOM | 400 | CG | GLN | A | 66 | −1.386 | −3.263 | 5.830 | 1.00 | 0.00 | C |
| ATOM | 401 | CD | GLN | A | 66 | −2.275 | −4.085 | 4.894 | 1.00 | 0.00 | C |
| ATOM | 402 | NE2 | GLN | A | 66 | −3.555 | −4.117 | 5.253 | 1.00 | 0.00 | N |
| ATOM | 403 | OE1 | GLN | A | 66 | −1.828 | −4.652 | 3.911 | 1.00 | 0.00 | O |
| ATOM | 404 | N | ILE | A | 67 | 0.188 | 0.233 | 3.142 | 1.00 | 0.00 | N |

TABLE 3-continued

The atomic coordinates for a representative conformer (without Hydrogens)(SEQ ID NO: 39).

| ATOM | 405 | CA | ILE | A | 67 | 1.158 | 1.218 | 2.697 | 1.00 | 0.00 | C |
|---|---|---|---|---|---|---|---|---|---|---|---|
| ATOM | 406 | C | ILE | A | 67 | 0.450 | 2.553 | 2.459 | 1.00 | 0.00 | C |
| ATOM | 407 | O | ILE | A | 67 | −0.219 | 2.732 | 1.442 | 1.00 | 0.00 | O |
| ATOM | 408 | CB | ILE | A | 67 | 1.925 | 0.703 | 1.478 | 1.00 | 0.00 | C |
| ATOM | 409 | CG1 | ILE | A | 67 | 2.697 | −0.574 | 1.815 | 1.00 | 0.00 | C |
| ATOM | 410 | CG2 | ILE | A | 67 | 2.837 | 1.789 | 0.904 | 1.00 | 0.00 | C |
| ATOM | 411 | CD1 | ILE | A | 67 | 1.854 | −1.818 | 1.527 | 1.00 | 0.00 | C |
| ATOM | 412 | N | GLY | A | 68 | 0.621 | 3.456 | 3.413 | 1.00 | 0.00 | N |
| ATOM | 413 | CA | GLY | A | 68 | 0.005 | 4.769 | 3.320 | 1.00 | 0.00 | C |
| ATOM | 414 | C | GLY | A | 68 | −0.026 | 5.258 | 1.871 | 1.00 | 0.00 | C |
| ATOM | 415 | O | GLY | A | 68 | −1.028 | 5.812 | 1.420 | 1.00 | 0.00 | O |
| ATOM | 416 | N | THR | A | 69 | 1.084 | 5.037 | 1.181 | 1.00 | 0.00 | N |
| ATOM | 417 | CA | THR | A | 69 | 1.197 | 5.448 | −0.208 | 1.00 | 0.00 | C |
| ATOM | 418 | C | THR | A | 69 | −0.054 | 5.041 | −0.988 | 1.00 | 0.00 | C |
| ATOM | 419 | O | THR | A | 69 | −0.280 | 3.856 | −1.232 | 1.00 | 0.00 | O |
| ATOM | 420 | CB | THR | A | 69 | 2.487 | 4.853 | −0.774 | 1.00 | 0.00 | C |
| ATOM | 421 | CG2 | THR | A | 69 | 2.554 | 4.946 | −2.300 | 1.00 | 0.00 | C |
| ATOM | 422 | OG1 | THR | A | 69 | 3.506 | 5.742 | −0.327 | 1.00 | 0.00 | O |
| ATOM | 423 | N | CYS | A | 70 | −0.835 | 6.045 | −1.357 | 1.00 | 0.00 | N |
| ATOM | 424 | CA | CYS | A | 70 | −2.058 | 5.806 | −2.106 | 1.00 | 0.00 | C |
| ATOM | 425 | C | CYS | A | 70 | −1.696 | 5.660 | −3.585 | 1.00 | 0.00 | C |
| ATOM | 426 | O | CYS | A | 70 | −0.804 | 6.347 | −4.079 | 1.00 | 0.00 | O |
| ATOM | 427 | CB | CYS | A | 70 | −3.088 | 6.914 | −1.876 | 1.00 | 0.00 | C |
| ATOM | 428 | SG | CYS | A | 70 | −2.809 | 8.435 | −2.854 | 1.00 | 0.00 | S |
| ATOM | 429 | N | TRP | A | 71 | −2.408 | 4.762 | −4.250 | 1.00 | 0.00 | N |
| ATOM | 430 | CA | TRP | A | 71 | −2.173 | 4.518 | −5.662 | 1.00 | 0.00 | C |
| ATOM | 431 | C | TRP | A | 71 | −3.381 | 5.043 | −6.441 | 1.00 | 0.00 | C |
| ATOM | 432 | O | TRP | A | 71 | −4.519 | 4.911 | −5.991 | 1.00 | 0.00 | O |
| ATOM | 433 | CB | TRP | A | 71 | −1.891 | 3.037 | −5.923 | 1.00 | 0.00 | C |
| ATOM | 434 | CG | TRP | A | 71 | −0.797 | 2.445 | −5.033 | 1.00 | 0.00 | C |
| ATOM | 435 | CD1 | TRP | A | 71 | −0.855 | 2.177 | −3.722 | 1.00 | 0.00 | C |
| ATOM | 436 | CD2 | TRP | A | 71 | 0.531 | 2.057 | −5.446 | 1.00 | 0.00 | C |
| ATOM | 437 | CE2 | TRP | A | 71 | 1.202 | 1.571 | −4.343 | 1.00 | 0.00 | C |
| ATOM | 438 | CE3 | TRP | A | 71 | 1.144 | 2.114 | −6.710 | 1.00 | 0.00 | C |
| ATOM | 439 | NE1 | TRP | A | 71 | 0.333 | 1.645 | −3.261 | 1.00 | 0.00 | N |
| ATOM | 440 | CZ2 | TRP | A | 71 | 2.521 | 1.105 | −4.392 | 1.00 | 0.00 | C |
| ATOM | 441 | CZ3 | TRP | A | 71 | 2.463 | 1.646 | −6.742 | 1.00 | 0.00 | C |
| ATOM | 442 | CH2 | TRP | A | 71 | 3.152 | 1.153 | −5.641 | 1.00 | 0.00 | C |
| ATOM | 443 | N | PRO | A | 72 | −3.085 | 5.642 | −7.624 | 1.00 | 0.00 | N |
| ATOM | 444 | CA | PRO | A | 72 | −4.134 | 6.189 | −8.470 | 1.00 | 0.00 | C |
| ATOM | 445 | C | PRO | A | 72 | −4.897 | 5.072 | −9.185 | 1.00 | 0.00 | C |
| ATOM | 446 | O | PRO | A | 72 | −4.309 | 4.069 | −9.585 | 1.00 | 0.00 | O |
| ATOM | 447 | CB | PRO | A | 72 | −3.420 | 7.128 | −9.426 | 1.00 | 0.00 | C |
| ATOM | 448 | CG | PRO | A | 72 | −1.954 | 6.724 | −9.391 | 1.00 | 0.00 | C |
| ATOM | 449 | CD | PRO | A | 72 | −1.751 | 5.817 | −8.189 | 1.00 | 0.00 | C |
| ATOM | 450 | N | GLN | A | 73 | −6.198 | 5.284 | −9.327 | 1.00 | 0.00 | N |
| ATOM | 451 | CA | GLN | A | 73 | −7.048 | 4.309 | −9.988 | 1.00 | 0.00 | C |
| ATOM | 452 | C | GLN | A | 73 | −6.296 | 3.648 | −11.146 | 1.00 | 0.00 | C |
| ATOM | 453 | O | GLN | A | 73 | −5.414 | 4.258 | −11.746 | 1.00 | 0.00 | O |
| ATOM | 454 | CB | GLN | A | 73 | −8.347 | 4.954 | −10.475 | 1.00 | 0.00 | C |
| ATOM | 455 | CG | GLN | A | 73 | −8.991 | 5.792 | −9.369 | 1.00 | 0.00 | C |
| ATOM | 456 | CD | GLN | A | 73 | −9.009 | 7.275 | −9.743 | 1.00 | 0.00 | C |
| ATOM | 457 | NE2 | GLN | A | 73 | −7.908 | 7.688 | −10.367 | 1.00 | 0.00 | N |
| ATOM | 458 | OE1 | GLN | A | 73 | −9.958 | 7.996 | −9.484 | 1.00 | 0.00 | O |
| ATOM | 459 | N | SER | A | 74 | −6.674 | 2.409 | −11.423 | 1.00 | 0.00 | N |
| ATOM | 460 | CA | SER | A | 74 | −6.047 | 1.658 | −12.499 | 1.00 | 0.00 | C |
| ATOM | 461 | C | SER | A | 74 | −7.090 | 0.795 | −13.212 | 1.00 | 0.00 | C |
| ATOM | 462 | O | SER | A | 74 | −8.286 | 0.921 | −12.954 | 1.00 | 0.00 | O |
| ATOM | 463 | CB | SER | A | 74 | −4.908 | 0.786 | −11.969 | 1.00 | 0.00 | C |
| ATOM | 464 | OG | SER | A | 74 | −4.122 | 1.466 | −10.994 | 1.00 | 0.00 | O |
| ATOM | 465 | N | ALA | A | 75 | −6.599 | −0.062 | −14.094 | 1.00 | 0.00 | N |
| ATOM | 466 | CA | ALA | A | 75 | −7.472 | −0.946 | −14.846 | 1.00 | 0.00 | C |
| ATOM | 467 | C | ALA | A | 75 | −7.455 | −2.337 | −14.210 | 1.00 | 0.00 | C |
| ATOM | 468 | O | ALA | A | 75 | −6.477 | −2.717 | −13.568 | 1.00 | 0.00 | O |
| ATOM | 469 | CB | ALA | A | 75 | −7.036 | −0.970 | −16.312 | 1.00 | 0.00 | C |
| ATOM | 470 | N | PRO | A | 76 | −8.577 | −3.077 | −14.415 | 1.00 | 0.00 | N |
| ATOM | 471 | CA | PRO | A | 76 | −8.699 | −4.418 | −13.868 | 1.00 | 0.00 | C |
| ATOM | 472 | C | PRO | A | 76 | −7.855 | −5.414 | −14.666 | 1.00 | 0.00 | C |
| ATOM | 473 | O | PRO | A | 76 | −7.684 | −5.262 | −15.874 | 1.00 | 0.00 | O |
| ATOM | 474 | CB | PRO | A | 76 | −10.186 | −4.728 | −13.916 | 1.00 | 0.00 | C |
| ATOM | 475 | CG | PRO | A | 76 | −10.785 | −3.745 | −14.910 | 1.00 | 0.00 | C |
| ATOM | 476 | CD | PRO | A | 76 | −9.754 | −2.659 | −15.170 | 1.00 | 0.00 | C |
| ATOM | 477 | N | GLY | A | 77 | −7.348 | −6.411 | −13.955 | 1.00 | 0.00 | N |
| ATOM | 478 | CA | GLY | A | 77 | −6.525 | −7.432 | −14.581 | 1.00 | 0.00 | C |
| ATOM | 479 | C | GLY | A | 77 | −5.136 | −6.886 | −14.919 | 1.00 | 0.00 | C |
| ATOM | 480 | O | GLY | A | 77 | −4.334 | −7.571 | −15.551 | 1.00 | 0.00 | O |
| ATOM | 481 | N | ALA | A | 78 | −4.896 | −5.658 | −14.484 | 1.00 | 0.00 | N |

TABLE 3-continued

The atomic coordinates for a representative conformer (without Hydrogens)(SEQ ID NO: 39).

| ATOM | 482 | CA | ALA | A | 78 | -3.619 | -5.012 | -14.733 | 1.00 | 0.00 | C |
|------|-----|-----|-----|---|----|--------|--------|---------|------|------|---|
| ATOM | 483 | C | ALA | A | 78 | -2.701 | -5.226 | -13.528 | 1.00 | 0.00 | C |
| ATOM | 484 | O | ALA | A | 78 | -2.894 | -6.162 | -12.754 | 1.00 | 0.00 | O |
| ATOM | 485 | CB | ALA | A | 78 | -3.846 | -3.530 | -15.037 | 1.00 | 0.00 | C |
| ATOM | 486 | N | LEU | A | 79 | -1.721 | -4.342 | -13.406 | 1.00 | 0.00 | N |
| ATOM | 487 | CA | LEU | A | 79 | -0.773 | -4.422 | -12.308 | 1.00 | 0.00 | C |
| ATOM | 488 | C | LEU | A | 79 | 0.157 | -3.208 | -12.354 | 1.00 | 0.00 | C |
| ATOM | 489 | O | LEU | A | 79 | 0.683 | -2.864 | -13.411 | 1.00 | 0.00 | O |
| ATOM | 490 | CB | LEU | A | 79 | -0.036 | -5.763 | -12.334 | 1.00 | 0.00 | C |
| ATOM | 491 | CG | LEU | A | 79 | 0.413 | -6.254 | -13.711 | 1.00 | 0.00 | C |
| ATOM | 492 | CD1 | LEU | A | 79 | 1.884 | -5.914 | -13.962 | 1.00 | 0.00 | C |
| ATOM | 493 | CD2 | LEU | A | 79 | 0.134 | -7.750 | -13.877 | 1.00 | 0.00 | C |
| ATOM | 494 | N | VAL | A | 80 | 0.331 | -2.592 | -11.193 | 1.00 | 0.00 | N |
| ATOM | 495 | CA | VAL | A | 80 | 1.189 | -1.424 | -11.088 | 1.00 | 0.00 | C |
| ATOM | 496 | C | VAL | A | 80 | 2.517 | -1.828 | -10.445 | 1.00 | 0.00 | C |
| ATOM | 497 | O | VAL | A | 80 | 2.883 | -1.311 | -9.390 | 1.00 | 0.00 | O |
| ATOM | 498 | CB | VAL | A | 80 | 0.467 | -0.313 | -10.321 | 1.00 | 0.00 | C |
| ATOM | 499 | CG1 | VAL | A | 80 | 1.443 | 0.789 | -9.905 | 1.00 | 0.00 | C |
| ATOM | 500 | CG2 | VAL | A | 80 | -0.688 | 0.259 | -11.145 | 1.00 | 0.00 | C |
| ATOM | 501 | N | GLU | A | 81 | 3.203 | -2.749 | -11.108 | 1.00 | 0.00 | N |
| ATOM | 502 | CA | GLU | A | 81 | 4.482 | -3.228 | -10.614 | 1.00 | 0.00 | C |
| ATOM | 503 | C | GLU | A | 81 | 5.620 | -2.366 | -11.164 | 1.00 | 0.00 | C |
| ATOM | 504 | O | GLU | A | 81 | 5.569 | -1.922 | -12.310 | 1.00 | 0.00 | O |
| ATOM | 505 | CB | GLU | A | 81 | 4.689 | -4.702 | -10.969 | 1.00 | 0.00 | C |
| ATOM | 506 | CG | GLU | A | 81 | 4.966 | -4.872 | -12.464 | 1.00 | 0.00 | C |
| ATOM | 507 | CD | GLU | A | 81 | 6.412 | -5.310 | -12.708 | 1.00 | 0.00 | C |
| ATOM | 508 | OE1 | GLU | A | 81 | 7.052 | -4.691 | -13.586 | 1.00 | 0.00 | O |
| ATOM | 509 | OE2 | GLU | A | 81 | 6.844 | -6.254 | -12.012 | 1.00 | 0.00 | O |
| ATOM | 510 | N | ARG | A | 82 | 6.620 | -2.154 | -10.321 | 1.00 | 0.00 | N |
| ATOM | 511 | CA | ARG | A | 82 | 7.769 | -1.354 | -10.709 | 1.00 | 0.00 | C |
| ATOM | 512 | C | ARG | A | 82 | 9.013 | -1.800 | -9.937 | 1.00 | 0.00 | C |
| ATOM | 513 | O | ARG | A | 82 | 9.572 | -1.032 | -9.156 | 1.00 | 0.00 | O |
| ATOM | 514 | CB | ARG | A | 82 | 7.518 | 0.132 | -10.443 | 1.00 | 0.00 | C |
| ATOM | 515 | CG | ARG | A | 82 | 6.221 | 0.597 | -11.107 | 1.00 | 0.00 | C |
| ATOM | 516 | CD | ARG | A | 82 | 6.147 | 2.124 | -11.157 | 1.00 | 0.00 | C |
| ATOM | 517 | NE | ARG | A | 82 | 5.340 | 2.631 | -10.024 | 1.00 | 0.00 | N |
| ATOM | 518 | CZ | ARG | A | 82 | 5.374 | 3.895 | -9.584 | 1.00 | 0.00 | C |
| ATOM | 519 | NH1 | ARG | A | 82 | 6.174 | 4.791 | -10.178 | 1.00 | 0.00 | N |
| ATOM | 520 | NH2 | ARG | A | 82 | 4.608 | 4.264 | -8.548 | 1.00 | 0.00 | N |
| ATOM | 521 | N | PRO | A | 83 | 9.419 | -3.072 | -10.190 | 1.00 | 0.00 | N |
| ATOM | 522 | CA | PRO | A | 83 | 10.587 | -3.630 | -9.528 | 1.00 | 0.00 | C |
| ATOM | 523 | C | PRO | A | 83 | 11.877 | -3.062 | -10.122 | 1.00 | 0.00 | C |
| ATOM | 524 | O | PRO | A | 83 | 12.306 | -3.478 | -11.198 | 1.00 | 0.00 | O |
| ATOM | 525 | CB | PRO | A | 83 | 10.460 | -5.134 | -9.710 | 1.00 | 0.00 | C |
| ATOM | 526 | CG | PRO | A | 83 | 9.483 | -5.335 | -10.858 | 1.00 | 0.00 | C |
| ATOM | 527 | CD | PRO | A | 83 | 8.782 | -4.011 | -11.109 | 1.00 | 0.00 | C |
| ATOM | 528 | N | CYS | A | 84 | 12.461 | -2.121 | -9.396 | 1.00 | 0.00 | N |
| ATOM | 529 | CA | CYS | A | 84 | 13.695 | -1.492 | -9.837 | 1.00 | 0.00 | C |
| ATOM | 530 | C | CYS | A | 84 | 13.401 | -0.706 | -11.116 | 1.00 | 0.00 | C |
| ATOM | 531 | O | CYS | A | 84 | 12.423 | -0.982 | -11.809 | 1.00 | 0.00 | O |
| ATOM | 532 | CB | CYS | A | 84 | 14.811 | -2.518 | -10.042 | 1.00 | 0.00 | C |
| ATOM | 533 | SG | CYS | A | 84 | 14.854 | -3.864 | -8.802 | 1.00 | 0.00 | S |
| ATOM | 534 | N | PRO | A | 85 | 14.289 | 0.286 | -11.398 | 1.00 | 0.00 | N |
| ATOM | 535 | CA | PRO | A | 85 | 14.136 | 1.114 | -12.581 | 1.00 | 0.00 | C |
| ATOM | 536 | C | PRO | A | 85 | 14.537 | 0.348 | -13.843 | 1.00 | 0.00 | C |
| ATOM | 537 | O | PRO | A | 85 | 13.725 | 0.167 | -14.749 | 1.00 | 0.00 | O |
| ATOM | 538 | CB | PRO | A | 85 | 15.006 | 2.333 | -12.324 | 1.00 | 0.00 | C |
| ATOM | 539 | CG | PRO | A | 85 | 15.972 | 1.930 | -11.222 | 1.00 | 0.00 | C |
| ATOM | 540 | CD | PRO | A | 85 | 15.459 | 0.641 | -10.599 | 1.00 | 0.00 | C |
| ATOM | 541 | N | GLU | A | 86 | 15.791 | -0.081 | -13.861 | 1.00 | 0.00 | N |
| ATOM | 542 | CA | GLU | A | 86 | 16.310 | -0.824 | -14.997 | 1.00 | 0.00 | C |
| ATOM | 543 | C | GLU | A | 86 | 17.100 | -2.043 | -14.517 | 1.00 | 0.00 | C |
| ATOM | 544 | O | GLU | A | 86 | 17.792 | -1.980 | -13.503 | 1.00 | 0.00 | O |
| ATOM | 545 | CB | GLU | A | 86 | 17.172 | 0.071 | -15.889 | 1.00 | 0.00 | C |
| ATOM | 546 | CG | GLU | A | 86 | 16.830 | -0.134 | -17.367 | 1.00 | 0.00 | C |
| ATOM | 547 | CD | GLU | A | 86 | 18.099 | -0.270 | -18.210 | 1.00 | 0.00 | C |
| ATOM | 548 | OE1 | GLU | A | 86 | 19.016 | 0.549 | -17.990 | 1.00 | 0.00 | O |
| ATOM | 549 | OE2 | GLU | A | 86 | 18.122 | -1.190 | -19.056 | 1.00 | 0.00 | O |
| ATOM | 550 | N | TYR | A | 87 | 16.971 | -3.126 | -15.271 | 1.00 | 0.00 | N |
| ATOM | 551 | CA | TYR | A | 87 | 17.664 | -4.358 | -14.936 | 1.00 | 0.00 | C |
| ATOM | 552 | C | TYR | A | 87 | 19.134 | -4.292 | -15.356 | 1.00 | 0.00 | C |
| ATOM | 553 | O | TYR | A | 87 | 19.591 | -5.105 | -16.158 | 1.00 | 0.00 | O |
| ATOM | 554 | CB | TYR | A | 87 | 16.968 | -5.464 | -15.732 | 1.00 | 0.00 | C |
| ATOM | 555 | CG | TYR | A | 87 | 16.981 | -6.830 | -15.042 | 1.00 | 0.00 | C |
| ATOM | 556 | CD1 | TYR | A | 87 | 15.834 | -7.314 | -14.448 | 1.00 | 0.00 | C |
| ATOM | 557 | CD2 | TYR | A | 87 | 18.141 | -7.577 | -15.014 | 1.00 | 0.00 | C |
| ATOM | 558 | CE1 | TYR | A | 87 | 15.845 | -8.599 | -13.800 | 1.00 | 0.00 | C |

TABLE 3-continued

The atomic coordinates for a representative conformer (without Hydrogens)(SEQ ID NO: 39).

| ATOM | 559 | CE2 | TYR | A | 87 | 18.153 | −8.863 | −14.365 | 1.00 | 0.00 | C |
|---|---|---|---|---|---|---|---|---|---|---|---|
| ATOM | 560 | CZ | TYR | A | 87 | 17.005 | −9.310 | −13.790 | 1.00 | 0.00 | C |
| ATOM | 561 | OH | TYR | A | 87 | 17.016 | −10.524 | −13.177 | 1.00 | 0.00 | O |
| ATOM | 562 | N | PHE | A | 88 | 19.833 | −3.316 | −14.795 | 1.00 | 0.00 | N |
| ATOM | 563 | CA | PHE | A | 88 | 21.242 | −3.133 | −15.101 | 1.00 | 0.00 | C |
| ATOM | 564 | C | PHE | A | 88 | 22.101 | −4.166 | −14.367 | 1.00 | 0.00 | C |
| ATOM | 565 | O | PHE | A | 88 | 23.000 | −4.762 | −14.958 | 1.00 | 0.00 | O |
| ATOM | 566 | CB | PHE | A | 88 | 21.627 | −1.733 | −14.620 | 1.00 | 0.00 | C |
| ATOM | 567 | CG | PHE | A | 88 | 21.183 | −1.423 | −13.188 | 1.00 | 0.00 | C |
| ATOM | 568 | CD1 | PHE | A | 88 | 21.961 | −1.801 | −12.139 | 1.00 | 0.00 | C |
| ATOM | 569 | CD2 | PHE | A | 88 | 20.011 | −0.771 | −12.965 | 1.00 | 0.00 | C |
| ATOM | 570 | CE1 | PHE | A | 88 | 21.550 | −1.514 | −10.810 | 1.00 | 0.00 | C |
| ATOM | 571 | CE2 | PHE | A | 88 | 19.599 | −0.484 | −11.637 | 1.00 | 0.00 | C |
| ATOM | 572 | CZ | PHE | A | 88 | 20.378 | −0.862 | −10.588 | 1.00 | 0.00 | C |
| ATOM | 573 | N | ASN | A | 89 | 21.793 | −4.344 | −13.092 | 1.00 | 0.00 | N |
| ATOM | 574 | CA | ASN | A | 89 | 22.526 | −5.294 | −12.270 | 1.00 | 0.00 | C |
| ATOM | 575 | C | ASN | A | 89 | 23.968 | −4.812 | −12.104 | 1.00 | 0.00 | C |
| ATOM | 576 | O | ASN | A | 89 | 24.867 | −5.278 | −12.801 | 1.00 | 0.00 | O |
| ATOM | 577 | CB | ASN | A | 89 | 22.563 | −6.676 | −12.928 | 1.00 | 0.00 | C |
| ATOM | 578 | CG | ASN | A | 89 | 21.166 | −7.104 | −13.383 | 1.00 | 0.00 | C |
| ATOM | 579 | ND2 | ASN | A | 89 | 20.214 | −6.891 | −12.479 | 1.00 | 0.00 | N |
| ATOM | 580 | OD1 | ASN | A | 89 | 20.968 | −7.593 | −14.483 | 1.00 | 0.00 | O |
| ATOM | 581 | N | GLY | A | 90 | 24.144 | −3.882 | −11.176 | 1.00 | 0.00 | N |
| ATOM | 582 | CA | GLY | A | 90 | 25.461 | −3.330 | −10.909 | 1.00 | 0.00 | C |
| ATOM | 583 | C | GLY | A | 90 | 25.599 | −1.927 | −11.502 | 1.00 | 0.00 | C |
| ATOM | 584 | O | GLY | A | 90 | 26.486 | −1.679 | −12.318 | 1.00 | 0.00 | O |
| ATOM | 585 | N | ILE | A | 91 | 24.709 | −1.047 | −11.071 | 1.00 | 0.00 | N |
| ATOM | 586 | CA | ILE | A | 91 | 24.719 | 0.326 | −11.549 | 1.00 | 0.00 | C |
| ATOM | 587 | C | ILE | A | 91 | 23.989 | 1.217 | −10.544 | 1.00 | 0.00 | C |
| ATOM | 588 | O | ILE | A | 91 | 23.343 | 0.721 | −9.622 | 1.00 | 0.00 | O |
| ATOM | 589 | CB | ILE | A | 91 | 24.151 | 0.403 | −12.967 | 1.00 | 0.00 | C |
| ATOM | 590 | CG1 | ILE | A | 91 | 25.253 | 0.701 | −13.985 | 1.00 | 0.00 | C |
| ATOM | 591 | CG2 | ILE | A | 91 | 23.008 | 1.418 | −13.045 | 1.00 | 0.00 | C |
| ATOM | 592 | CD1 | ILE | A | 91 | 25.812 | 2.111 | −13.790 | 1.00 | 0.00 | C |
| ATOM | 593 | N | LYS | A | 92 | 24.115 | 2.519 | −10.754 | 1.00 | 0.00 | N |
| ATOM | 594 | CA | LYS | A | 92 | 23.476 | 3.485 | −9.878 | 1.00 | 0.00 | C |
| ATOM | 595 | C | LYS | A | 92 | 22.023 | 3.681 | −10.317 | 1.00 | 0.00 | C |
| ATOM | 596 | O | LYS | A | 92 | 21.761 | 4.276 | −11.361 | 1.00 | 0.00 | O |
| ATOM | 597 | CB | LYS | A | 92 | 24.284 | 4.783 | −9.830 | 1.00 | 0.00 | C |
| ATOM | 598 | CG | LYS | A | 92 | 24.464 | 5.264 | −8.389 | 1.00 | 0.00 | C |
| ATOM | 599 | CD | LYS | A | 92 | 25.098 | 6.656 | −8.350 | 1.00 | 0.00 | C |
| ATOM | 600 | CE | LYS | A | 92 | 25.921 | 6.848 | −7.074 | 1.00 | 0.00 | C |
| ATOM | 601 | NZ | LYS | A | 92 | 25.140 | 7.594 | −6.062 | 1.00 | 0.00 | N |
| ATOM | 602 | N | TYR | A | 93 | 21.116 | 3.169 | −9.497 | 1.00 | 0.00 | N |
| ATOM | 603 | CA | TYR | A | 93 | 19.697 | 3.281 | −9.788 | 1.00 | 0.00 | C |
| ATOM | 604 | C | TYR | A | 93 | 19.162 | 4.657 | −9.387 | 1.00 | 0.00 | C |
| ATOM | 605 | O | TYR | A | 93 | 19.872 | 5.447 | −8.768 | 1.00 | 0.00 | O |
| ATOM | 606 | CB | TYR | A | 93 | 19.007 | 2.212 | −8.938 | 1.00 | 0.00 | C |
| ATOM | 607 | CG | TYR | A | 93 | 19.359 | 2.277 | −7.450 | 1.00 | 0.00 | C |
| ATOM | 608 | CD1 | TYR | A | 93 | 18.953 | 3.357 | −6.691 | 1.00 | 0.00 | C |
| ATOM | 609 | CD2 | TYR | A | 93 | 20.082 | 1.258 | −6.866 | 1.00 | 0.00 | C |
| ATOM | 610 | CE1 | TYR | A | 93 | 19.283 | 3.419 | −5.292 | 1.00 | 0.00 | C |
| ATOM | 611 | CE2 | TYR | A | 93 | 20.414 | 1.320 | −5.466 | 1.00 | 0.00 | C |
| ATOM | 612 | CZ | TYR | A | 93 | 19.998 | 2.397 | −4.748 | 1.00 | 0.00 | C |
| ATOM | 613 | OH | TYR | A | 93 | 20.311 | 2.456 | −3.426 | 1.00 | 0.00 | O |
| ATOM | 614 | N | ASN | A | 94 | 17.914 | 4.902 | −9.759 | 1.00 | 0.00 | N |
| ATOM | 615 | CA | ASN | A | 94 | 17.275 | 6.170 | −9.447 | 1.00 | 0.00 | C |
| ATOM | 616 | C | ASN | A | 94 | 16.209 | 5.947 | −8.373 | 1.00 | 0.00 | C |
| ATOM | 617 | O | ASN | A | 94 | 15.914 | 6.849 | −7.589 | 1.00 | 0.00 | O |
| ATOM | 618 | CB | ASN | A | 94 | 16.588 | 6.758 | −10.681 | 1.00 | 0.00 | C |
| ATOM | 619 | CG | ASN | A | 94 | 17.616 | 7.184 | −11.731 | 1.00 | 0.00 | C |
| ATOM | 620 | ND2 | ASN | A | 94 | 18.485 | 6.231 | −12.054 | 1.00 | 0.00 | N |
| ATOM | 621 | OD1 | ASN | A | 94 | 17.619 | 8.303 | −12.215 | 1.00 | 0.00 | O |
| ATOM | 622 | N | THR | A | 95 | 15.660 | 4.741 | −8.369 | 1.00 | 0.00 | N |
| ATOM | 623 | CA | THR | A | 95 | 14.633 | 4.390 | −7.403 | 1.00 | 0.00 | C |
| ATOM | 624 | C | THR | A | 95 | 13.391 | 5.260 | −7.604 | 1.00 | 0.00 | C |
| ATOM | 625 | O | THR | A | 95 | 13.411 | 6.454 | −7.309 | 1.00 | 0.00 | O |
| ATOM | 626 | CB | THR | A | 95 | 15.239 | 4.510 | −6.003 | 1.00 | 0.00 | C |
| ATOM | 627 | CG2 | THR | A | 95 | 14.191 | 4.371 | −4.898 | 1.00 | 0.00 | C |
| ATOM | 628 | OG1 | THR | A | 95 | 16.040 | 3.339 | −5.871 | 1.00 | 0.00 | O |
| ATOM | 629 | N | THR | A | 96 | 12.339 | 4.628 | −8.106 | 1.00 | 0.00 | N |
| ATOM | 630 | CA | THR | A | 96 | 11.090 | 5.331 | −8.350 | 1.00 | 0.00 | C |
| ATOM | 631 | C | THR | A | 96 | 9.948 | 4.671 | −7.577 | 1.00 | 0.00 | C |
| ATOM | 632 | O | THR | A | 96 | 8.925 | 4.312 | −8.159 | 1.00 | 0.00 | O |
| ATOM | 633 | CB | THR | A | 96 | 10.858 | 5.371 | −9.862 | 1.00 | 0.00 | C |
| ATOM | 634 | CG2 | THR | A | 96 | 12.082 | 5.873 | −10.630 | 1.00 | 0.00 | C |
| ATOM | 635 | OG1 | THR | A | 96 | 10.756 | 3.998 | −10.234 | 1.00 | 0.00 | O |

TABLE 3-continued

The atomic coordinates for a representative conformer (without Hydrogens)(SEQ ID NO: 39).

| ATOM | 636 | N | ARG | A | 97 | 10.160 | 4.530 | −6.277 | 1.00 | 0.00 | N |
|---|---|---|---|---|---|---|---|---|---|---|---|
| ATOM | 637 | CA | ARG | A | 97 | 9.159 | 3.919 | −5.417 | 1.00 | 0.00 | C |
| ATOM | 638 | C | ARG | A | 97 | 8.787 | 2.530 | −5.940 | 1.00 | 0.00 | C |
| ATOM | 639 | O | ARG | A | 97 | 7.657 | 2.307 | −6.370 | 1.00 | 0.00 | O |
| ATOM | 640 | CB | ARG | A | 97 | 7.899 | 4.782 | −5.340 | 1.00 | 0.00 | C |
| ATOM | 641 | CG | ARG | A | 97 | 7.976 | 5.763 | −4.169 | 1.00 | 0.00 | C |
| ATOM | 642 | CD | ARG | A | 97 | 8.032 | 5.020 | −2.833 | 1.00 | 0.00 | C |
| ATOM | 643 | NE | ARG | A | 97 | 9.302 | 5.324 | −2.138 | 1.00 | 0.00 | N |
| ATOM | 644 | CZ | ARG | A | 97 | 9.631 | 6.535 | −1.668 | 1.00 | 0.00 | C |
| ATOM | 645 | NH1 | ARG | A | 97 | 8.785 | 7.563 | −1.817 | 1.00 | 0.00 | N |
| ATOM | 646 | NH2 | ARG | A | 97 | 10.806 | 6.718 | −1.050 | 1.00 | 0.00 | N |
| ATOM | 647 | N | ASN | A | 98 | 9.760 | 1.632 | −5.885 | 1.00 | 0.00 | N |
| ATOM | 648 | CA | ASN | A | 98 | 9.550 | 0.271 | −6.348 | 1.00 | 0.00 | C |
| ATOM | 649 | C | ASN | A | 98 | 8.379 | −0.347 | −5.582 | 1.00 | 0.00 | C |
| ATOM | 650 | O | ASN | A | 98 | 8.063 | 0.080 | −4.472 | 1.00 | 0.00 | O |
| ATOM | 651 | CB | ASN | A | 98 | 10.787 | −0.593 | −6.097 | 1.00 | 0.00 | C |
| ATOM | 652 | CG | ASN | A | 98 | 11.303 | −0.412 | −4.668 | 1.00 | 0.00 | C |
| ATOM | 653 | ND2 | ASN | A | 98 | 12.502 | −0.946 | −4.454 | 1.00 | 0.00 | N |
| ATOM | 654 | OD1 | ASN | A | 98 | 10.655 | 0.174 | −3.817 | 1.00 | 0.00 | O |
| ATOM | 655 | N | ALA | A | 99 | 7.765 | −1.342 | −6.205 | 1.00 | 0.00 | N |
| ATOM | 656 | CA | ALA | A | 99 | 6.635 | −2.024 | −5.595 | 1.00 | 0.00 | C |
| ATOM | 657 | C | ALA | A | 99 | 6.027 | −2.997 | −6.607 | 1.00 | 0.00 | C |
| ATOM | 658 | O | ALA | A | 99 | 6.405 | −2.999 | −7.777 | 1.00 | 0.00 | O |
| ATOM | 659 | CB | ALA | A | 99 | 5.622 | −0.990 | −5.100 | 1.00 | 0.00 | C |
| ATOM | 660 | N | TYR | A | 100 | 5.095 | −3.803 | −6.118 | 1.00 | 0.00 | N |
| ATOM | 661 | CA | TYR | A | 100 | 4.431 | −4.779 | −6.965 | 1.00 | 0.00 | C |
| ATOM | 662 | C | TYR | A | 100 | 2.993 | −5.018 | −6.502 | 1.00 | 0.00 | C |
| ATOM | 663 | O | TYR | A | 100 | 2.761 | −5.727 | −5.523 | 1.00 | 0.00 | O |
| ATOM | 664 | CB | TYR | A | 100 | 5.226 | −6.078 | −6.814 | 1.00 | 0.00 | C |
| ATOM | 665 | CG | TYR | A | 100 | 4.636 | −7.260 | −7.586 | 1.00 | 0.00 | C |
| ATOM | 666 | CD1 | TYR | A | 100 | 3.710 | −8.086 | −6.982 | 1.00 | 0.00 | C |
| ATOM | 667 | CD2 | TYR | A | 100 | 5.032 | −7.502 | −8.885 | 1.00 | 0.00 | C |
| ATOM | 668 | CE1 | TYR | A | 100 | 3.156 | −9.199 | −7.707 | 1.00 | 0.00 | C |
| ATOM | 669 | CE2 | TYR | A | 100 | 4.479 | −8.615 | −9.612 | 1.00 | 0.00 | C |
| ATOM | 670 | CZ | TYR | A | 100 | 3.567 | −9.409 | −8.987 | 1.00 | 0.00 | C |
| ATOM | 671 | OH | TYR | A | 100 | 3.044 | −10.460 | −9.673 | 1.00 | 0.00 | O |
| ATOM | 672 | N | ARG | A | 101 | 2.063 | −4.413 | −7.227 | 1.00 | 0.00 | N |
| ATOM | 673 | CA | ARG | A | 101 | 0.654 | −4.552 | −6.902 | 1.00 | 0.00 | C |
| ATOM | 674 | C | ARG | A | 101 | −0.152 | −4.882 | −8.161 | 1.00 | 0.00 | C |
| ATOM | 675 | O | ARG | A | 101 | −0.078 | −4.162 | −9.156 | 1.00 | 0.00 | O |
| ATOM | 676 | CB | ARG | A | 101 | 0.104 | −3.268 | −6.276 | 1.00 | 0.00 | C |
| ATOM | 677 | CG | ARG | A | 101 | 0.026 | −3.392 | −4.753 | 1.00 | 0.00 | C |
| ATOM | 678 | CD | ARG | A | 101 | −1.428 | −3.497 | −4.285 | 1.00 | 0.00 | C |
| ATOM | 679 | NE | ARG | A | 101 | −1.699 | −2.482 | −3.242 | 1.00 | 0.00 | N |
| ATOM | 680 | CZ | ARG | A | 101 | −2.009 | −1.205 | −3.500 | 1.00 | 0.00 | C |
| ATOM | 681 | NH1 | ARG | A | 101 | −2.090 | −0.777 | −4.767 | 1.00 | 0.00 | N |
| ATOM | 682 | NH2 | ARG | A | 101 | −2.239 | −0.354 | −2.491 | 1.00 | 0.00 | N |
| ATOM | 683 | N | GLU | A | 102 | −0.901 | −5.970 | −8.077 | 1.00 | 0.00 | N |
| ATOM | 684 | CA | GLU | A | 102 | −1.718 | −6.404 | −9.197 | 1.00 | 0.00 | C |
| ATOM | 685 | C | GLU | A | 102 | −3.177 | −5.998 | −8.979 | 1.00 | 0.00 | C |
| ATOM | 686 | O | GLU | A | 102 | −3.617 | −5.835 | −7.842 | 1.00 | 0.00 | O |
| ATOM | 687 | CB | GLU | A | 102 | −1.597 | −7.915 | −9.412 | 1.00 | 0.00 | C |
| ATOM | 688 | CG | GLU | A | 102 | −2.018 | −8.682 | −8.157 | 1.00 | 0.00 | C |
| ATOM | 689 | CD | GLU | A | 102 | −2.814 | −9.937 | −8.522 | 1.00 | 0.00 | C |
| ATOM | 690 | OE1 | GLU | A | 102 | −3.952 | −10.053 | −8.019 | 1.00 | 0.00 | O |
| ATOM | 691 | OE2 | GLU | A | 102 | −2.267 | −10.750 | −9.298 | 1.00 | 0.00 | O |
| ATOM | 692 | N | CYS | A | 103 | −3.888 | −5.844 | −10.087 | 1.00 | 0.00 | N |
| ATOM | 693 | CA | CYS | A | 103 | −5.287 | −5.458 | −10.031 | 1.00 | 0.00 | C |
| ATOM | 694 | C | CYS | A | 103 | −6.121 | −6.589 | −10.637 | 1.00 | 0.00 | C |
| ATOM | 695 | O | CYS | A | 103 | −5.982 | −6.903 | −11.818 | 1.00 | 0.00 | O |
| ATOM | 696 | CB | CYS | A | 103 | −5.535 | −4.124 | −10.738 | 1.00 | 0.00 | C |
| ATOM | 697 | SG | CYS | A | 103 | −6.047 | −2.756 | −9.636 | 1.00 | 0.00 | S |
| ATOM | 698 | N | LEU | A | 104 | −6.969 | −7.170 | −9.801 | 1.00 | 0.00 | N |
| ATOM | 699 | CA | LEU | A | 104 | −7.825 | −8.259 | −10.239 | 1.00 | 0.00 | C |
| ATOM | 700 | C | LEU | A | 104 | −8.706 | −7.775 | −11.393 | 1.00 | 0.00 | C |
| ATOM | 701 | O | LEU | A | 104 | −8.822 | −6.574 | −11.629 | 1.00 | 0.00 | O |
| ATOM | 702 | CB | LEU | A | 104 | −8.614 | −8.828 | −9.059 | 1.00 | 0.00 | C |
| ATOM | 703 | CG | LEU | A | 104 | −7.955 | −9.984 | −8.305 | 1.00 | 0.00 | C |
| ATOM | 704 | CD1 | LEU | A | 104 | −8.606 | −10.189 | −6.936 | 1.00 | 0.00 | C |
| ATOM | 705 | CD2 | LEU | A | 104 | −7.968 | −11.264 | −9.144 | 1.00 | 0.00 | C |
| ATOM | 706 | N | GLU | A | 105 | −9.304 | −8.737 | −12.081 | 1.00 | 0.00 | N |
| ATOM | 707 | CA | GLU | A | 105 | −10.171 | −8.425 | −13.205 | 1.00 | 0.00 | C |
| ATOM | 708 | C | GLU | A | 105 | −11.537 | −7.951 | −12.705 | 1.00 | 0.00 | C |
| ATOM | 709 | O | GLU | A | 105 | −12.426 | −7.659 | −13.504 | 1.00 | 0.00 | O |
| ATOM | 710 | CB | GLU | A | 105 | −10.316 | −9.630 | −14.137 | 1.00 | 0.00 | C |
| ATOM | 711 | CG | GLU | A | 105 | −10.676 | −9.186 | −15.556 | 1.00 | 0.00 | C |
| ATOM | 712 | CD | GLU | A | 105 | −11.024 | −10.388 | −16.435 | 1.00 | 0.00 | C |

TABLE 3-continued

The atomic coordinates for a representative conformer (without Hydrogens)(SEQ ID NO: 39).

| ATOM | 713 | OE1 | GLU | A | 105 | −10.323 | −10.567 | −17.455 | 1.00 | 0.00 | O |
|---|---|---|---|---|---|---|---|---|---|---|---|
| ATOM | 714 | OE2 | GLU | A | 105 | −11.982 | −11.102 | −16.068 | 1.00 | 0.00 | O |
| ATOM | 715 | N | ASN | A | 106 | −11.660 | −7.887 | −11.388 | 1.00 | 0.00 | N |
| ATOM | 716 | CA | ASN | A | 106 | −12.903 | −7.452 | −10.773 | 1.00 | 0.00 | C |
| ATOM | 717 | C | ASN | A | 106 | −12.795 | −5.970 | −10.407 | 1.00 | 0.00 | C |
| ATOM | 718 | O | ASN | A | 106 | −13.755 | −5.377 | −9.918 | 1.00 | 0.00 | O |
| ATOM | 719 | CB | ASN | A | 106 | −13.186 | −8.236 | −9.490 | 1.00 | 0.00 | C |
| ATOM | 720 | CG | ASN | A | 106 | −14.634 | −8.728 | −9.455 | 1.00 | 0.00 | C |
| ATOM | 721 | ND2 | ASN | A | 106 | −14.766 | −10.038 | −9.647 | 1.00 | 0.00 | N |
| ATOM | 722 | OD1 | ASN | A | 106 | −15.571 | −7.968 | −9.267 | 1.00 | 0.00 | O |
| ATOM | 723 | N | GLY | A | 107 | −11.618 | −5.415 | −10.659 | 1.00 | 0.00 | N |
| ATOM | 724 | CA | GLY | A | 107 | −11.373 | −4.015 | −10.362 | 1.00 | 0.00 | C |
| ATOM | 725 | C | GLY | A | 107 | −10.995 | −3.823 | −8.892 | 1.00 | 0.00 | C |
| ATOM | 726 | O | GLY | A | 107 | −11.566 | −2.976 | −8.207 | 1.00 | 0.00 | O |
| ATOM | 727 | N | THR | A | 108 | −10.036 | −4.624 | −8.452 | 1.00 | 0.00 | N |
| ATOM | 728 | CA | THR | A | 108 | −9.575 | −4.553 | −7.075 | 1.00 | 0.00 | C |
| ATOM | 729 | C | THR | A | 108 | −8.055 | −4.721 | −7.013 | 1.00 | 0.00 | C |
| ATOM | 730 | O | THR | A | 108 | −7.454 | −5.302 | −7.914 | 1.00 | 0.00 | O |
| ATOM | 731 | CB | THR | A | 108 | −10.337 | −5.606 | −6.268 | 1.00 | 0.00 | C |
| ATOM | 732 | CG2 | THR | A | 108 | −11.854 | −5.455 | −6.392 | 1.00 | 0.00 | C |
| ATOM | 733 | OG1 | THR | A | 108 | −10.053 | −6.831 | −6.939 | 1.00 | 0.00 | O |
| ATOM | 734 | N | TRP | A | 109 | −7.480 | −4.200 | −5.939 | 1.00 | 0.00 | N |
| ATOM | 735 | CA | TRP | A | 109 | −6.041 | −4.285 | −5.747 | 1.00 | 0.00 | C |
| ATOM | 736 | C | TRP | A | 109 | −5.725 | −5.656 | −5.144 | 1.00 | 0.00 | C |
| ATOM | 737 | O | TRP | A | 109 | −6.600 | −6.515 | −5.053 | 1.00 | 0.00 | O |
| ATOM | 738 | CB | TRP | A | 109 | −5.533 | −3.123 | −4.890 | 1.00 | 0.00 | C |
| ATOM | 739 | CG | TRP | A | 109 | −5.450 | −1.791 | −5.636 | 1.00 | 0.00 | C |
| ATOM | 740 | CD1 | TRP | A | 109 | −6.184 | −0.687 | −5.437 | 1.00 | 0.00 | C |
| ATOM | 741 | CD2 | TRP | A | 109 | −4.548 | −1.464 | −6.713 | 1.00 | 0.00 | C |
| ATOM | 742 | CE2 | TRP | A | 109 | −4.795 | −0.165 | −7.106 | 1.00 | 0.00 | C |
| ATOM | 743 | CE3 | TRP | A | 109 | −3.554 | −2.241 | −7.336 | 1.00 | 0.00 | C |
| ATOM | 744 | NE1 | TRP | A | 109 | −5.822 | 0.323 | −6.306 | 1.00 | 0.00 | N |
| ATOM | 745 | CZ2 | TRP | A | 109 | −4.092 | 0.473 | −8.135 | 1.00 | 0.00 | C |
| ATOM | 746 | CZ3 | TRP | A | 109 | −2.861 | −1.590 | −8.362 | 1.00 | 0.00 | C |
| ATOM | 747 | CH2 | TRP | A | 109 | −3.098 | −0.282 | −8.770 | 1.00 | 0.00 | C |
| ATOM | 748 | N | ALA | A | 110 | −4.471 | −5.816 | −4.747 | 1.00 | 0.00 | N |
| ATOM | 749 | CA | ALA | A | 110 | −4.029 | −7.068 | −4.155 | 1.00 | 0.00 | C |
| ATOM | 750 | C | ALA | A | 110 | −4.006 | −6.927 | −2.631 | 1.00 | 0.00 | C |
| ATOM | 751 | O | ALA | A | 110 | −4.530 | −5.957 | −2.087 | 1.00 | 0.00 | O |
| ATOM | 752 | CB | ALA | A | 110 | −2.661 | −7.447 | −4.726 | 1.00 | 0.00 | C |
| ATOM | 753 | N | SER | A | 111 | −3.393 | −7.909 | −1.988 | 1.00 | 0.00 | N |
| ATOM | 754 | CA | SER | A | 111 | −3.295 | −7.907 | −0.538 | 1.00 | 0.00 | C |
| ATOM | 755 | C | SER | A | 111 | −2.581 | −6.639 | −0.064 | 1.00 | 0.00 | C |
| ATOM | 756 | O | SER | A | 111 | −3.139 | −5.860 | 0.706 | 1.00 | 0.00 | O |
| ATOM | 757 | CB | SER | A | 111 | −2.560 | −9.150 | −0.033 | 1.00 | 0.00 | C |
| ATOM | 758 | OG | SER | A | 111 | −3.462 | −10.166 | 0.395 | 1.00 | 0.00 | O |
| ATOM | 759 | N | ARG | A | 112 | −1.357 | −6.473 | −0.544 | 1.00 | 0.00 | N |
| ATOM | 760 | CA | ARG | A | 112 | −0.561 | −5.313 | −0.179 | 1.00 | 0.00 | C |
| ATOM | 761 | C | ARG | A | 112 | 0.742 | −5.290 | −0.981 | 1.00 | 0.00 | C |
| ATOM | 762 | O | ARG | A | 112 | 1.389 | −6.323 | −1.150 | 1.00 | 0.00 | O |
| ATOM | 763 | CB | ARG | A | 112 | −0.233 | −5.319 | 1.315 | 1.00 | 0.00 | C |
| ATOM | 764 | CG | ARG | A | 112 | 0.536 | −6.583 | 1.703 | 1.00 | 0.00 | C |
| ATOM | 765 | CD | ARG | A | 112 | 0.936 | −6.551 | 3.180 | 1.00 | 0.00 | C |
| ATOM | 766 | NE | ARG | A | 112 | 0.623 | −7.850 | 3.817 | 1.00 | 0.00 | N |
| ATOM | 767 | CZ | ARG | A | 112 | −0.608 | −8.230 | 4.185 | 1.00 | 0.00 | C |
| ATOM | 768 | NH1 | ARG | A | 112 | −1.650 | −7.412 | 3.980 | 1.00 | 0.00 | N |
| ATOM | 769 | NH2 | ARG | A | 112 | −0.798 | −9.427 | 4.756 | 1.00 | 0.00 | N |
| ATOM | 770 | N | VAL | A | 113 | 1.087 | −4.102 | −1.453 | 1.00 | 0.00 | N |
| ATOM | 771 | CA | VAL | A | 113 | 2.302 | −3.931 | −2.232 | 1.00 | 0.00 | C |
| ATOM | 772 | C | VAL | A | 113 | 3.466 | −4.613 | −1.511 | 1.00 | 0.00 | C |
| ATOM | 773 | O | VAL | A | 113 | 3.441 | −4.767 | −0.291 | 1.00 | 0.00 | O |
| ATOM | 774 | CB | VAL | A | 113 | 2.550 | −2.444 | −2.495 | 1.00 | 0.00 | C |
| ATOM | 775 | CG1 | VAL | A | 113 | 3.235 | −1.783 | −1.297 | 1.00 | 0.00 | C |
| ATOM | 776 | CG2 | VAL | A | 113 | 3.365 | −2.242 | −3.773 | 1.00 | 0.00 | C |
| ATOM | 777 | N | ASN | A | 114 | 4.459 | −5.003 | −2.296 | 1.00 | 0.00 | N |
| ATOM | 778 | CA | ASN | A | 114 | 5.631 | −5.666 | −1.748 | 1.00 | 0.00 | C |
| ATOM | 779 | C | ASN | A | 114 | 6.726 | −5.721 | −2.814 | 1.00 | 0.00 | C |
| ATOM | 780 | O | ASN | A | 114 | 6.437 | −5.680 | −4.009 | 1.00 | 0.00 | O |
| ATOM | 781 | CB | ASN | A | 114 | 5.306 | −7.101 | −1.329 | 1.00 | 0.00 | C |
| ATOM | 782 | CG | ASN | A | 114 | 5.114 | −7.999 | −2.552 | 1.00 | 0.00 | C |
| ATOM | 783 | ND2 | ASN | A | 114 | 3.929 | −7.865 | −3.140 | 1.00 | 0.00 | N |
| ATOM | 784 | OD1 | ASN | A | 114 | 5.983 | −8.763 | −2.937 | 1.00 | 0.00 | O |
| ATOM | 785 | N | TYR | A | 115 | 7.962 | −5.812 | −2.344 | 1.00 | 0.00 | N |
| ATOM | 786 | CA | TYR | A | 115 | 9.102 | −5.873 | −3.243 | 1.00 | 0.00 | C |
| ATOM | 787 | C | TYR | A | 115 | 10.406 | −6.049 | −2.462 | 1.00 | 0.00 | C |
| ATOM | 788 | O | TYR | A | 115 | 10.963 | −5.079 | −1.950 | 1.00 | 0.00 | O |
| ATOM | 789 | CB | TYR | A | 115 | 9.135 | −4.529 | −3.973 | 1.00 | 0.00 | C |

TABLE 3-continued

The atomic coordinates for a representative conformer (without Hydrogens)(SEQ ID NO: 39).

| ATOM | 790 | CG | TYR | A | 115 | 9.095 | −3.315 | −3.043 | 1.00 | 0.00 | C |
|---|---|---|---|---|---|---|---|---|---|---|---|
| ATOM | 791 | CD1 | TYR | A | 115 | 10.269 | −2.692 | −2.669 | 1.00 | 0.00 | C |
| ATOM | 792 | CD2 | TYR | A | 115 | 7.885 | −2.841 | −2.579 | 1.00 | 0.00 | C |
| ATOM | 793 | CE1 | TYR | A | 115 | 10.231 | −1.550 | −1.794 | 1.00 | 0.00 | C |
| ATOM | 794 | CE2 | TYR | A | 115 | 7.847 | −1.699 | −1.703 | 1.00 | 0.00 | C |
| ATOM | 795 | CZ | TYR | A | 115 | 9.021 | −1.109 | −1.355 | 1.00 | 0.00 | C |
| ATOM | 796 | OH | TYR | A | 115 | 8.985 | −0.029 | −0.529 | 1.00 | 0.00 | O |
| ATOM | 797 | N | SER | A | 116 | 10.855 | −7.294 | −2.396 | 1.00 | 0.00 | N |
| ATOM | 798 | CA | SER | A | 116 | 12.084 | −7.608 | −1.687 | 1.00 | 0.00 | C |
| ATOM | 799 | C | SER | A | 116 | 13.100 | −8.227 | −2.649 | 1.00 | 0.00 | C |
| ATOM | 800 | O | SER | A | 116 | 14.205 | −8.585 | −2.245 | 1.00 | 0.00 | O |
| ATOM | 801 | CB | SER | A | 116 | 11.817 | −8.557 | −0.516 | 1.00 | 0.00 | C |
| ATOM | 802 | OG | SER | A | 116 | 11.152 | −9.746 | −0.934 | 1.00 | 0.00 | O |
| ATOM | 803 | N | HIS | A | 117 | 12.690 | −8.333 | −3.905 | 1.00 | 0.00 | N |
| ATOM | 804 | CA | HIS | A | 117 | 13.550 | −8.902 | −4.928 | 1.00 | 0.00 | C |
| ATOM | 805 | C | HIS | A | 117 | 14.315 | −7.782 | −5.635 | 1.00 | 0.00 | C |
| ATOM | 806 | O | HIS | A | 117 | 14.884 | −7.994 | −6.706 | 1.00 | 0.00 | O |
| ATOM | 807 | CB | HIS | A | 117 | 12.744 | −9.773 | −5.894 | 1.00 | 0.00 | C |
| ATOM | 808 | CG | HIS | A | 117 | 12.023 | −10.922 | −5.231 | 1.00 | 0.00 | C |
| ATOM | 809 | CD2 | HIS | A | 117 | 10.691 | −11.198 | −5.125 | 1.00 | 0.00 | C |
| ATOM | 810 | ND1 | HIS | A | 117 | 12.687 | −11.946 | −4.578 | 1.00 | 0.00 | N |
| ATOM | 811 | CE1 | HIS | A | 117 | 11.786 | −12.795 | −4.106 | 1.00 | 0.00 | C |
| ATOM | 812 | NE2 | HIS | A | 117 | 10.550 | −12.329 | −4.446 | 1.00 | 0.00 | N |
| ATOM | 813 | N | CYS | A | 118 | 14.304 | −6.615 | −5.010 | 1.00 | 0.00 | N |
| ATOM | 814 | CA | CYS | A | 118 | 14.991 | −5.461 | −5.566 | 1.00 | 0.00 | C |
| ATOM | 815 | C | CYS | A | 118 | 16.097 | −5.046 | −4.596 | 1.00 | 0.00 | C |
| ATOM | 816 | O | CYS | A | 118 | 17.236 | −4.824 | −5.005 | 1.00 | 0.00 | O |
| ATOM | 817 | CB | CYS | A | 118 | 14.022 | −4.312 | −5.854 | 1.00 | 0.00 | C |
| ATOM | 818 | SG | CYS | A | 118 | 14.668 | −3.030 | −6.989 | 1.00 | 0.00 | S |
| ATOM | 819 | N | GLU | A | 119 | 15.724 | −4.953 | −3.328 | 1.00 | 0.00 | N |
| ATOM | 820 | CA | GLU | A | 119 | 16.671 | −4.567 | −2.295 | 1.00 | 0.00 | C |
| ATOM | 821 | C | GLU | A | 119 | 17.965 | −5.371 | −2.434 | 1.00 | 0.00 | C |
| ATOM | 822 | O | GLU | A | 119 | 19.053 | −4.801 | −2.477 | 1.00 | 0.00 | O |
| ATOM | 823 | CB | GLU | A | 119 | 16.064 | −4.742 | −0.901 | 1.00 | 0.00 | C |
| ATOM | 824 | CG | GLU | A | 119 | 16.248 | −3.477 | −0.060 | 1.00 | 0.00 | C |
| ATOM | 825 | CD | GLU | A | 119 | 16.663 | −3.826 | 1.370 | 1.00 | 0.00 | C |
| ATOM | 826 | OE1 | GLU | A | 119 | 17.839 | −3.559 | 1.701 | 1.00 | 0.00 | O |
| ATOM | 827 | OE2 | GLU | A | 119 | 15.795 | −4.351 | 2.102 | 1.00 | 0.00 | O |
| ATOM | 828 | N | PRO | A | 120 | 17.799 | −6.719 | −2.503 | 1.00 | 0.00 | N |
| ATOM | 829 | CA | PRO | A | 120 | 18.941 | −7.609 | −2.637 | 1.00 | 0.00 | C |
| ATOM | 830 | C | PRO | A | 120 | 19.501 | −7.571 | −4.060 | 1.00 | 0.00 | C |
| ATOM | 831 | O | PRO | A | 120 | 18.801 | −7.899 | −5.016 | 1.00 | 0.00 | O |
| ATOM | 832 | CB | PRO | A | 120 | 18.420 | −8.980 | −2.240 | 1.00 | 0.00 | C |
| ATOM | 833 | CG | PRO | A | 120 | 16.906 | −8.898 | −2.347 | 1.00 | 0.00 | C |
| ATOM | 834 | CD | PRO | A | 120 | 16.525 | −7.431 | −2.455 | 1.00 | 0.00 | C |
| ATOM | 835 | N | ILE | A | 121 | 20.759 | −7.166 | −4.155 | 1.00 | 0.00 | N |
| ATOM | 836 | CA | ILE | A | 121 | 21.422 | −7.081 | −5.445 | 1.00 | 0.00 | C |
| ATOM | 837 | C | ILE | A | 121 | 22.865 | −7.571 | −5.307 | 1.00 | 0.00 | C |
| ATOM | 838 | O | ILE | A | 121 | 23.438 | −7.525 | −4.219 | 1.00 | 0.00 | O |
| ATOM | 839 | CB | ILE | A | 121 | 21.305 | −5.667 | −6.016 | 1.00 | 0.00 | C |
| ATOM | 840 | CG1 | ILE | A | 121 | 19.869 | −5.368 | −6.451 | 1.00 | 0.00 | C |
| ATOM | 841 | CG2 | ILE | A | 121 | 22.306 | −5.449 | −7.153 | 1.00 | 0.00 | C |
| ATOM | 842 | CD1 | ILE | A | 121 | 19.536 | −6.073 | −7.766 | 1.00 | 0.00 | C |
| ATOM | 843 | N | LEU | A | 122 | 23.412 | −8.028 | −6.423 | 1.00 | 0.00 | N |
| ATOM | 844 | CA | LEU | A | 122 | 24.777 | −8.526 | −6.439 | 1.00 | 0.00 | C |
| ATOM | 845 | C | LEU | A | 122 | 25.740 | −7.354 | −6.640 | 1.00 | 0.00 | C |
| ATOM | 846 | O | LEU | A | 122 | 26.573 | −7.378 | −7.544 | 1.00 | 0.00 | O |
| ATOM | 847 | CB | LEU | A | 122 | 24.931 | −9.634 | −7.483 | 1.00 | 0.00 | C |
| ATOM | 848 | CG | LEU | A | 122 | 24.599 | −9.247 | −8.925 | 1.00 | 0.00 | C |
| ATOM | 849 | CD1 | LEU | A | 122 | 25.832 | −9.367 | −9.823 | 1.00 | 0.00 | C |
| ATOM | 850 | CD2 | LEU | A | 122 | 23.422 | −10.069 | −9.456 | 1.00 | 0.00 | C |
| ATOM | 851 | N | ASP | A | 123 | 25.592 | −6.355 | −5.782 | 1.00 | 0.00 | N |
| ATOM | 852 | CA | ASP | A | 123 | 26.438 | −5.176 | −5.853 | 1.00 | 0.00 | C |
| ATOM | 853 | C | ASP | A | 123 | 26.041 | −4.200 | −4.744 | 1.00 | 0.00 | C |
| ATOM | 854 | O | ASP | A | 123 | 25.302 | −3.246 | −4.987 | 1.00 | 0.00 | O |
| ATOM | 855 | CB | ASP | A | 123 | 26.272 | −4.460 | −7.196 | 1.00 | 0.00 | C |
| ATOM | 856 | CG | ASP | A | 123 | 27.490 | −3.654 | −7.653 | 1.00 | 0.00 | C |
| ATOM | 857 | OD1 | ASP | A | 123 | 27.711 | −2.575 | −7.061 | 1.00 | 0.00 | O |
| ATOM | 858 | OD2 | ASP | A | 123 | 28.172 | −4.134 | −8.584 | 1.00 | 0.00 | O |
| ATOM | 859 | N | ASP | A | 124 | 26.549 | −4.472 | −3.551 | 1.00 | 0.00 | N |
| ATOM | 860 | CA | ASP | A | 124 | 26.256 | −3.630 | −2.404 | 1.00 | 0.00 | C |
| ATOM | 861 | C | ASP | A | 124 | 26.920 | −4.222 | −1.159 | 1.00 | 0.00 | C |
| ATOM | 862 | O | ASP | A | 124 | 26.823 | −5.424 | −0.912 | 1.00 | 0.00 | O |
| ATOM | 863 | CB | ASP | A | 124 | 24.749 | −3.554 | −2.147 | 1.00 | 0.00 | C |
| ATOM | 864 | CG | ASP | A | 124 | 24.204 | −2.143 | −1.908 | 1.00 | 0.00 | C |
| ATOM | 865 | OD1 | ASP | A | 124 | 24.573 | −1.562 | −0.865 | 1.00 | 0.00 | O |
| ATOM | 866 | OD2 | ASP | A | 124 | 23.431 | −1.680 | −2.773 | 1.00 | 0.00 | O |

TABLE 3-continued

The atomic coordinates for a representative conformer (without Hydrogens)(SEQ ID NO: 39).

| ATOM | 867 | N | LYS | A | 125 | 27.578 | −3.352 | −0.407 | 1.00 | 0.00 | N |
|---|---|---|---|---|---|---|---|---|---|---|---|
| ATOM | 868 | CA | LYS | A | 125 | 28.257 | −3.775 | 0.806 | 1.00 | 0.00 | C |
| ATOM | 869 | C | LYS | A | 125 | 29.054 | −2.599 | 1.375 | 1.00 | 0.00 | C |
| ATOM | 870 | O | LYS | A | 125 | 30.234 | −2.439 | 1.068 | 1.00 | 0.00 | O |
| ATOM | 871 | CB | LYS | A | 125 | 29.104 | −5.021 | 0.540 | 1.00 | 0.00 | C |
| ATOM | 872 | CG | LYS | A | 125 | 28.631 | −6.198 | 1.396 | 1.00 | 0.00 | C |
| ATOM | 873 | CD | LYS | A | 125 | 28.934 | −5.956 | 2.876 | 1.00 | 0.00 | C |
| ATOM | 874 | CE | LYS | A | 125 | 28.536 | −7.167 | 3.722 | 1.00 | 0.00 | C |
| ATOM | 875 | NZ | LYS | A | 125 | 27.065 | −7.224 | 3.884 | 1.00 | 0.00 | N |
| ATOM | 876 | N | GLN | A | 126 | 28.377 | −1.807 | 2.193 | 1.00 | 0.00 | N |
| ATOM | 877 | CA | GLN | A | 126 | 29.008 | −0.651 | 2.807 | 1.00 | 0.00 | C |
| ATOM | 878 | C | GLN | A | 126 | 28.476 | −0.448 | 4.227 | 1.00 | 0.00 | C |
| ATOM | 879 | O | GLN | A | 126 | 27.580 | −1.167 | 4.667 | 1.00 | 0.00 | O |
| ATOM | 880 | CB | GLN | A | 126 | 28.797 | 0.604 | 1.958 | 1.00 | 0.00 | C |
| ATOM | 881 | CG | GLN | A | 126 | 29.901 | 0.748 | 0.909 | 1.00 | 0.00 | C |
| ATOM | 882 | CD | GLN | A | 126 | 29.988 | 2.187 | 0.398 | 1.00 | 0.00 | C |
| ATOM | 883 | NE2 | GLN | A | 126 | 28.925 | 2.580 | −0.298 | 1.00 | 0.00 | N |
| ATOM | 884 | OE1 | GLN | A | 126 | 30.957 | 2.895 | 0.621 | 1.00 | 0.00 | O |
| ATOM | 885 | N | ARG | A | 127 | 29.052 | 0.534 | 4.906 | 1.00 | 0.00 | N |
| ATOM | 886 | CA | ARG | A | 127 | 28.646 | 0.841 | 6.267 | 1.00 | 0.00 | C |
| ATOM | 887 | C | ARG | A | 127 | 28.990 | −0.324 | 7.198 | 1.00 | 0.00 | C |
| ATOM | 888 | O | ARG | A | 127 | 28.762 | −1.483 | 6.858 | 1.00 | 0.00 | O |
| ATOM | 889 | CB | ARG | A | 127 | 27.144 | 1.120 | 6.345 | 1.00 | 0.00 | C |
| ATOM | 890 | CG | ARG | A | 127 | 26.874 | 2.608 | 6.579 | 1.00 | 0.00 | C |
| ATOM | 891 | CD | ARG | A | 127 | 25.454 | 2.982 | 6.151 | 1.00 | 0.00 | C |
| ATOM | 892 | NE | ARG | A | 127 | 25.308 | 2.822 | 4.687 | 1.00 | 0.00 | N |
| ATOM | 893 | CZ | ARG | A | 127 | 25.868 | 3.637 | 3.783 | 1.00 | 0.00 | C |
| ATOM | 894 | NH1 | ARG | A | 127 | 26.613 | 4.675 | 4.186 | 1.00 | 0.00 | N |
| ATOM | 895 | NH2 | ARG | A | 127 | 25.681 | 3.415 | 2.474 | 1.00 | 0.00 | N |
| ATOM | 896 | N | LYS | A | 128 | 29.534 | 0.026 | 8.355 | 1.00 | 0.00 | N |
| ATOM | 897 | CA | LYS | A | 128 | 29.913 | −0.975 | 9.337 | 1.00 | 0.00 | C |
| ATOM | 898 | C | LYS | A | 128 | 30.364 | −0.278 | 10.621 | 1.00 | 0.00 | C |
| ATOM | 899 | O | LYS | A | 128 | 29.742 | −0.438 | 11.671 | 1.00 | 0.00 | O |
| ATOM | 900 | CB | LYS | A | 128 | 30.956 | −1.930 | 8.755 | 1.00 | 0.00 | C |
| ATOM | 901 | CG | LYS | A | 128 | 30.876 | −3.304 | 9.422 | 1.00 | 0.00 | C |
| ATOM | 902 | CD | LYS | A | 128 | 31.862 | −3.406 | 10.588 | 1.00 | 0.00 | C |
| ATOM | 903 | CE | LYS | A | 128 | 32.473 | −4.806 | 10.669 | 1.00 | 0.00 | C |
| ATOM | 904 | NZ | LYS | A | 128 | 31.466 | −5.784 | 11.140 | 1.00 | 0.00 | N |
| ATOM | 905 | N | TYR | A | 129 | 31.443 | 0.480 | 10.497 | 1.00 | 0.00 | N |
| ATOM | 906 | CA | TYR | A | 129 | 31.986 | 1.203 | 11.635 | 1.00 | 0.00 | C |
| ATOM | 907 | C | TYR | A | 129 | 32.234 | 0.260 | 12.815 | 1.00 | 0.00 | C |
| ATOM | 908 | O | TYR | A | 129 | 31.843 | −0.906 | 12.776 | 1.00 | 0.00 | O |
| ATOM | 909 | CB | TYR | A | 129 | 30.922 | 2.226 | 12.031 | 1.00 | 0.00 | C |
| ATOM | 910 | CG | TYR | A | 129 | 31.314 | 3.104 | 13.221 | 1.00 | 0.00 | C |
| ATOM | 911 | CD1 | TYR | A | 129 | 32.457 | 3.876 | 13.163 | 1.00 | 0.00 | C |
| ATOM | 912 | CD2 | TYR | A | 129 | 30.526 | 3.123 | 14.354 | 1.00 | 0.00 | C |
| ATOM | 913 | CE1 | TYR | A | 129 | 32.826 | 4.702 | 14.283 | 1.00 | 0.00 | C |
| ATOM | 914 | CE2 | TYR | A | 129 | 30.895 | 3.949 | 15.474 | 1.00 | 0.00 | C |
| ATOM | 915 | CZ | TYR | A | 129 | 32.027 | 4.698 | 15.384 | 1.00 | 0.00 | C |
| ATOM | 916 | OH | TYR | A | 129 | 32.376 | 5.478 | 16.441 | 1.00 | 0.00 | O |
| ATOM | 917 | N | ASP | A | 130 | 32.882 | 0.800 | 13.836 | 1.00 | 0.00 | N |
| ATOM | 918 | CA | ASP | A | 130 | 33.187 | 0.022 | 15.025 | 1.00 | 0.00 | C |
| ATOM | 919 | C | ASP | A | 130 | 34.069 | 0.852 | 15.960 | 1.00 | 0.00 | C |
| ATOM | 920 | O | ASP | A | 130 | 34.611 | 1.880 | 15.558 | 1.00 | 0.00 | O |
| ATOM | 921 | CB | ASP | A | 130 | 33.947 | −1.256 | 14.668 | 1.00 | 0.00 | C |
| ATOM | 922 | CG | ASP | A | 130 | 33.168 | −2.554 | 14.883 | 1.00 | 0.00 | C |
| ATOM | 923 | OD1 | ASP | A | 130 | 32.795 | −3.169 | 13.860 | 1.00 | 0.00 | O |
| ATOM | 924 | OD2 | ASP | A | 130 | 32.961 | −2.902 | 16.065 | 1.00 | 0.00 | O |
| ATOM | 925 | N | LEU | A | 131 | 34.187 | 0.373 | 17.190 | 1.00 | 0.00 | N |
| ATOM | 926 | CA | LEU | A | 131 | 34.995 | 1.058 | 18.185 | 1.00 | 0.00 | C |
| ATOM | 927 | C | LEU | A | 131 | 35.959 | 0.059 | 18.828 | 1.00 | 0.00 | C |
| ATOM | 928 | O | LEU | A | 131 | 35.558 | −1.043 | 19.201 | 1.00 | 0.00 | O |
| ATOM | 929 | CB | LEU | A | 131 | 34.102 | 1.786 | 19.192 | 1.00 | 0.00 | C |
| ATOM | 930 | CG | LEU | A | 131 | 34.827 | 2.580 | 20.280 | 1.00 | 0.00 | C |
| ATOM | 931 | CD1 | LEU | A | 131 | 35.608 | 3.750 | 19.677 | 1.00 | 0.00 | C |
| ATOM | 932 | CD2 | LEU | A | 131 | 33.851 | 3.040 | 21.365 | 1.00 | 0.00 | C |
| ATOM | 933 | N | HIS | A | 132 | 37.210 | 0.479 | 18.939 | 1.00 | 0.00 | N |
| ATOM | 934 | CA | HIS | A | 132 | 38.235 | −0.365 | 19.531 | 1.00 | 0.00 | C |
| ATOM | 935 | C | HIS | A | 132 | 39.082 | 0.460 | 20.501 | 1.00 | 0.00 | C |
| ATOM | 936 | O | HIS | A | 132 | 39.332 | 1.641 | 20.263 | 1.00 | 0.00 | O |
| ATOM | 937 | CB | HIS | A | 132 | 39.070 | −1.046 | 18.445 | 1.00 | 0.00 | C |
| ATOM | 938 | CG | HIS | A | 132 | 38.974 | −2.554 | 18.452 | 1.00 | 0.00 | C |
| ATOM | 939 | CD2 | HIS | A | 132 | 39.914 | −3.508 | 18.196 | 1.00 | 0.00 | C |
| ATOM | 940 | ND1 | HIS | A | 132 | 37.803 | −3.229 | 18.748 | 1.00 | 0.00 | N |
| ATOM | 941 | CE1 | HIS | A | 132 | 38.040 | −4.530 | 18.671 | 1.00 | 0.00 | C |
| ATOM | 942 | NE2 | HIS | A | 132 | 39.349 | −4.701 | 18.329 | 1.00 | 0.00 | N |
| ATOM | 943 | N | TYR | A | 133 | 39.501 | −0.194 | 21.573 | 1.00 | 0.00 | N |

TABLE 3-continued

The atomic coordinates for a representative conformer (without Hydrogens)(SEQ ID NO: 39).

| ATOM | 944 | CA  | TYR | A | 133 | 40.315 | 0.464  | 22.581 | 1.00 | 0.00 | C |
|------|-----|-----|-----|---|-----|--------|--------|--------|------|------|---|
| ATOM | 945 | C   | TYR | A | 133 | 41.779 | 0.539  | 22.140 | 1.00 | 0.00 | C |
| ATOM | 946 | O   | TYR | A | 133 | 42.370 | 1.618  | 22.119 | 1.00 | 0.00 | O |
| ATOM | 947 | CB  | TYR | A | 133 | 40.218 | −0.406 | 23.836 | 1.00 | 0.00 | C |
| ATOM | 948 | CG  | TYR | A | 133 | 40.619 | 0.315  | 25.125 | 1.00 | 0.00 | C |
| ATOM | 949 | CD1 | TYR | A | 133 | 39.664 | 0.611  | 26.076 | 1.00 | 0.00 | C |
| ATOM | 950 | CD2 | TYR | A | 133 | 41.938 | 0.668  | 25.336 | 1.00 | 0.00 | C |
| ATOM | 951 | CE1 | TYR | A | 133 | 40.043 | 1.290  | 27.289 | 1.00 | 0.00 | C |
| ATOM | 952 | CE2 | TYR | A | 133 | 42.315 | 1.346  | 26.549 | 1.00 | 0.00 | C |
| ATOM | 953 | CZ  | TYR | A | 133 | 41.349 | 1.624  | 27.465 | 1.00 | 0.00 | C |
| ATOM | 954 | OH  | TYR | A | 133 | 41.707 | 2.264  | 28.611 | 1.00 | 0.00 | O |
| END  |     |     |     |   |     |        |        |        |      |      |   |

Example 3

Description of the Structure

Figure 1B:
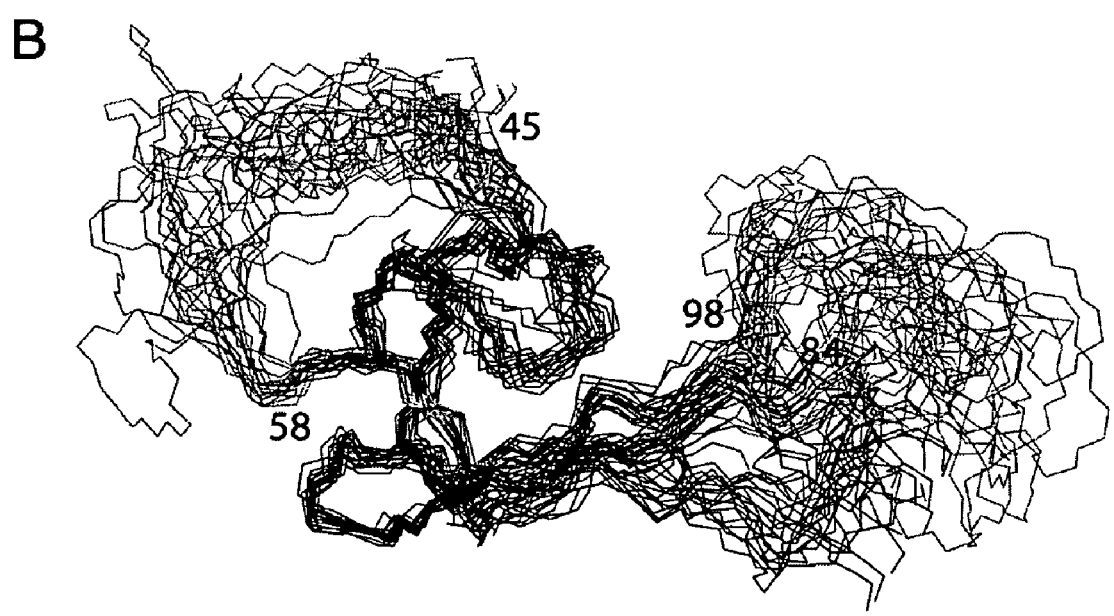
Figures 2A, 2B, 2C, 2D:
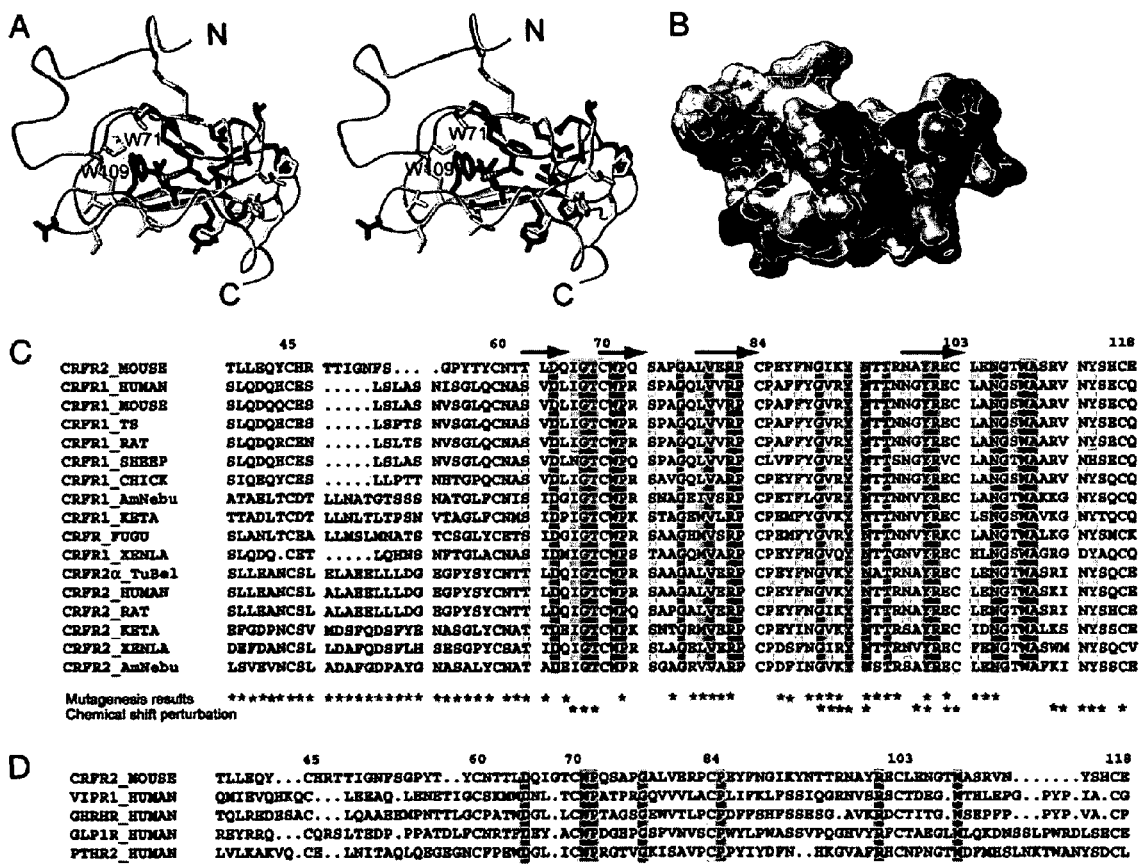
FIGS. 2A-2C show an image of mapping the conserved amino acids onto the 3D structure of $ECD_1$-CRFR2β.
FIG. 2D is a sequence alignment of the $ECD_1$ of the B1 GPCR family. Only a representative set of sequences are shown. The sequence identifiers for those specific sequences set forth in FIG. 2C are as follows: CRFR2_MOUSE is SEQ ID NO:17, CRFR1_HUMAN is SEQ ID NO:18; CRFR1 MOUSE is SEQ ID NO:19; CRFR1_TS is SEQ ID NO:20; CRFR1_RAT is SEQ ID NO:21; CRFR1_SHEEP is SEQ ID NO:22; CRFR1_CHICK is SEQ ID NO:23; CRFR1_AmNebu is SEQ ID NO:24; CRFR1_KETA is SEQ ID NO:25; CRFR_FUGU is SEQ ID NO:26; CRFR1_XENLA is SEQ ID NO:27; CRFR2α_TuBel is SEQ ID NO:28; CRFR2_HUMAN is SEQ ID NO:29; CRFR2_RAT is SEQ ID NO:30; CRFR2_KETA is SEQ ID NO:31; CRFR2_XENLA is SEQ ID NO:32; CRFR2_AmNebu is SEQ ID NO:33. The sequence identifiers for those specific sequences set forth in FIG. 2D are as follows: CRFR2_MOUSE is SEQ ID NO:34; VIPR1_HUMAN is SEQ ID NO:35; GHRHR_HUMAN is SEQ ID NO:36; GLP1R_HUMAN is SEQ ID NO:37; PTHR2_HUMAN is SEQ ID NO: 38.

The NMR structure of $^{13}$C, $^{15}$N-labeled ECD$_1$-CRFR2 β has been determined using triple resonance experiments for the backbone assignment and NOESY experiments for the distance restraints (Table 2). The NMR structure of ECD$_1$-CRFR2 β contains two antiparallel β-sheet regions comprising residues 63-64 (β 1 strand), 70-71 (β 2 strand), 79-82 (β 3 strand) and 99-102 (β 4 strand) (FIG. 1A). The polypeptide fold is stabilized by three disulfide bonds between residues Cys45-Cys70, Cys60-Cys103, and Cys84-Cys118 and by a central core consisting of a salt-bridge involving Asp65-Arg101, sandwiched between the aromatic rings of Trp71 and Trp109 (FIG. 2A). The two β-sheets, interconnected by this core, form the scaffold flanked by two disordered regions (residues 39-58, and 84-98).

Furthermore, the core is surrounded by a second layer of highly conserved residues, Thr69, Val80, Arg82, and of conservatively conserved residues Thr63, Ser74, Ile67 (dark and light blue residues in FIG. 2C). The other conserved residues include Pro72 and Pro83, which are presumably important for ending the β-strands, as well as Gly77, Asn106 and Gly107 located in the hinge regions of the two β-sheets, probably important for their relative orientation. Another cluster of conserved residues is present in the disordered loop between strands β 3 and β 4 (Gly92, Phe93, Asn94 and Thr96). In contrast, the disordered loop from residues 39-58 is highly variable in amino acid sequence. The structure of ECD$_1$-CRFR2 β is identified as a short consensus repeat (SCR) commonly found in proteins of the complement system including the first SCR module of the human β2-glycoprotein (PDB code 1C1Z), the closest structure found by the DALI server. Among GPCRs, the SCR domain has been predicted to occur in the N-terminal domain only of the GABA receptor.

Example 4

Hormone Peptide Binding Site

Figure 3A:
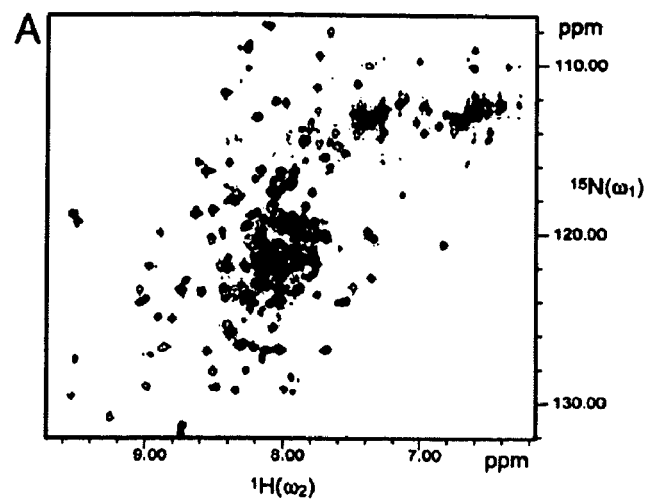
FIGS. 3A-3D depict the identification of the binding site of astressin on the 3D structure of $ECD_1$-CRFR2β.
Figure 3B:
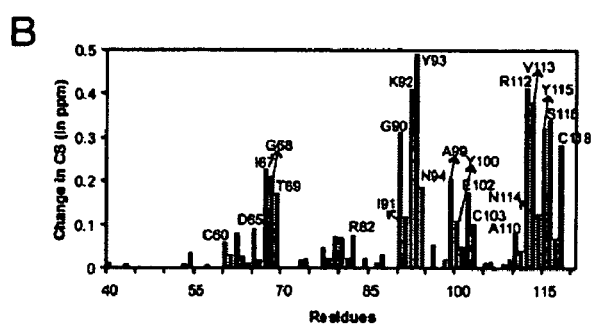
Figure 3C:
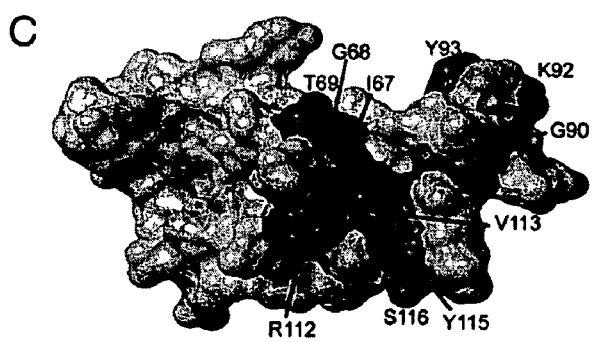
Figure 3D:
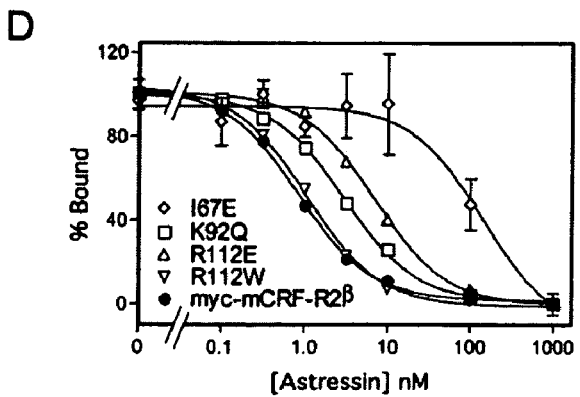

To obtain detailed structural insights about the binding interface, the interaction between the potent peptide antagonist, astressin, and the ECD$_1$-CRFR2β was studied using NMR chemical shift perturbation experiments. FIG. 3A shows the HMQC spectra of $^{15}$N-labeled ECD$_1$-CRFR2β in the absence and presence of equimolar astressin. Largest chemical shift perturbations are observed in the segments comprising residues 67-69, 90-93, 102-103 and 112-116, respectively (FIG. 3B). These residues are clustered in the cleft region between the tip of the first β-sheet and the edge of the "palm" of the second β-sheet (FIG. 3C). The observed changes in the chemical shifts in the disordered loop region 85-98 are indicative of a folding upon ligand binding. This interpretation is supported by the circular dichroism data that revealed a conformational change towards a more structured ECD$_1$-CRFR2β upon ligand binding. A structure-evolution approach that assumes the conservation of the ligand-receptor interface within the CRF-R family and that concomitantly screens the surface of ECD$_1$ for patches with conserved and similar amino acids highlights the same surface region also (FIG. 2B). Furthermore, studies of mutant CRFR2β, that show reduced binding affinity, serve to confirm the integrity of the binding site in the full-length receptor. The mutation, R112E in myc-mCRFR2β results in a ~7-fold decrease in the affinity for astressin: The inhibitory binding constants, $K_i$'s, are: 7.2 (6.3-8.3) nM for myc-mCRFR2β (R112E) compared to 1.1 (0.8-1.5) nM for myc-mCRFR2β. Introducing the mutation, I67E, results in a larger decrease in the affinity for astressin: $K_i$=128 (85-191) nM (FIG. 3D). The 167E mutation also reduces (by ~3-fold) the affinity for agonist sauvagine. Mutations of residues T69 or N114, which show only small chemical shift perturbations upon binding to astressin, do not significantly influence the binding affinities. These data suggest that these chemical shift perturbations are an indirect effect of binding. Mutagenesis studies of CRF receptors reported in literature (See Dautzenberg et al., 2002 and 2004; Wille et al., 1999) are also consistent with the proposed interaction surface (FIG. 2C). The hormone-binding site also provides a structural basis for explaining the binding specificity of ligands. As mentioned above, CRFR2β binds with high affinity to Ucn 1, Ucn 2, Ucn 3, and to the antagonist astressin, but with lower affinity to CRF. On the other hand, CRF binds to CRF-R1 with higher affinity than does Ucn 2 or Ucn 3. These different binding specificities of CRF receptors are explained by the presence of different amino acids in the binding pocket (FIGS. 2 and 3). For example, the point mutations, R112W and K92Q, replacing the residues R112 or K92 in mCRFR2β with the residues found in xCRF-R1, results in a 2-3-fold lower binding affinity for astressin: $K_i$=1.9 (1.0-3.4) nM for myc-mCRFR2β (R112W) and $K_i$=3.1 (2.4-3.9) nM for myc-mCRFR2β (K92Q). To ensure the conservation of the proposed binding site for different ligands, the chemical shift perturbation experiment was also performed with CRF. In the presence of CRF, the same cross-peaks of ECD$_1$-CRFR2β were affected as were influenced by astressin. However, instead of a chemical shift change, the cross-peaks were broadened beyond detection, probably due to slow conformational exchange induced by the low binding affinity of CRF.

Example 5

Model for Receptor Activation

Figures 4A, 4B:
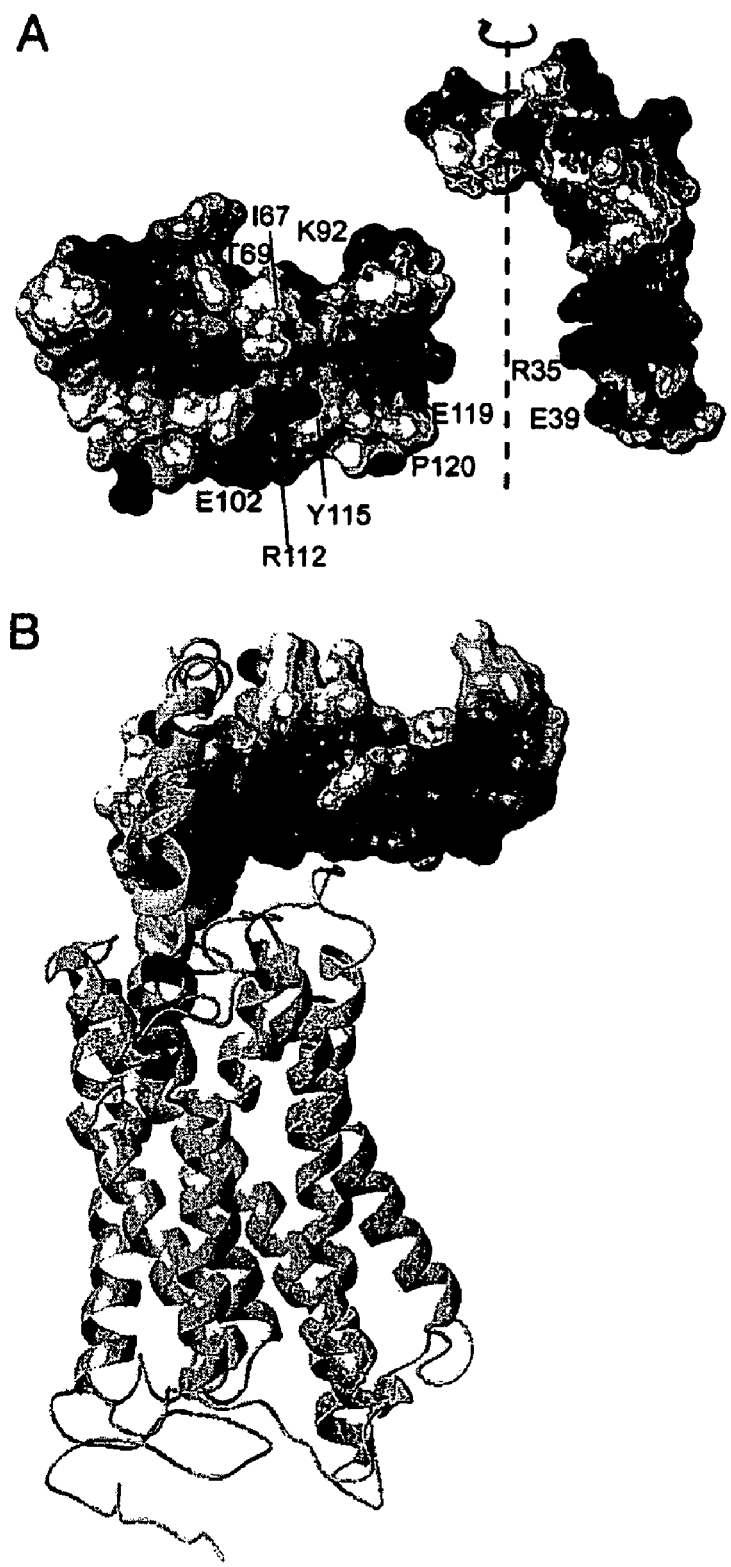
FIGS. 4A-4B show a two-step model for hormone binding and receptor activation.

The surface potential of the 3D structure provides an insight into receptor activation mechanism. An accumulated distribution of positive charges on the "back-side" of the structure displayed in FIGS. 1-3 (Arg47, Arg82, Arg97) suggests its orientation towards the negatively charged extracellular domains 2-4 and the transmembrane segment of CRFR2 β (FIG. 4B). This orientation is further supported by the observation that amino acid replacements between CRFR2 and CRFR1 with negative charges on the "back-side" of the $ECD_1$ have their counterpart in replacements with positive charges in the extracellular domains 2-4. The relative orientation of the $ECD_1$ and the 3D structure of $ECD_1$-CRFR2β and astressin B (FIG. 4), indicates that hormone binding and receptor activation occurs in two steps. First, the ligand binds with its C-terminal segment to the solvent exposed binding site of the $ECD_1$. Second, for an agonist ligand, the N-terminal segment, known to be important for signaling, penetrates into the transmembrane segment of the receptor producing activation of the receptor (FIG. 4B). In contrast, the peptide antagonist, astressin, lacks the first eleven N-terminal residues and, hence, is unable to penetrate the transmembrane and other ECD's of the receptor and fails to activate it. An important prerequisite for this two-step mechanism is the observed kink in the peptide ligand, astressin (FIG. 4) (Grace et al., 2004). The B1 receptors are encoded by fifteen genes in humans; the ligands for these receptors are polypeptide hormones of 27-141 amino acid residues. A structure-based analysis of the amino acid sequences of this receptor subfamily suggests that the SCR fold of the $ECD_1$ domain must be conserved in all the $B_1$ family receptors (FIG. 2D). This prediction is based on (i) the conserved disulfide bonds and their identical arrangement in the $ECD_1$'s of CRF-R1, CRFR2 β, PTHR and GLP-1R and, (ii) the conserved salt bridge (Asp65 and Arg101) surrounded by the two conserved tryptophan residues (Trp71 and Trp109), which have been identified as the key residues in the core of $ECD_1$. Additionally, two prolines, which have been proposed to be crucial for ending the β-sheet (Pro72, Pro84), and Gly77, are also conserved in the receptor subfamily.

Initial analysis of the three dimensional structure of the $ECD_1$ provides a explanation for the profound effect of the Asp60Ala mutation (position 65 in CRFR2β) in another member of this family, namely, the mouse growth hormone releasing factor (GRF) receptor. This mutant GRF receptor is impaired in its ability to bind and transduce the GRF-induced cAMP response, with the physiological consequences of a hypoplastic pituitary and a dwarf (little) phenotype. This mutation in the SCR motif would prevent the formation of the structurally important core salt-bridge thereby hindering the correct folding of the $ECD_1$ and concomitantly high affinity ligand binding.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,282,287
U.S. Pat. No. 4,542,102
U.S. Pat. No. 4,812,128
U.S. Pat. No. 4,906,122
U.S. Pat. No. 5,030,103
U.S. Pat. No. 5,252,743
U.S. Pat. No. 5,583,973
U.S. Pat. No. 5,612,894
U.S. Pat. No. 5,786,203
U.S. Pat. No. 6,080,576
U.S. Pat. No. 6,093,573
U.S. Pat. No. 6,348,466
U.S. Pat. No. 6,500,839
U.S. Pat. No. 6,514,982
U.S. Pat. No. 6,531,475
U.S. Pat. No. 6,541,469
U.S. Pat. No. 6,583,143
U.S. Pat. No. 6,664,261
U.S. Pat. No. 6,747,034
U.S. Pat. No. 4,522,752
U.S. Pat. No. 4,612,132
U.S. Pat. No. 4,745,051
U.S. Pat. No. 5,643,873
U.S. Pat. No. 5,654,276
Bitter et al., *Methods in Enzymol.*, 153:516-44, 1987.
Bugg et al., *Scientific American*, :92-98, 1993.
Camarero et al., *J. Pept. Res.*, 51(4):303-316, 1998.
Coligan et al., *Current Protocols in Immunology*, 1(2): Chapter 5, 1991.
Dautzenberg and Hauger, *Trends Pharmacol. Sci.*, 23:71-77, 2002.
Dautzenberg and Wille, *Regul. Pept.*, 118:165-173, 2004.
Dautzenberg et al., *Mol. Pharmacol.*, 61:1132-1139, 2002.
Dayhoff, and Eck, In: *Atlas of Protein Sequence and Structure*, Natl. Biomed. Res. Foundation, Silver Spring, Md., 33-41, 1968.
Furth et al., *Proc. Natl. Acad. Sci. USA*, 91:9302-9306, 1994.
George et al., *Methods Enzymol.*, 1990, 183, 333-351, 1990.
Goodman et al. In: *Perspectives in Peptide Chemistry*, 283-294, 1981.
Gossen et al., *Proc. Natl. Acad. Sci. USA*, 89:5547-5551, 1992.
Gossen et al., *Science*, 268:1766-1769, 1995.
Grace et al., *Proc. Natl. Acad. Sci. USA*, 101(35):12836-12841, 2005.
Hackeng et al., *Proc. Natl. Acad. Sci. USA*, 96:10068-10073, 1999.
Inouye & Inouye, *Nucleic Acids Res.*, 13:3101-3109, 1985.
James et al., *Science*, 260:1937-1942, 1993.
Johnson and Overington, *J. Mol. Biol.*, 233(4):716-738, 1993.
Kawashima and Kanehisa, *Nucleic Acids Res.*, 28(1):374, 2000.
Kolaskar et al., *J. Mol. Biol.*, 223:1053-1061, 1992.
Logan et al., *Proc. Natl. Acad. Sci. USA*, 81:3655-3659, 1984.
Luthy et al., *Proteins*, 10:229-239, 1991.
Nakai et al., *Protein Eng.*, 2:93-100, 1988.
No et al., *Proc. Natl. Acad. Sci. USA*, 93:3346-3351, 1996.
Palczewski et al., *Science*, 289:739-45, 2000.
PCT Appln. 90/07582
PCT Appln. 91/00868
PCT Appln. 91/07087
PCT Appln. WO 84/03564
Perrin et al., *J. Biol. Chem.*, 278:15595-600, 2003.
Riek et al., *J. Theor. Biol.*, 172:245-258, 1995.
Ruther et al., *EMBO J.*, 2:1791-1794, 1983.

Sambrook et al., In: *Molecular cloning*, Cold Spring Harbor Laboratory Press, Cold Spring Harbor, N.Y., 2001.
Smith, et al., *J. Virol.,* 46:584-593, 1983.
Szabo et al., *Curr. Opin. Struct. Biol.,* 5:699-705, 1995.
Van Heeke et al., *J. Biol. Chem.,* 264:5503-5509, 1989.
West et al., *Trends Pharmacol Sci.,* 16(2):67-75, 1995.
Wille et al., *J Neurochem.,* 72:388-395, 1999.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

LENGTHY TABLES

The patent contains a lengthy table section. A copy of the table is available in electronic form from the USPTO web site (http://seqdata.uspto.gov/?pageRequest=docDetail&DocID=US07869958B2). An electronic copy of the table will also be available from the USPTO upon request and payment of the fee set forth in 37 CFR 1.19(b)(3).

What is claimed is:

1. A method of improving binding or activity of an agonist or antagonist of a corticotropin-releasing hormone receptor 2β extracellular domain (CRFR2β-ECD1) comprising:

a) employing the structural coordinates of mouse CRFR2β-ECD1 as set forth in Table 3 to generate a three-dimensional model in silico;

b) utilizing the model as generated in step (a) to analyze the interaction(s) of known antagonists or agonists of human CRFR2β-ECD1 to amino acids 67-69, 90-93, 102, 103 and 112-116 or combinations thereof wherein said amino acids correspond to the amino acid positions in Table 3, d) ascertaining from step (b) where or how to modify said known antagonists or agonists so as to improve the binding or fit and modifying said agonists or antagonists thereby forming new/modified agonists or antagonists;

e) providing said new/modified agonists or antagonists; and f) assessing the binding and/or activity of said modified/new agonists or antagonists with CRFR2β-ECD1 by contacting said new agonists or antagonists with a CRFR2β-ECD1 polypeptide.

2. The method of claim 1, wherein the antagonist is astressin, astressin B, astressin$_2$-B, urocortin I, urocortin II, or urocortin III.

3. The method of claim 1, wherein the antagonist or agonist binds to one or more conserved amino acids in the extracellular domain of the CRFR2-ECD1.

4. The method of claim 1, wherein the antagonist or agonist binds to a short consensus repeat domain of the extracellular domain of the CRFR2-ECD1.

5. The method of claim 1, wherein the modified agonist or modified antagonist is a small molecule.

6. The method of claim 1, wherein the modified antagonist or modified agonist is a peptide.

7. The method of claim 1, wherein the modified antagonist or modified agonist is a peptidomimetic.

* * * * *

UNITED STATES PATENT AND TRADEMARK OFFICE
CERTIFICATE OF CORRECTION

PATENT NO. : 7,869,958 B2
APPLICATION NO. : 11/199821
DATED : January 11, 2011
INVENTOR(S) : Grace Christy Rani Royappa Page 1 of 1

It is certified that error appears in the above-identified patent and that said Letters Patent is hereby corrected as shown below:

In column 1, lines 7-8, delete
"The government owns rights in the present invention pursuant to NIH grant numbers DK26741 and DK059953." and insert
--This invention was made with government support under grant numbers DK 26741 and DK059953 awarded by the National Institutes of Health. The government has certain rights in the invention--.

Signed and Sealed this
Third Day of May, 2011

David J. Kappos
*Director of the United States Patent and Trademark Office*